US 6,645,175 B2

(12) United States Patent
Kriesel et al.

(10) Patent No.: US 6,645,175 B2
(45) Date of Patent: *Nov. 11, 2003

(54) VARIABLE RATE INFUSION APPARATUS WITH INDICATOR AND ADJUSTABLE RATE CONTROL

(75) Inventors: Marshall S. Kriesel, St. Paul, MN (US); Steven M. Arnold, Minnetanka, MN (US); James Garrison, Minneapolis, MN (US); Farhad Kazemzadeh, Bloomington, MN (US)

(73) Assignee: Science Incorporated, Bloomingtown, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/858,131

(22) Filed: May 14, 2001

(65) Prior Publication Data

US 2002/0177809 A1 Nov. 28, 2002

Related U.S. Application Data

(63) Continuation-in-part of application No. 09/165,713, filed on Oct. 2, 1998, now Pat. No. 6,231,545, which is a continuation-in-part of application No. 08/768,663, filed on Dec. 18, 1996, now Pat. No. 5,840,071.

(51) Int. Cl.[7] ............................................. A61M 37/00
(52) U.S. Cl. .................... 604/132; 604/151; 604/890.1; 604/246; 604/248
(58) Field of Search ................................ 604/122, 123, 604/131, 132, 151, 153, 246, 248, 186, 207, 890.1, 190, 247, 133, 86, 89

(56) References Cited

U.S. PATENT DOCUMENTS 5,395,340 A * 3/1995 Lee ............................. 604/151
6,183,441 B1 * 2/2001 Kriesel et al. ............... 604/132

* cited by examiner

Primary Examiner—Glenn K. Dawson
Assistant Examiner—Jennifer Maynard
(74) Attorney, Agent, or Firm—Schwegman, Lundberg, Woessner & Kluth, P.A.

(57) ABSTRACT

An apparatus for accurately infusing medicinal agents into an ambulatory patient at specific rates over extended periods of time. The apparatus is of a compact, low profile, laminate construction and includes an elastic distendable membrane, chamber having a fluid outlet. The apparatus also includes a highly novel fluid flow indicator that provides a readily discernible visible indication of fluid flow through the apparatus. Additionally, the apparatus includes a novel adjustable flow rate control means for precisely adjustably controlling the rate of fluid flow from the reservoir of the device.

15 Claims, 37 Drawing Sheets

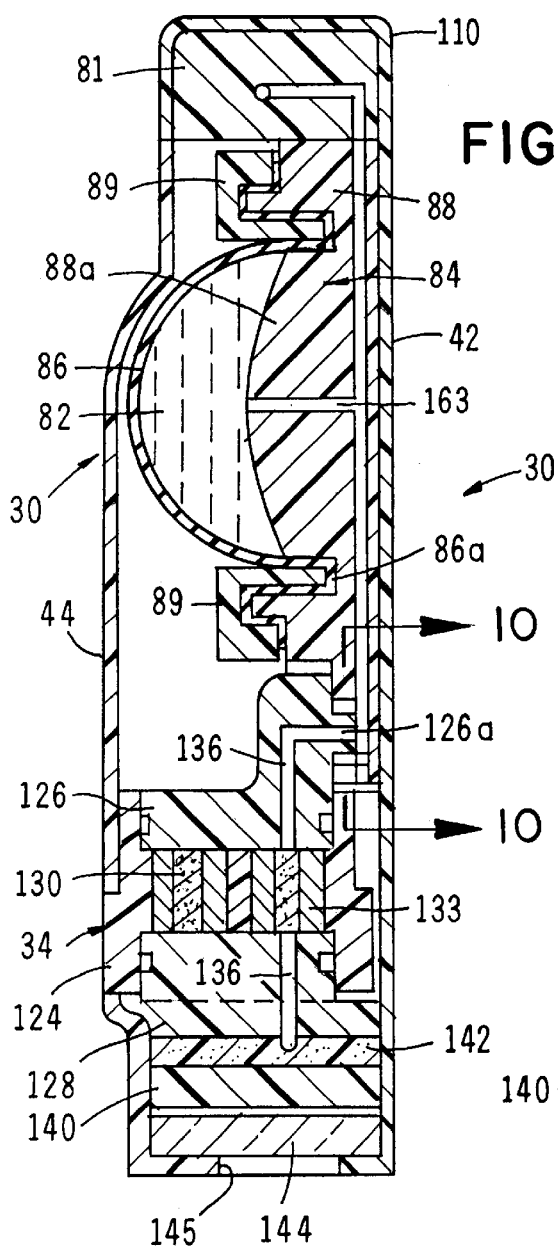
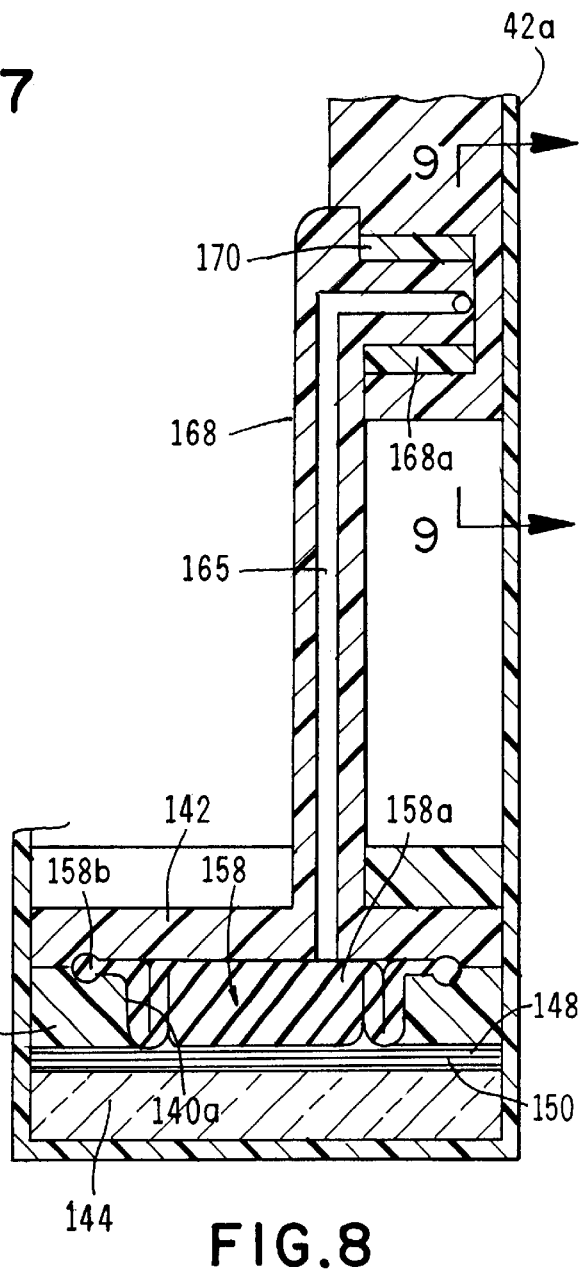
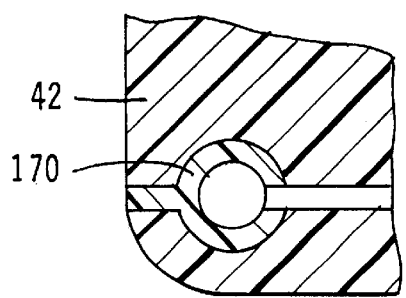
FIG.7
FIG.8
FIG.9

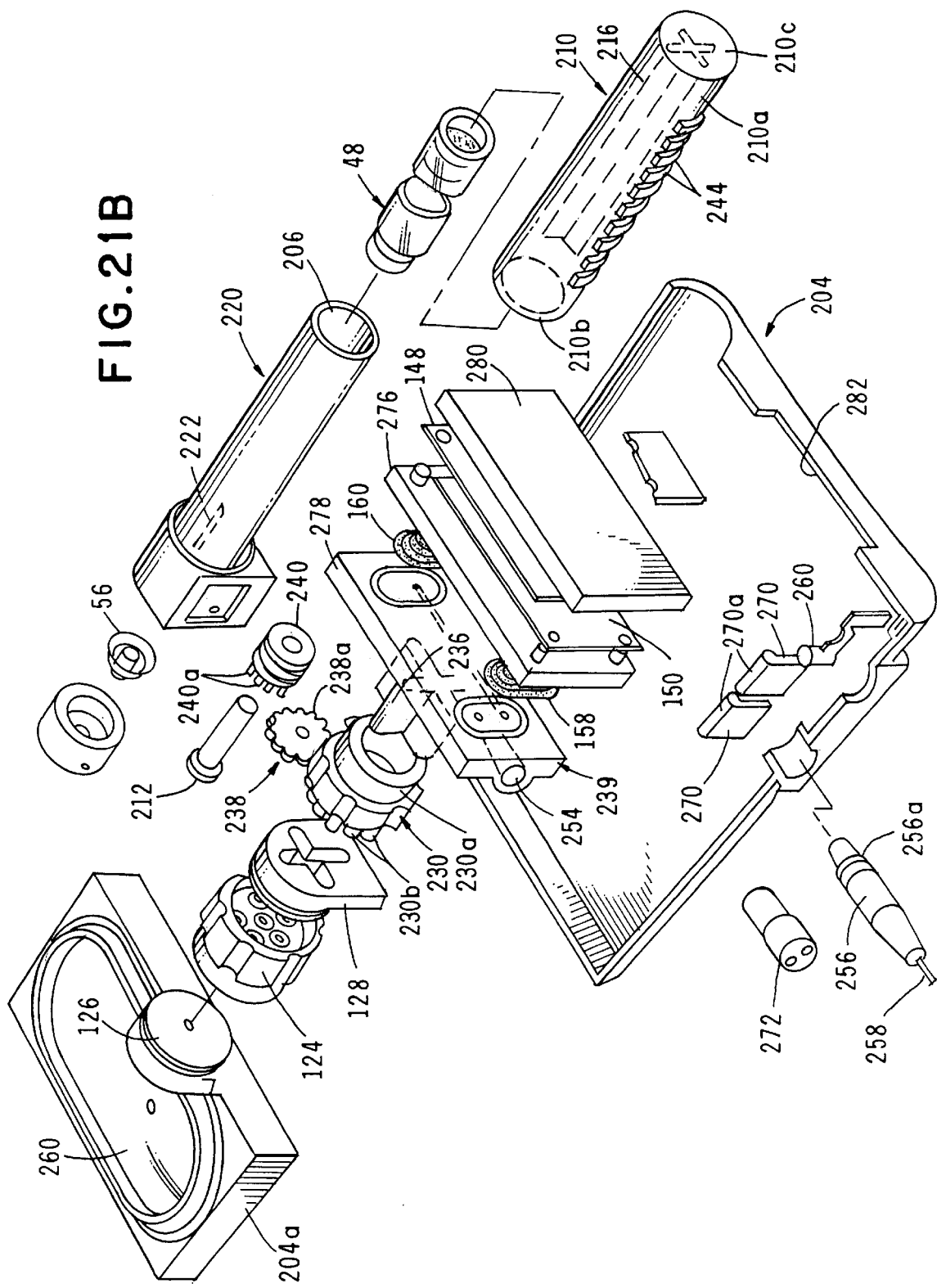

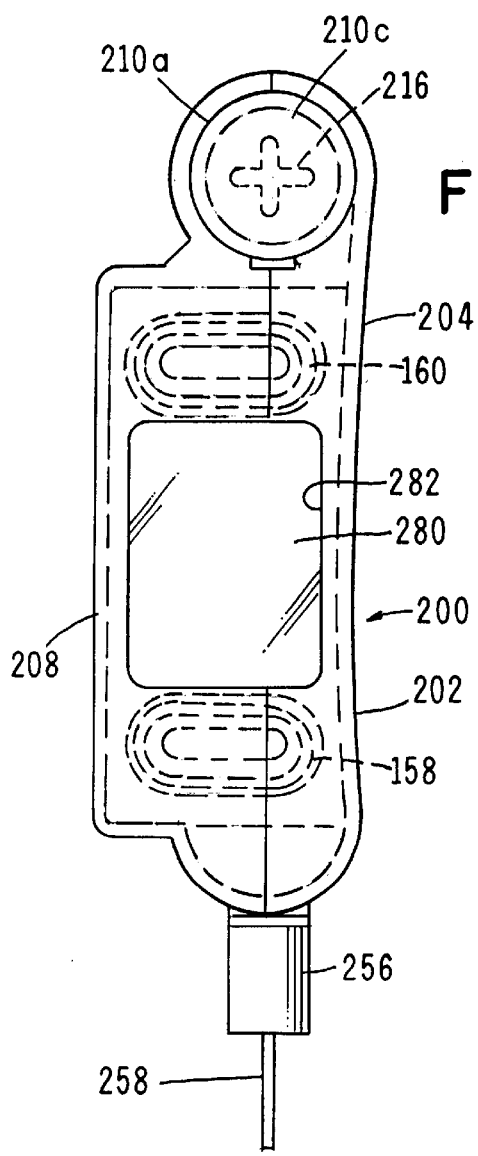
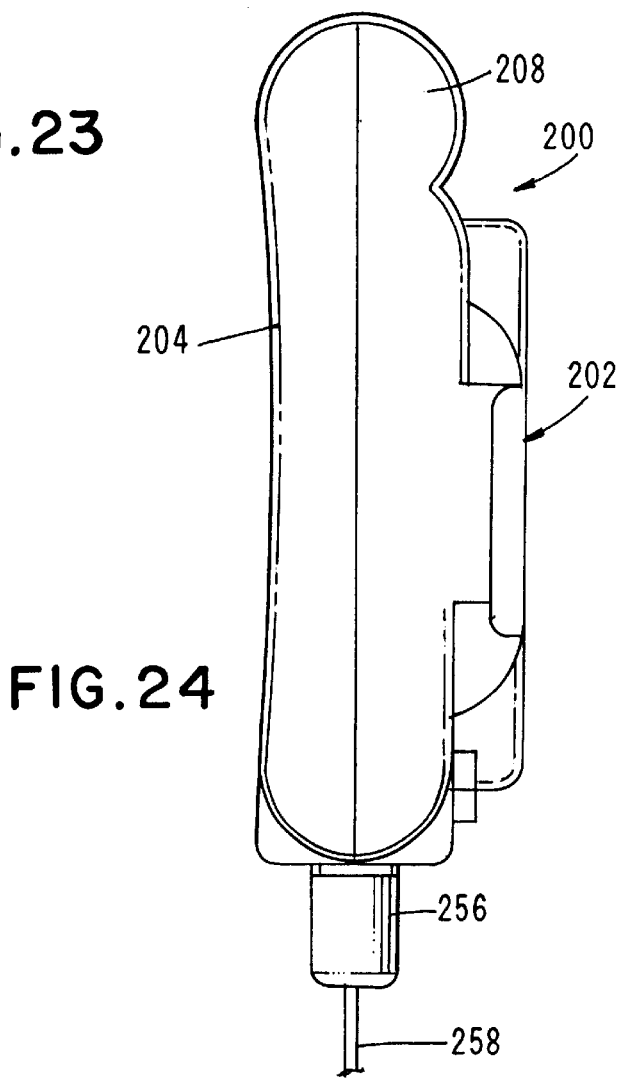
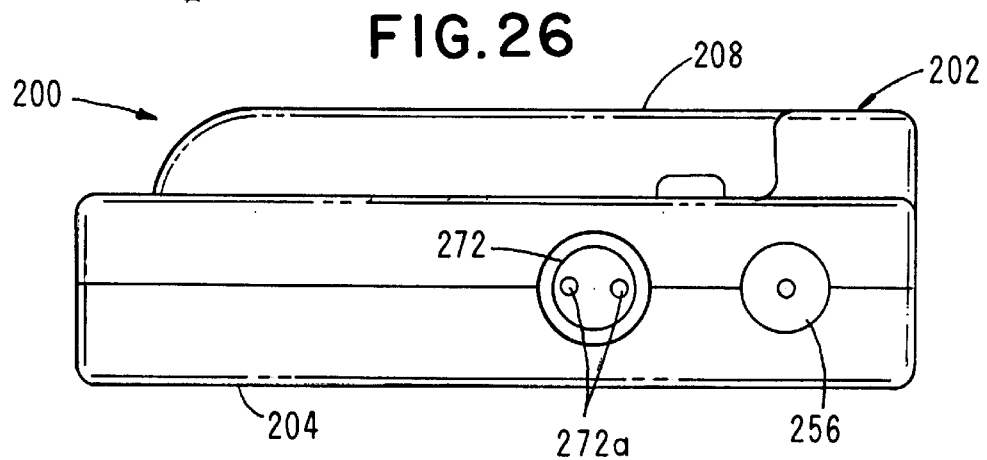

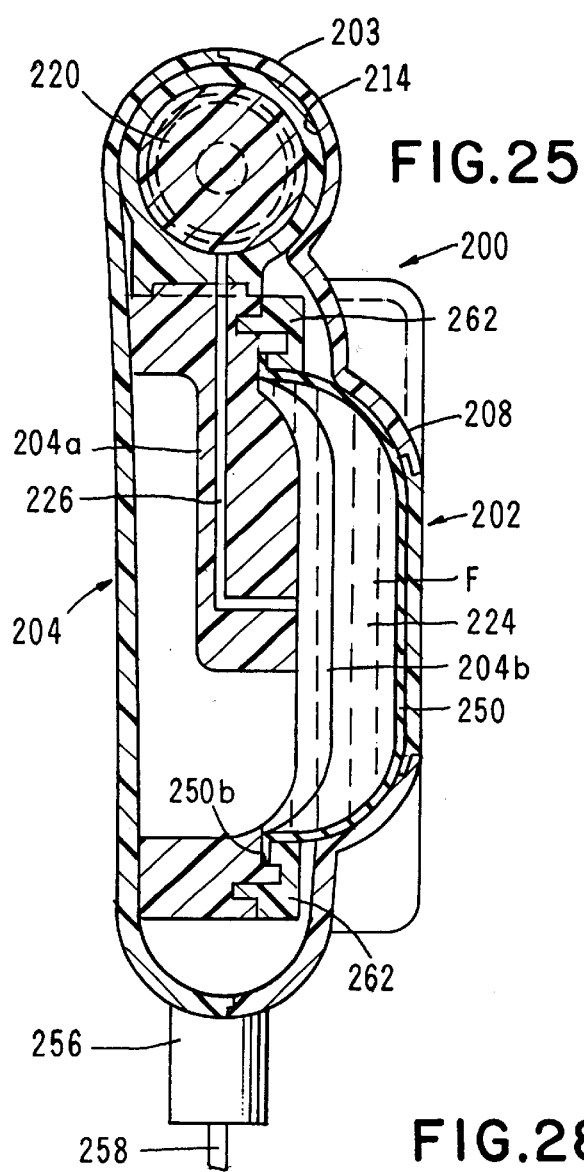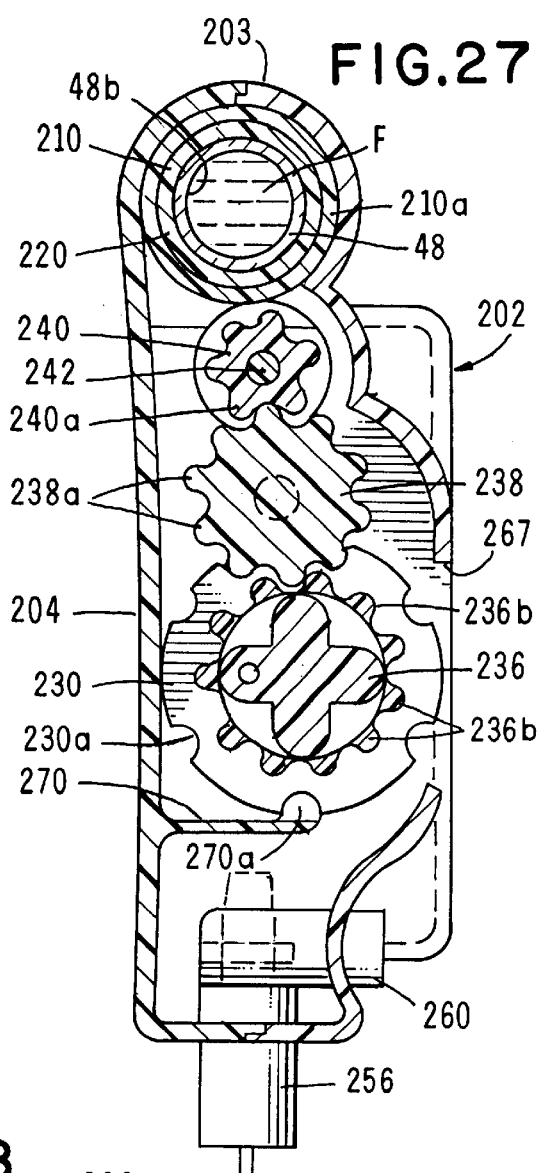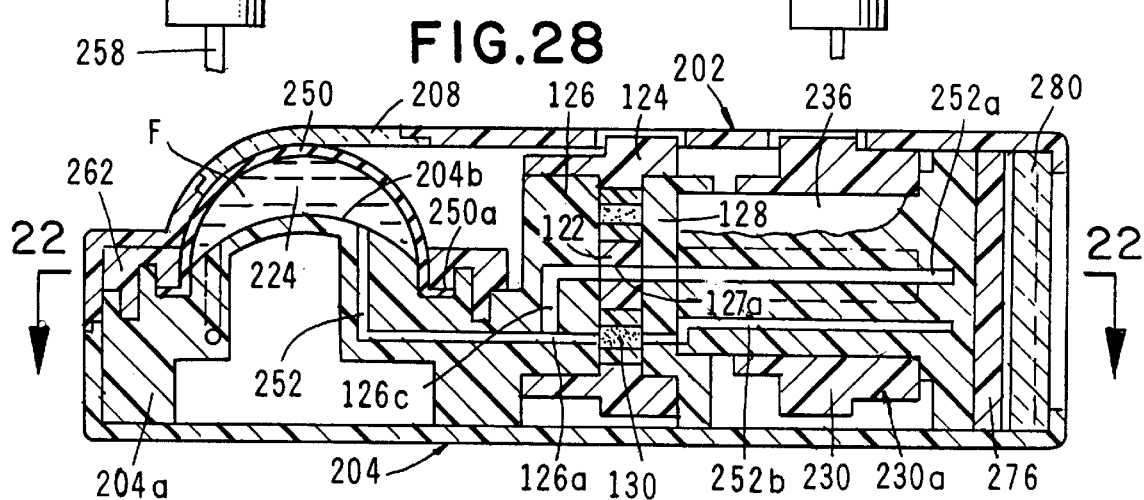

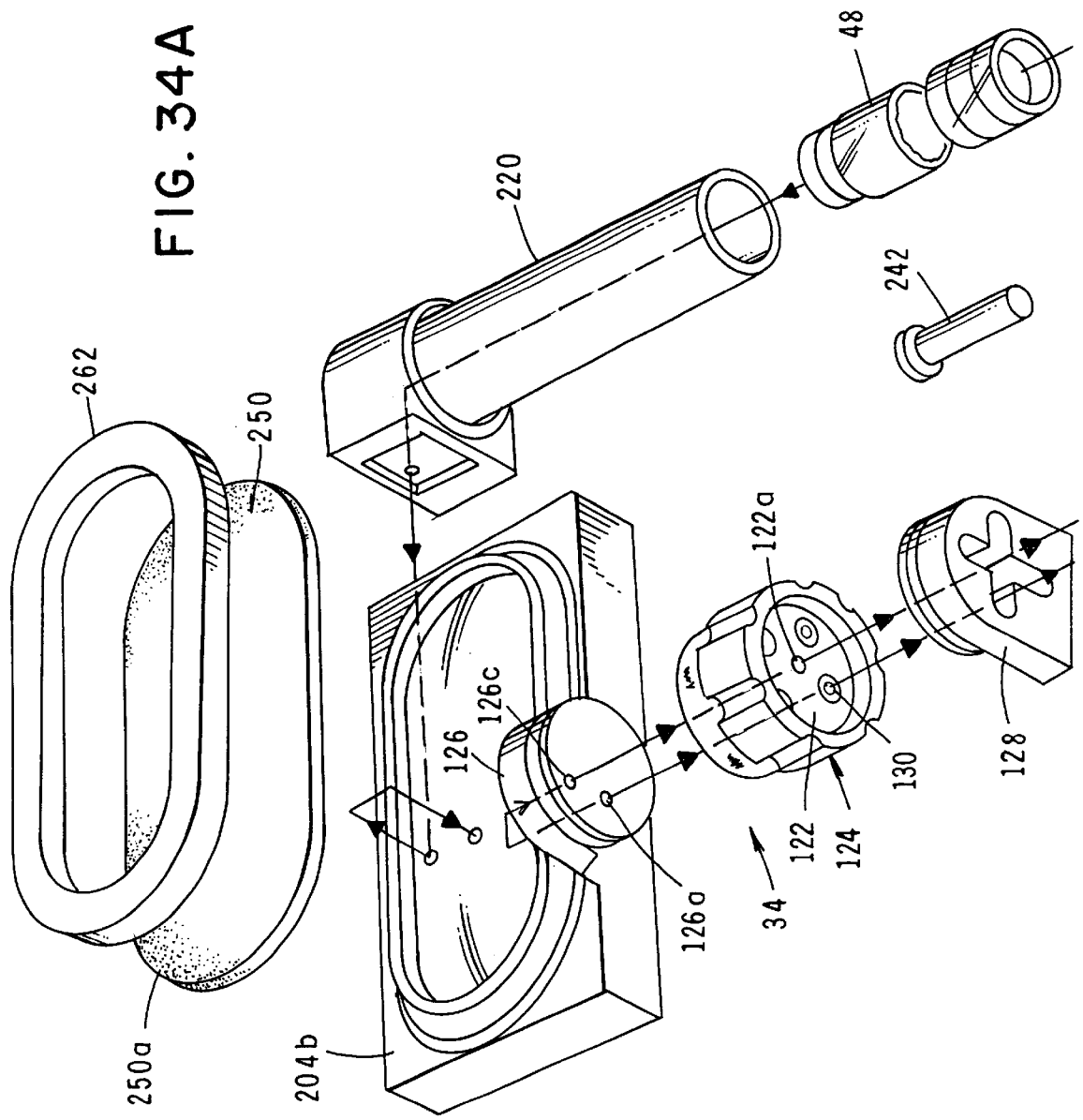

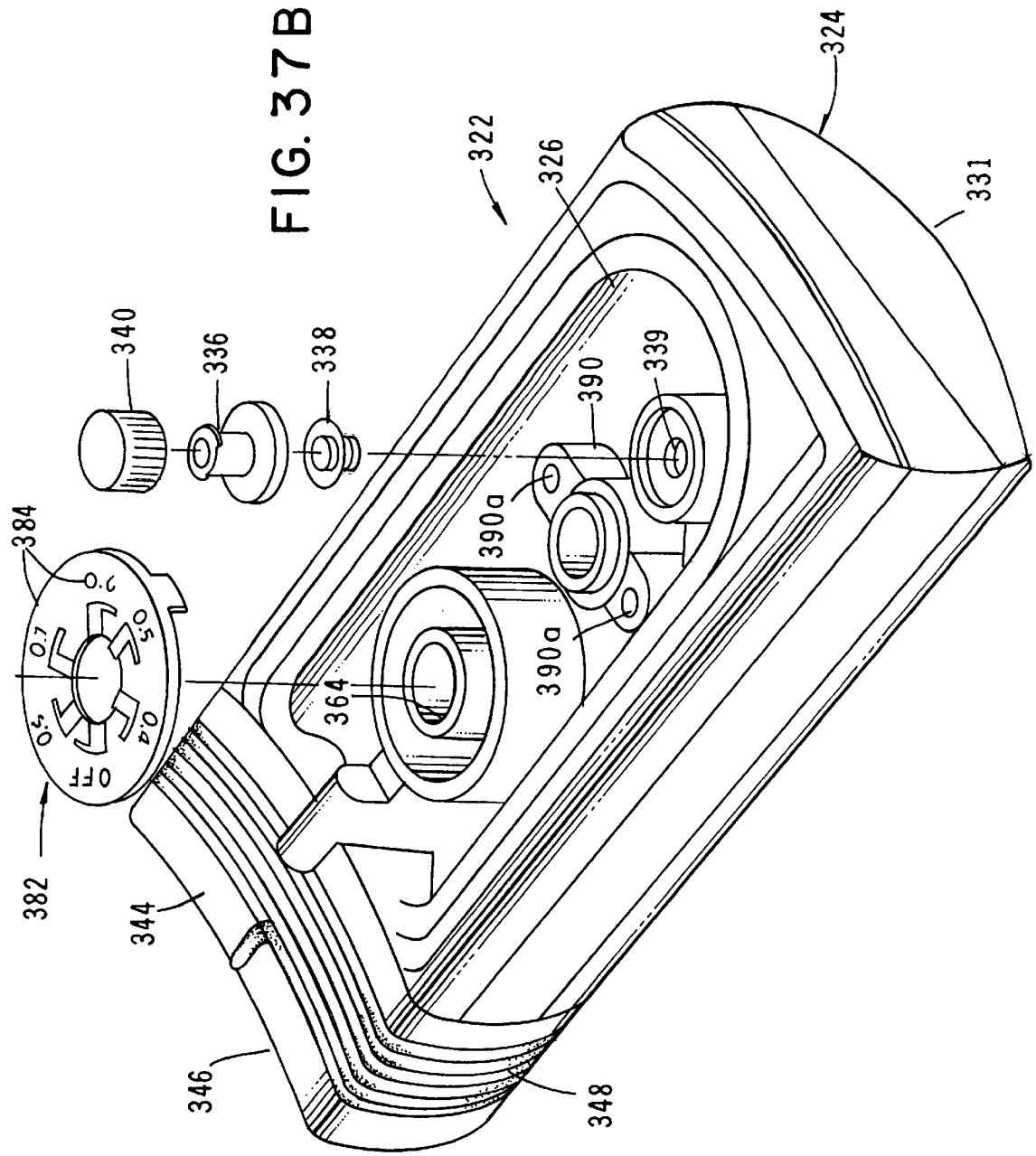

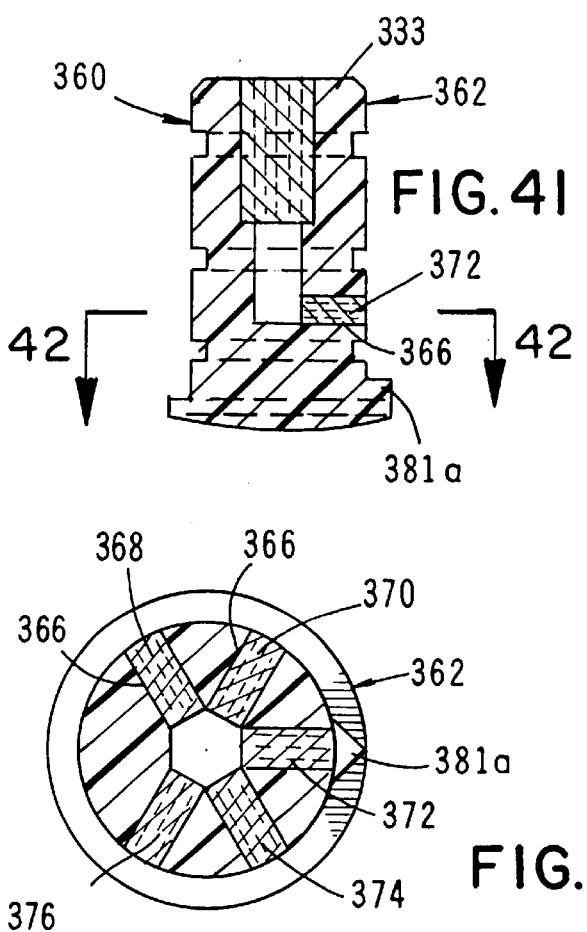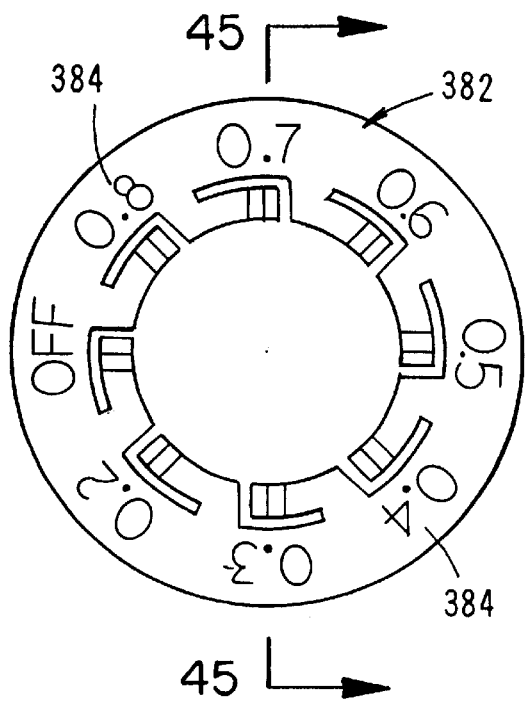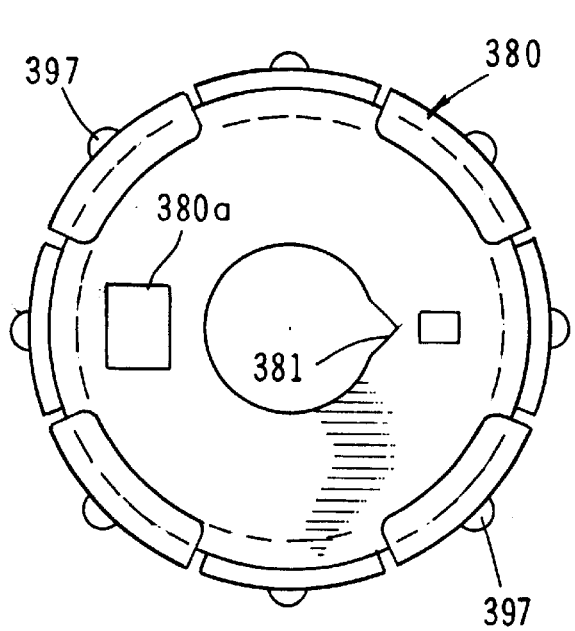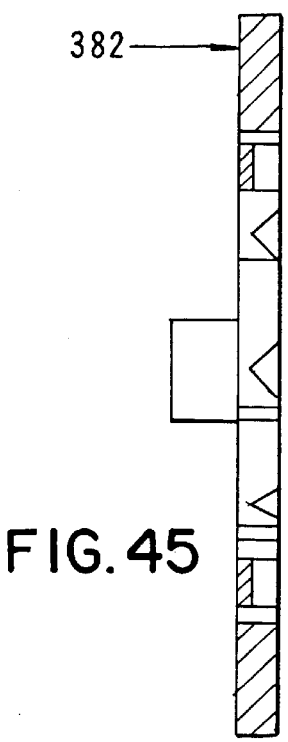
FIG. 41
FIG. 42
FIG. 43
FIG. 44
FIG. 45

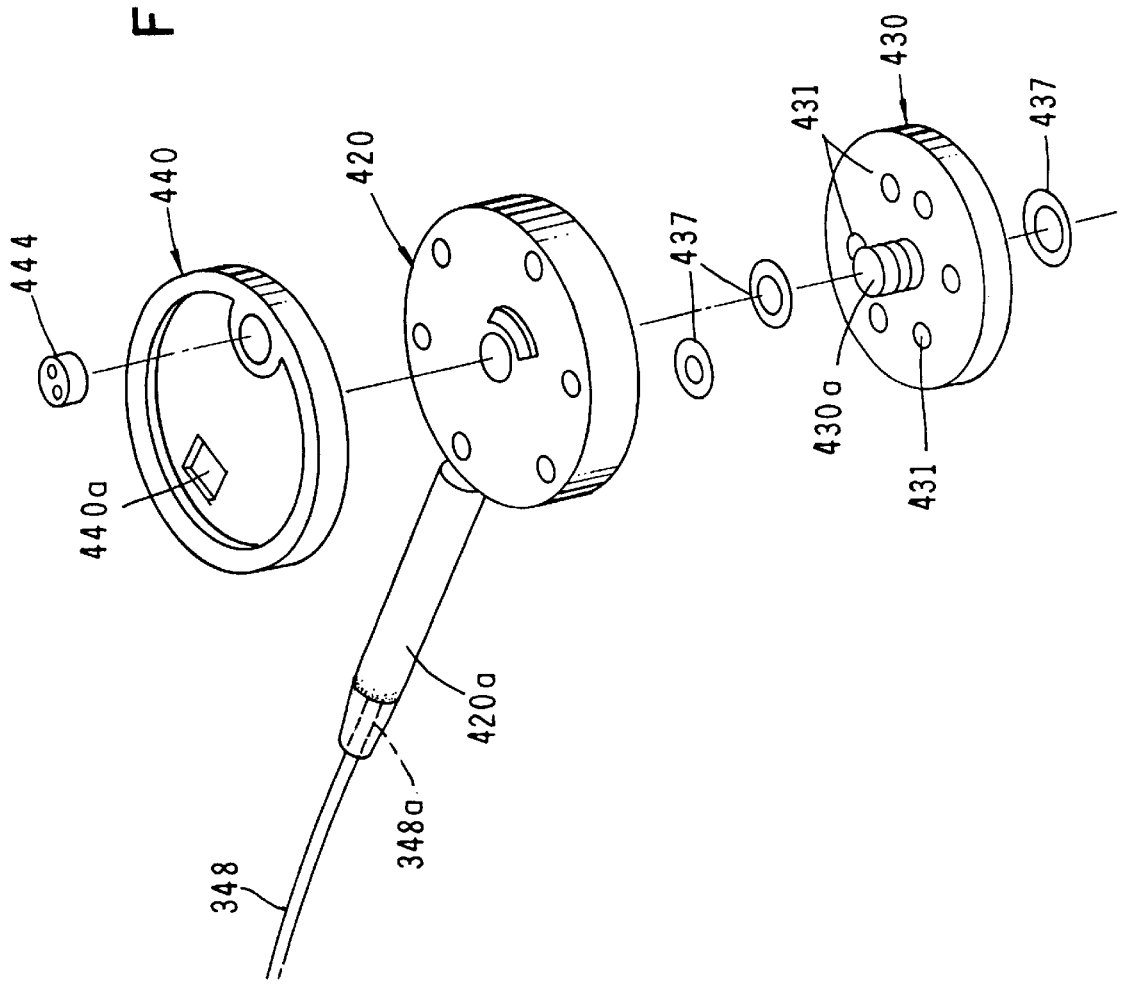

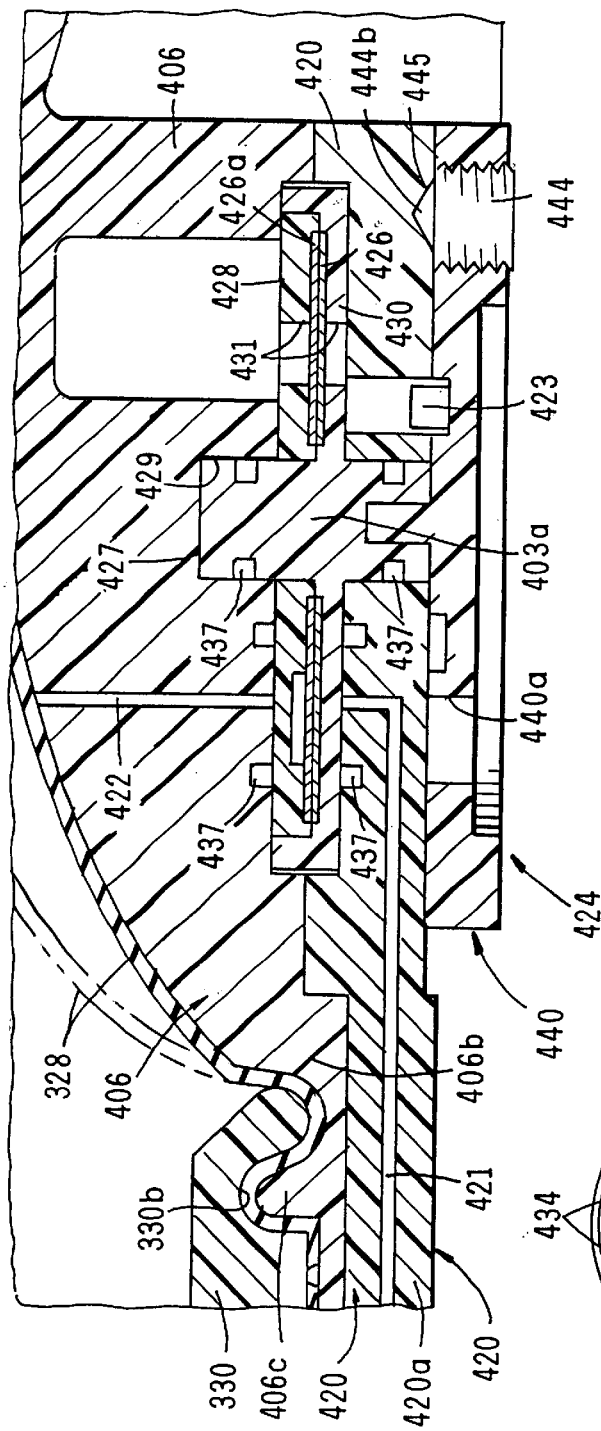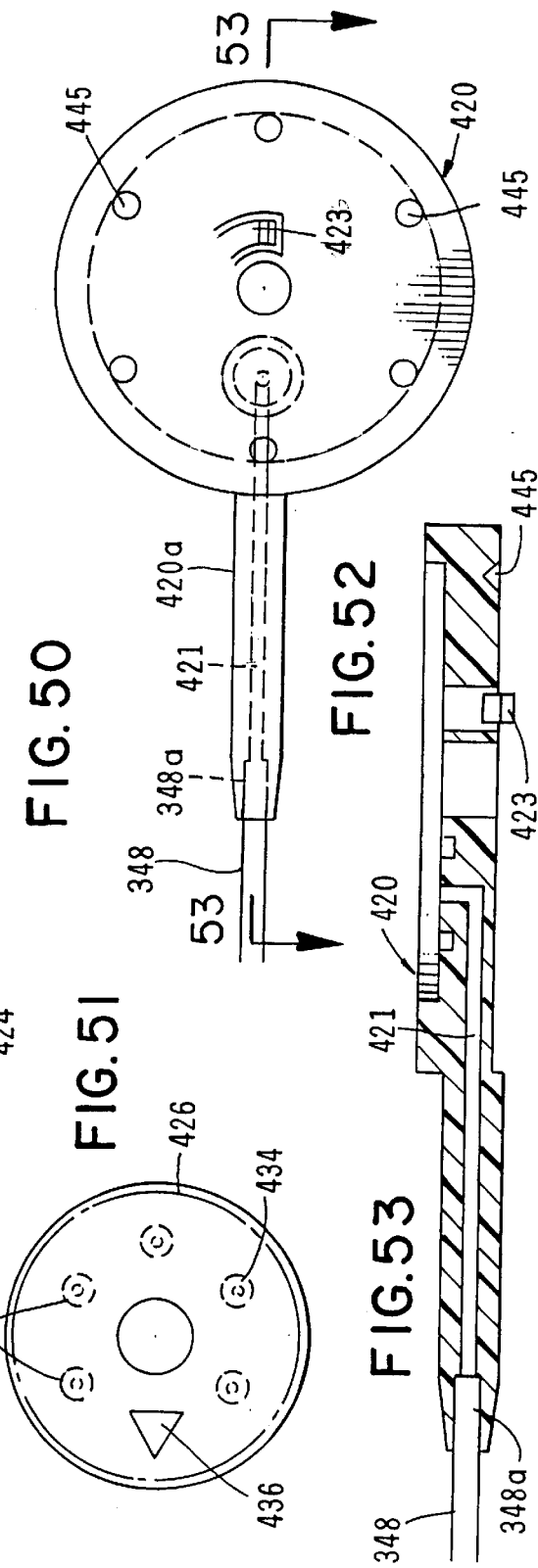
FIG.50
FIG.51
FIG.52
FIG.53

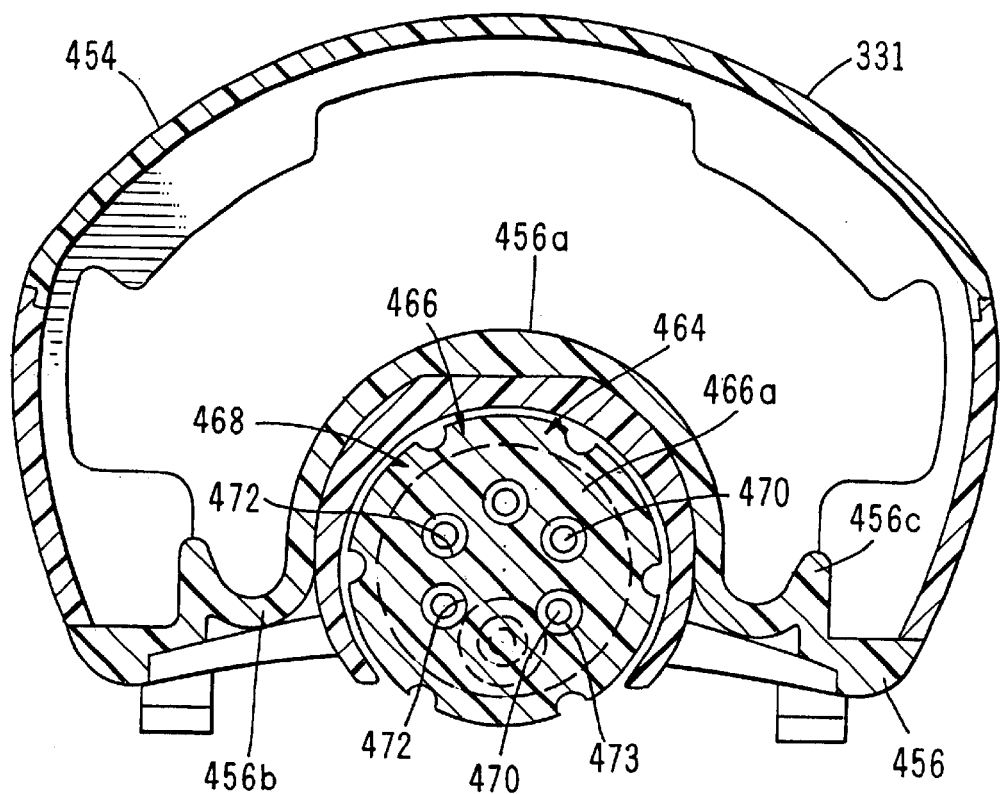
FIG. 57
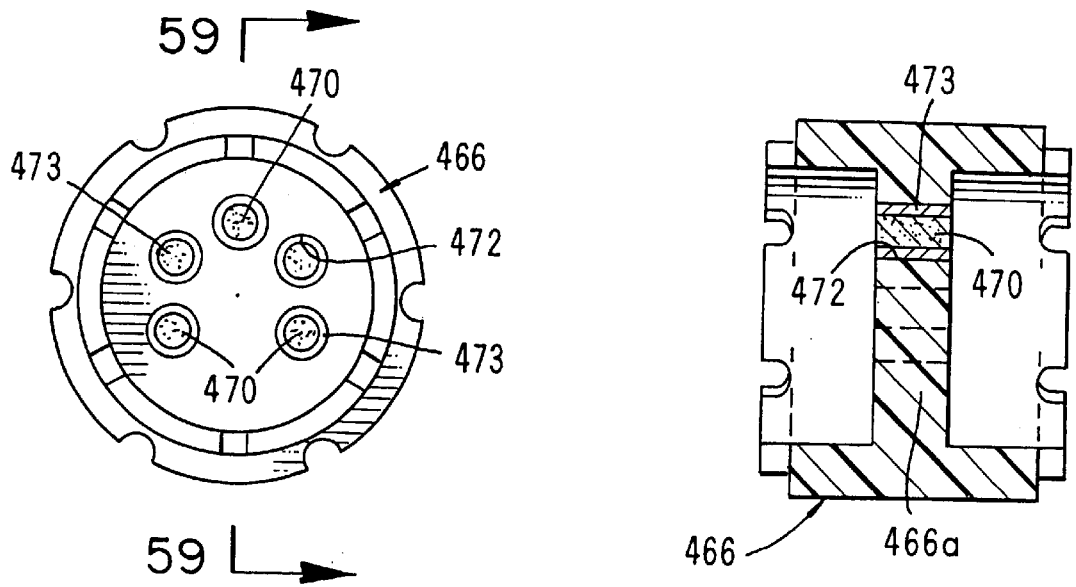
FIG. 58
FIG. 59

VARIABLE RATE INFUSION APPARATUS WITH INDICATOR AND ADJUSTABLE RATE CONTROL

SPECIFICATION

This is a Continuation-In-Part of U.S. application Ser. No. 09/165,713 filed Oct. 2, 1998 now U.S. Pat. No. 6,231,545, which is a Continuation-In-Part of Ser. No. 08/768,663 filed Dec. 18, 1996, now U.S. Pat. No. 5,840,071.

BACKGROUND OF THE INVENTION

1. Field of the Invention

The present invention relates generally to fluid delivery devices. More particularly, the invention concerns an improved apparatus for infusing medicinal agents into an ambulatory patient at specific rates over extended periods of time, which apparatus includes fluid flow indicator means and a novel adjustable flow rate control means for precisely adjustably controlling the rate of fluid flow from the reservoir of the device.

2. Discussion of the Prior Art

The biotechnology industry emerged in the 1980s as new molecular biological techniques made possible the commercial production of proteins, peptides and other biopharmaceuticals. These molecules are integral to numerous physiological processes and have enormous therapeutic potential as oncolytics, hormones, analgesics, antihypertensives, growth factors and others. It is believed that at the present time there are currently over 600 biotech drugs in advanced stages of development.

Because bioengineered molecules often have an extremely short biological half-life and poor bioavailability, continuous infusion is often considered to be a more economically and therapeutically practical route of drug delivery than oral, ocular, nasal, buccal, intestinal, rectal or pulmonary administration. As will be better appreciated from the discussion that follows, the apparatus of the present invention has been specifically engineered for these emerging therapies and will allow highly safe and accurate microscaled ambulatory infusion of drugs with narrow therapeutic windows. In one form of the invention, the apparatus will accept either 1.5 or 3.0 mL vial cartridges of injectable agent, consistent with the expected dosing requirements of many biopharmaceuticals now under development.

Many of the pharmacologic agents now under development possess a very narrow range of therapeutic effectiveness, for instance, too small a dose results in no effect, while too great a dose results in toxic reaction. Additionally, the ever increasing medicinal use of proteins and peptides has created many challenging new problems concerning means for the effective delivery of the molecules to the patient. In general these molecules are difficult to stabilize and often undergo a variety of physical and chemical transformations including precipitation, aggregation and oxidation. Further, they are poorly absorbed after oral administration. Most proteins now being used or under development are given parenterally in order to insure rapid onset of action, with the main routes of delivery being intravenous, intramuscular, or subcutaneous. Intravenous administration results in the fastest, intramuscular injection is next, and subcutaneous injection exhibits the slowest onset of action. While other noninvasive methods of delivery, such as iontophoresis and nasal or buccal administration have been investigated, they have not been widely adopted.

A major advantage of infusion therapy is the opportunity to avoid repeated injections and to achieve a constant or controlled rate of delivery of the medicinal agents. Accordingly, many types of sophisticated electronic infusion devices have been suggested to achieve complex patterns of dosing which are customized to the patient's need and do not require repeated injections in order to maintain a constant level of proteins in the blood. Another major advantage of infusion therapy over repeated needle injections resides in the fact that such therapy is less time consuming and considerably less costly because the caregiver can administer a single dose instead of multiple injections given over a period of time.

The primary disadvantage of infusion therapy is its limiting effect on the patient's lifestyle. This is largely due to the physical size of the prior art devices and the many precautions associated with parenteral therapy. Additionally, many of the prior art portable electromechanical devices are generally quite fragile and must be carefully handled to avoid breakage and preclude operational malfunction. Experience has shown that while a patient will tolerate restrictions on an active lifestyle for short periods of time, long-term use of the prior art devices have tended to create significant patient intolerance. In addition to the precautions associated with using the prior art devices, there are numerous logistical issues of battery changing and frequent replacement and the dedicated pump accessories. These logistical issues substantially contribute to the overall cost and complexity of prior art infusion therapy.

The unique combination of features in the apparatus of the present invention make it superior to virtually all currently existing competitive systems. For example, although stationary electronic syringe pumps offer an excellent flow rate accuracy of 3–10%, they are expensive, high maintenance devices and do not allow patient mobility. Recently, portable, miniaturized versions of these syringe pumps have been developed which allow greater freedom; however, they are often fragile, non-waterproof and complicated to use, requiring battery and accessory changes. Also problematic is the fact that both of the latter two types of devices often require drugs to be diluted for parenteral administration, which may lead to unnecessary patient overhydration. In addition to syringe systems, depot delivery (via subcutaneous or intramuscular implants) has been developed for continuous infusion; however, its high cost, invasiveness and inability to provide drug stability makes it an unattractive alternative to potential users.

Because the present application discloses improvements to the apparatus described in the U.S. Ser. No. 08/768,663, this co-pending application is also hereby incorporated by reference in its entirely as though fully set forth herein.

The elastomeric film materials used in the apparatus of the present invention, as well as various alternate constructions are described in detail in U.S. Pat. No. 5,205,820 issued to one of the present inventors. Therefore, U.S. Pat. No. 5,205,820 is also incorporated by reference in its entirety as though fully set forth herein.

As will be better appreciated from the discussion that follows, the apparatus of the invention can be used with minimal professional assistance in an alternate health care environment, such as the home. By way of example, the completely mechanical devices of the invention can be comfortably and conveniently removably affixed to the patient's body and can be used for continuous infusion of various medicinal agents over substantial periods of time.

Because the present invention comprises an improvement over the embodiments of the invention described in Ser. No.

08/768,663, this latter application is incorporated herein by reference as though fully set for the herein. While the inventions described in Ser. No. 08/768,663 comprise fluid delivery devices having a fluid reservoir and an indicator assembly for indicating fluid flow through the apparatus they do not include the highly novel, adjustable fluid flow rate mechanism of the present invention which enables the fluid contained within the reservoir of the device to be precisely dispensed at various selected rates. As will be better understood from the description which follows, the novel adjustable fluid flow rate control mechanism of the present invention also includes novel locking means for preventing unauthorized adjustment of the rate control mechanism. This novel locking means is operable only by a physician or health care worker who is in possession of a physician operating key. Accordingly, once a particular flow rate is selected, the patient cannot unilaterally change the flow rate.

SUMMARY OF THE INVENTION

It is an object of the present invention to provide an apparatus for expelling fluids at a precisely controlled rate that is of a compact laminate construction. More particularly, it is an object of the invention to provide such an apparatus that can be used for the precise infusion of pharmaceutical agents, including proteins and peptides into an ambulatory patient at controlled rates over extended periods of time.

It is an object of the present invention to provide an apparatus of the aforementioned character which is highly reliable and easy-to-use by lay persons in a non-hospital environment.

Another object of the invention is to provide an apparatus which can be factory prefilled with a wide variety of medicaments or one which can readily be filled in the field shortly prior to use.

A further object of the invention is to provide a low profile, fluid delivery device of laminate construction which can be manufactured inexpensively in large volume by automated machinery.

Another object of the invention is to provide a device of the aforementioned character which includes novel fluid flow control means that are disposed intermediate the fluid reservoir outlet and the outlet port of the device for precisely controlling the flow of fluid flow from the outlet port toward the patient.

Another object of the invention is to provide an apparatus of the aforementioned character in which the fluid flow control means comprises rate control means that includes a rotatable flow restrictor support disk that can be rotated by the treating physician to selectively position the flow restrictor between the fluid reservoir and the device outlet port so as to precisely control the rate of flow of beneficial agents from the fluid reservoir toward the patient.

Another object of the present invention is to provide a flow rate control means of the type described in the preceding paragraph in which the flow restrictors comprise porous frits of varying porosity.

Another object of the present invention is to provide a flow rate control means in which the flow restrictors comprise a laser drilled thin film.

Another object of the invention is to provide an apparatus as described in the preceding paragraphs which includes locking means for locking the variable flow rate control means in a preset position so that the rate control can be set only by the treating physician or an authorized health care worker having an operating key.

Another object of the invention is to provide an apparatus of the aforementioned character in which the stored energy source is of a novel construction that can be precisely tailored to continuously deliver fluid from the device to the patient Another object of the invention is to provide fill means for use in controllably filling the fluid reservoir of the apparatus.

Another object of the invention is to provide a novel vial assembly for use with the fluid dispenser subassembly of the apparatus which is easy to use, is inexpensive to manufacture, and one which maintains the vial in an aseptic condition until time of use.

Other objects of the invention are set forth in U.S. Pat. No. 5,205,820 which is incorporated herein and still further objects will become more apparent from the discussion which follows.

By way of summary, the fluid delivery apparatus of the present form of the invention comprises two cooperating components, namely a fluid dispenser and a novel, adjustable fluid flow control assembly for selecting the desired fluid flow rate to the patient. The fluid dispenser, which readily lends itself to automated manufacture, is generally similar to that described in copending Ser. No. 09/165,713, which application is incorporated herein by reference and includes a base and a stored energy means comprising at least one distendable elastomeric membrane which cooperates with the base to form a fluid reservoir. In at least one form of the invention, the fluid dispenser includes a novel infusion means that can be conveniently stored in a forward compartment of the device housing.

BRIEF DESCRIPTION OF THE DRAWINGS

FIG. 7 is a cross-sectional view taken along lines 7—7 of FIG. 5.

FIG. 8 is an enlarged, cross-sectional view taken along lines 8—8 of FIG. 5.

FIG. 9 is a cross-sectional view taken along lines 9—9 of FIG. 8.

FIGS. 21A and 21B, when considered together, comprise a generally perspective exploded view of the infusion device shown in FIG. 20.

FIG. 23 is a front view of the apparatus shown in FIG. 20.

FIG. 24 is a rear view of the apparatus shown in FIG. 20.

FIG. 25 is a cross-sectional view taken along lines 25—25 of FIG. 22.

FIG. 26 is a left side view of the apparatus shown in FIG. 1

FIG. 27 is a cross-sectional view taken along lines 27—27 of FIG. 22.

FIG. 28 is a cross-sectional view taken along lines 28—28 of FIG. 22.

FIGS. 34A and 34B, when considered together, comprise a generally perspective exploded view similar to FIG. 21 and showing the fluid flow paths through the device.

FIGS. 37A and 37B, when considered together, comprise a generally perspective, exploded bottom view of the fluid dispenser shown in FIG. 35.

FIG. 41 is a cross-sectional view of the control shaft of the device.

FIG. 42 is a view taken along lines 42—42 of FIG. 41.

FIG. 43 is a top plan view of the rate control selector wheel of the device of this latest form of the invention.

FIG. 44 is a top plan view of the indicator disk of the device which carries flow rate indicia.

FIG. 45 is a cross-sectional view taken along lines 45—45 of FIG. 44.

FIGS. 48A and 48B, when considered together, comprise a generally perspective, exploded bottom view of the fluid dispenser shown in FIG. 46.

FIG. 50 is an enlarged, cross-sectional view of the area designated in FIG. 49 by the numeral 50.

FIG. 51 is a top plan view of the rate control film of the device shown in FIG. 50.

FIG. 52 is a top plan view of the rate control housing of the device.

FIG. 53 is a cross-sectional view taken along lines 53—53 of FIG. 52.

FIG. 57 is a view taken along lines 57—57 of FIG. 56.

FIG. 58 is a cross-sectional view of a portion of the control assembly of the device shown in FIG. 57.

FIG. 59 is a view taken along lines 59—59 of FIG. 58.

DISCUSSION OF THE INVENTION

Figure 1:
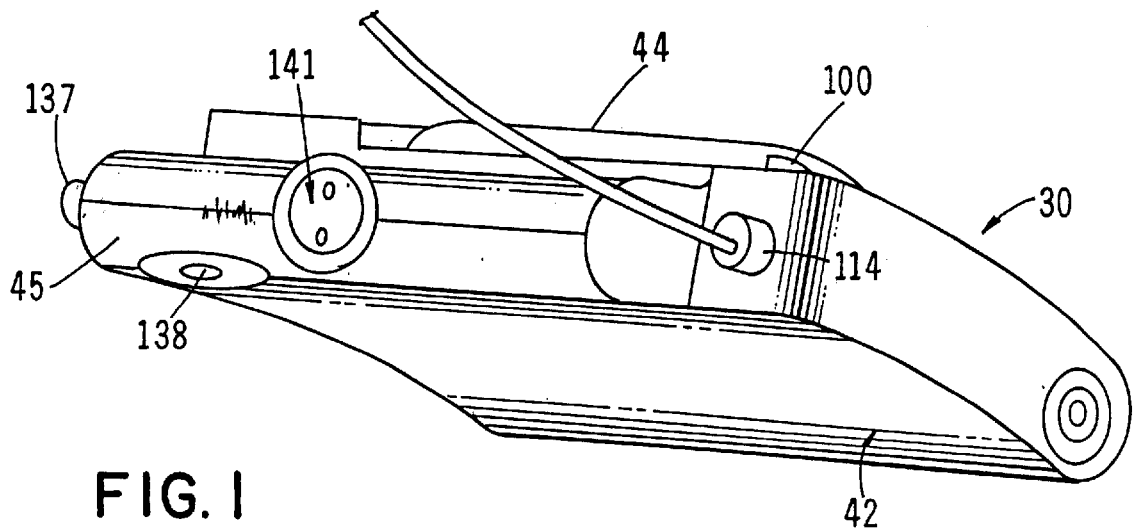
FIG. 1 is a generally perspective bottom view of one form of the infusion device of the present invention.

Referring to the drawings and particularly to FIGS. 1 through 7, one form of the apparatus of the invention for controlled delivery of medicinal fluid flow to a patient is there shown. The apparatus here comprises four major components which are generally designated in FIG. 2 as a hollow housing 30, a fill assembly 32, an adjustable flow rate mechanism 34 and an indicator assembly 36 for indicating fluid flow to the patient. Housing 30 of the apparatus is similar in some respects to that described in U.S. Pat. No. 5,721,382 in that it includes a base assembly 42, a stored energy means which cooperates with the base assembly to form a fluid reservoir and an indicator assembly which provides a visual indication of fluid flow through the device. Because of the pertinence of U.S. Pat. No. 5,721,382, this patent is incorporated by reference as though fully set forth herein. Also generally pertinent to a complete understanding of the present invention is the apparatus disclosed in co-pending U.S. application Ser. No. 08/768,663 filed on Dec. 18, 1996. This application is also incorporated by reference as though fully set forth herein.

Figure 4:
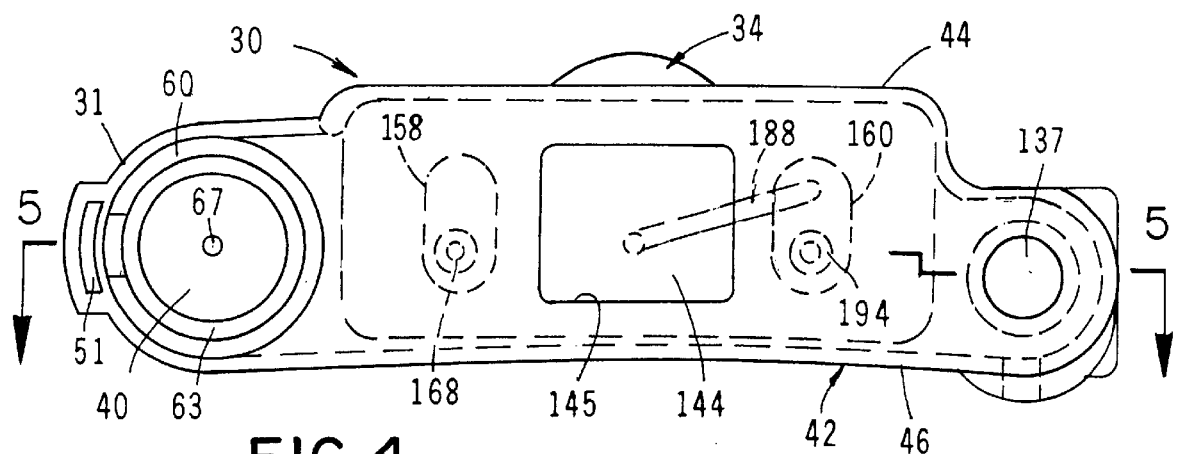
FIG. 4 is a front elevational view of the apparatus of the invention.
Figure 17A:
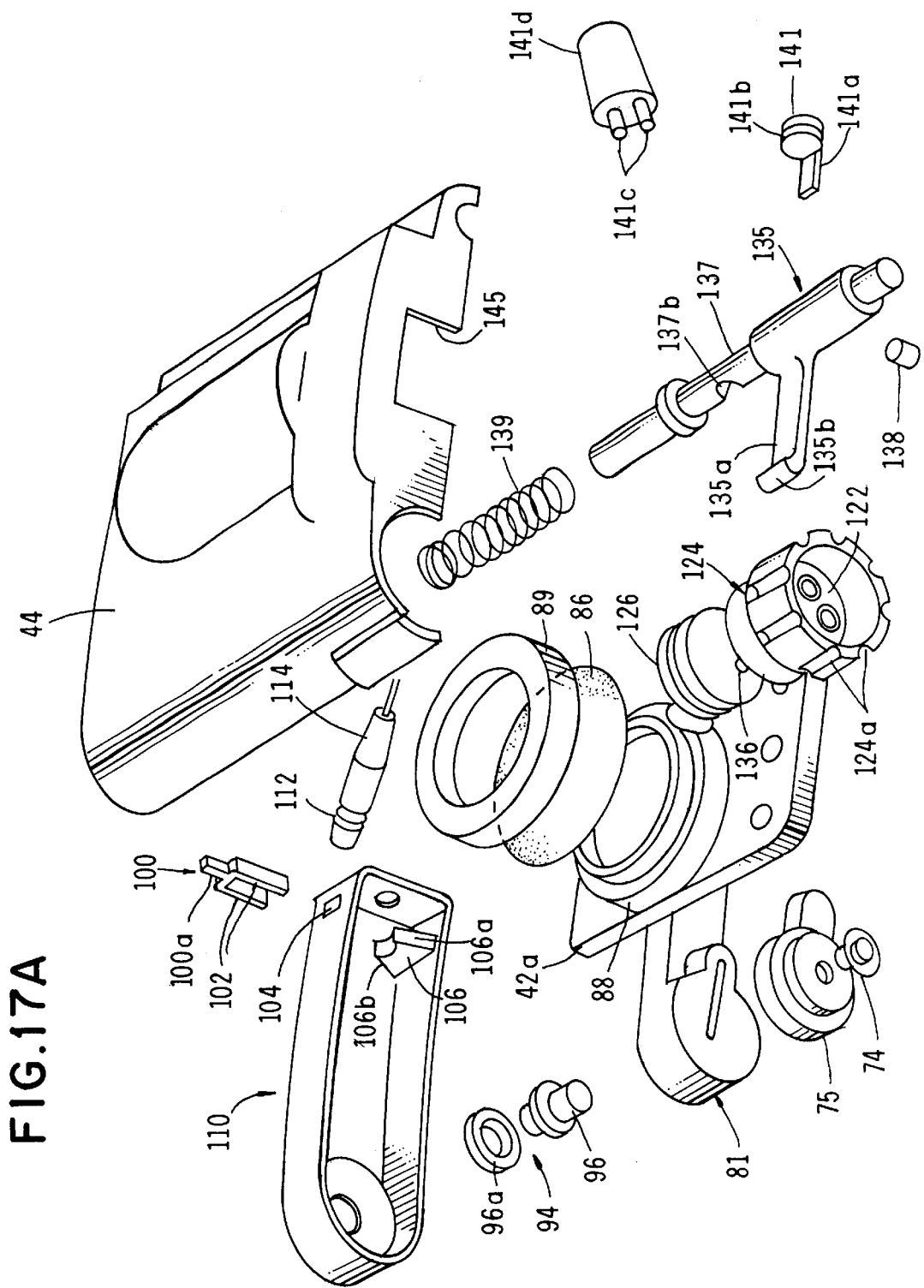
FIGS. 17A and 17B, when considered together, comprise a generally perspective exploded view of the apparatus of the present form of the invention showing the appearance and interrelationship among the various component parts of the apparatus.

Considering first the hollow housing assembly 30, this assembly is provided with a uniquely configured receiving chamber 40 which is formed between the base assembly 42 and an interconnected cover component 44 (FIGS. 4 and 17). Base assembly 42 and cover component 44, when interconnected, cooperate to define hollow housing assembly 30. In a manner presently to be described, chamber 40 is adapted to telescopically receive the fill assembly of the invention to permit controlled filling of the reservoir of the device with a fluid to be dispensed to the patient.

Figure 17B:
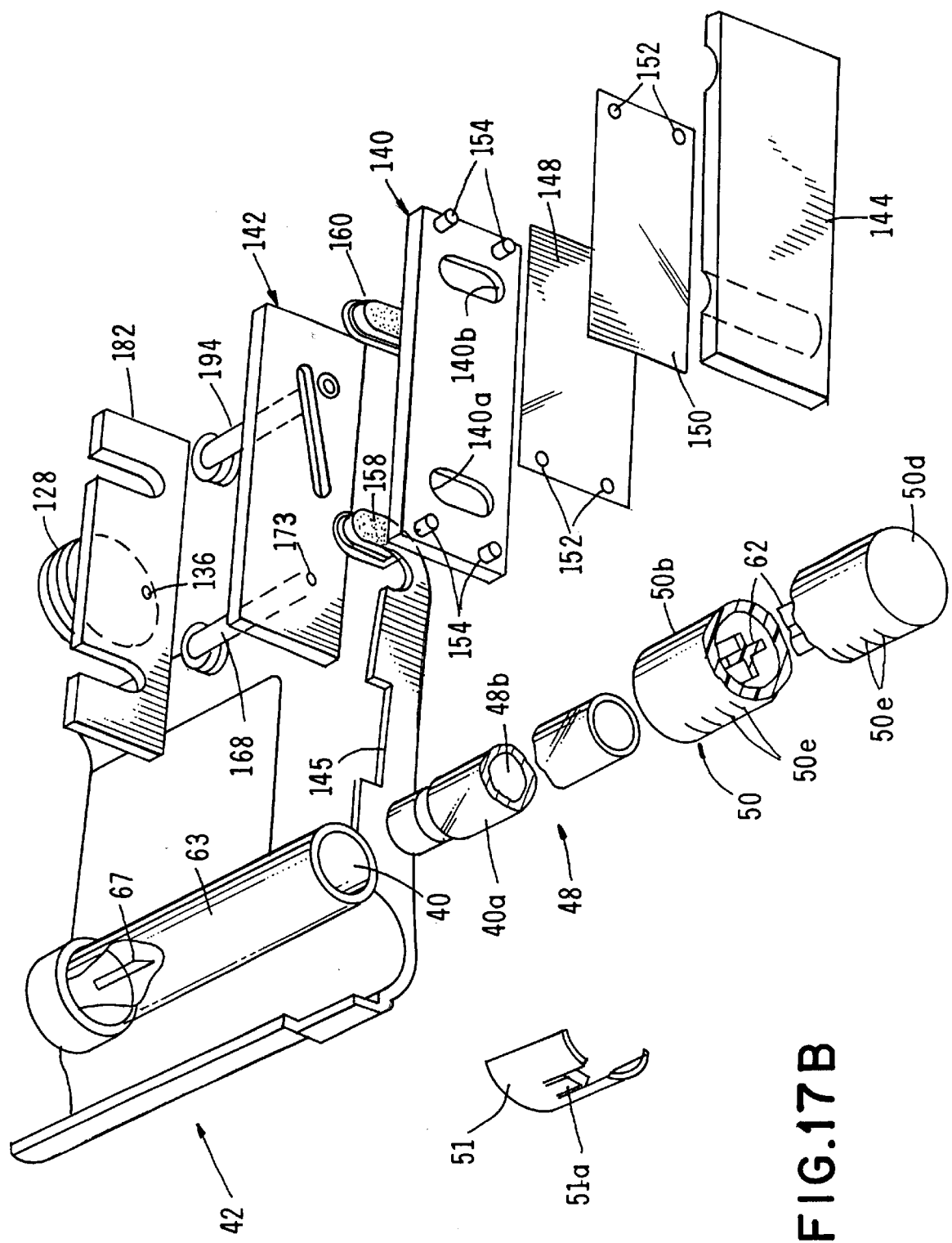
Figure 19:
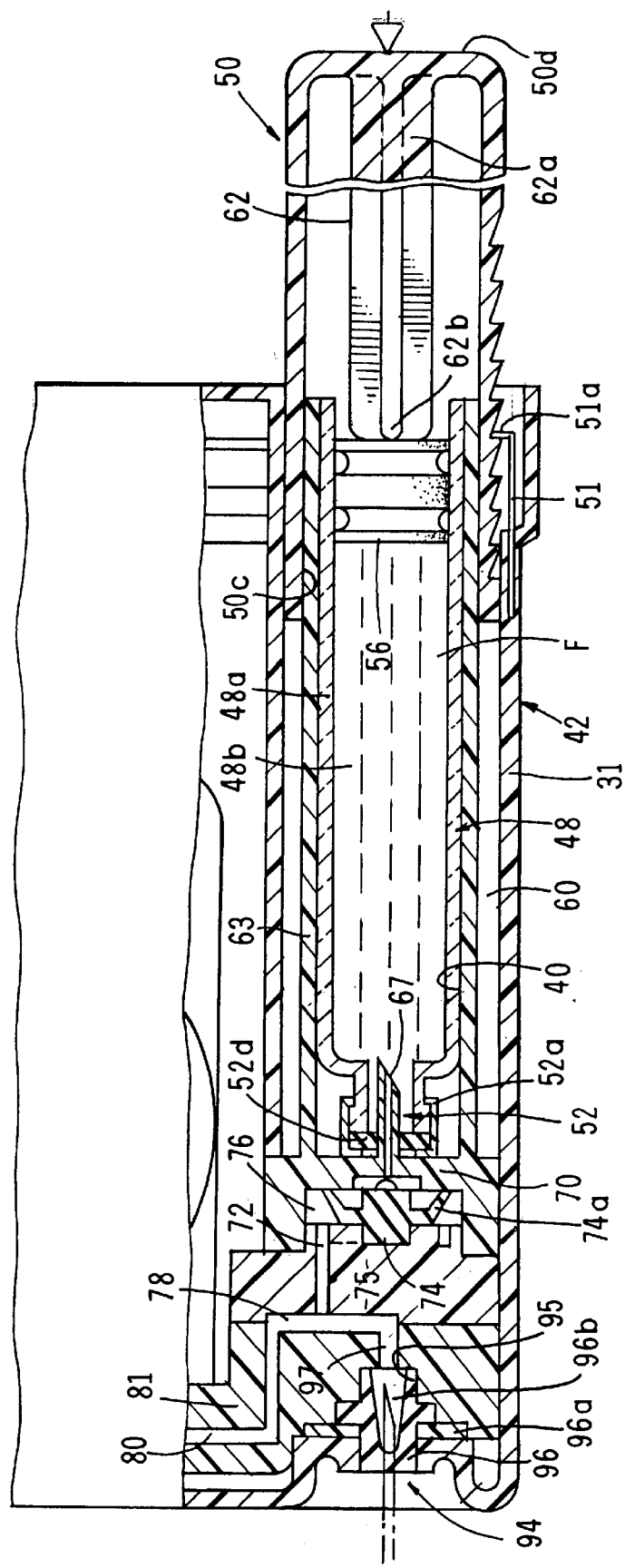
FIG. 19 is a cross-sectional view illustrating the manner of assembly of the fill vial of the apparatus with the housing.

Turning particularly to FIGS. 17 and 19, the fill assembly portion of the apparatus can be seen to comprise a container subassembly 48 and an adapter subassembly 50, the character of which will presently be described. Container assembly 48 includes a body portion 48a having a fluid chamber 48b for containing an injectable fluid "F". Chamber 48b is provided with first and second open ends, one of which is sealably closed by closure means here provided in the form of a pierceable septum assembly 52. Septum assembly 52 is held securely in position by a clamping ring 52a (FIG. 19). As best seen in FIG. 19, a plunger 56 is telescopically movable within chamber 48b of container assembly 48 between first and second locations. As is also shown in FIG. 19 subassembly 50 comprises a hollow housing 50b having a first open end 50c and a second closed end 50d. The adapter assembly 50 is telescopically receivable within an elongated, generally annular passageway 60 formed in device housing 30 in the manner shown in FIG. 19 so that the adapter assembly can be moved from a first extended position into a second vial encapsulation position. The adapter subassembly also includes pusher means shown here as an elongated pusher rod 62 which functions to move plunger 56 within the fluid chamber 48b of the container subassembly. Pusher rod 62 has a first end 62a which is interconnected with closure wall 50d and an opposite end 62b which engages plunger 56 and causes telescopic movement of the plunger forwardly within chamber 48b. Housing 50b includes a plurality of spaced-apart teeth 50e which are lockably engaged by a locking tab 51a provided on a locking clip 51 (FIG. 17B) which is carried by base 42. Those components, which comprise the adapter locking means, cooperate to lock the adapter against removal after it has been fully inserted into the housing.

Figure 6:
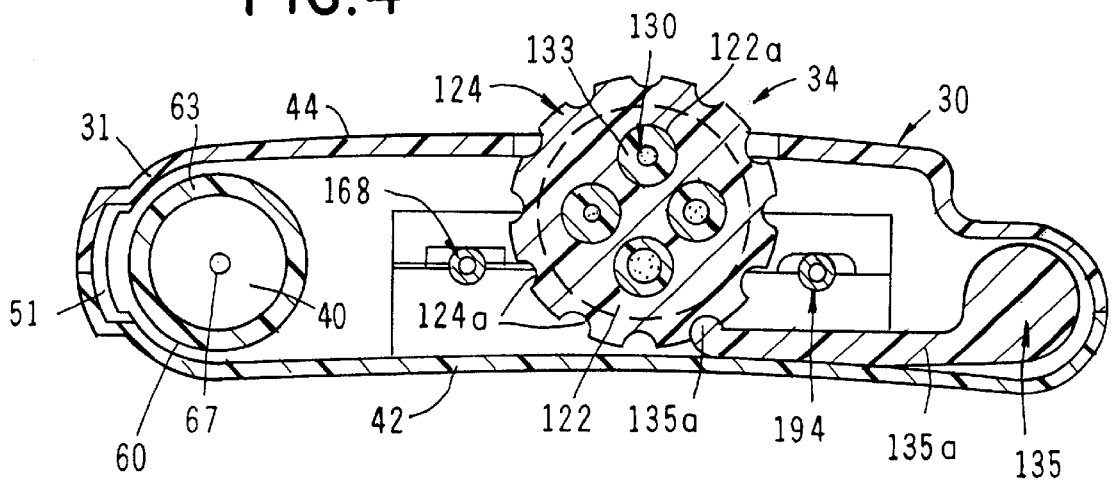
FIG. 6 is a cross-sectional view taken along lines 6—6 of FIG. 5

As best seen in FIG. 19, provided within housing 30 is an elongated, generally cylindrically shaped wall 63 which is concentric with the outer housing wall which defines receiving chamber 40. Wall 63 is radially spaced from the outer wall 31 of the housing so as to define the longitudinally extending annular space 60 (FIGS. 6 and 19). With this construction, during the mating of the reservoir fill assembly with the base assembly, the outer wall of the housing 50 is closely received within space 60 as the adapter subassembly is urged inwardly or forwardly of the device housing 30. At the same time that hollow housing 50 moves forwardly of annular space 60, the container assembly telescopically moves inwardly so as to move septum 52d of septum assembly 52 into piercing engagement with a hollow cannula 67 which is connected to a base wall 70 so that it extends inwardly into chamber 40 (see FIG. 5).

As plunger 56 of the container assembly is moved forwardly of container 48a by pusher rod 62, the fluid contained within the container will flow under pressure into a passageway 72 via a hollow cannula 67 and via a valve means, shown here as an umbrella type check valve 74. Check valve 74 is disposed within a cavity 76 formed in housing 30 in the manner shown in FIG. 5. Valve 74 is constructed from an appropriate elastomer and has a resiliently deformable skirt portion 74a which will deform inwardly within cavity 76 to permit fluid flow toward the reservoir of the device, but will block reverse flow. From passageway 72, the fluid will flow into a passageway 78, then into passageway 80 formed in a manifold 81, and finally into reservoir 82 via a passageway 84. As a fluid flows into reservoir 82 it will cause the stored energy means or membrane 86 (FIG. 7) to extend outwardly from an ullage substrate 88a formed in a base platform 88 which comprises a part of the base assembly 42 (FIG. 7). As best seen in FIG. 7, ullage substrate 88a is specially configured to receive a membrane clamping ring 89 which mates with ullage substrate 88a in a manner shown in FIG. 7 to clamp membrane 86 about its periphery 86a. With this construction, distendable membrane is securely clamped in position with cover 44 overlaying ullage substrate 88a and membrane 86 in a manner to sealably enclose the assembly within the hollow housing portion of the device.

After the reservoir has been filled and as membrane 86 moves toward substrate 88a during the fluid dispensing step, fluid within reservoir 82 will be uniformly and controllably forced outwardly through a passageway 84 and then on toward the important flow control means of the invention.

Figure 3:
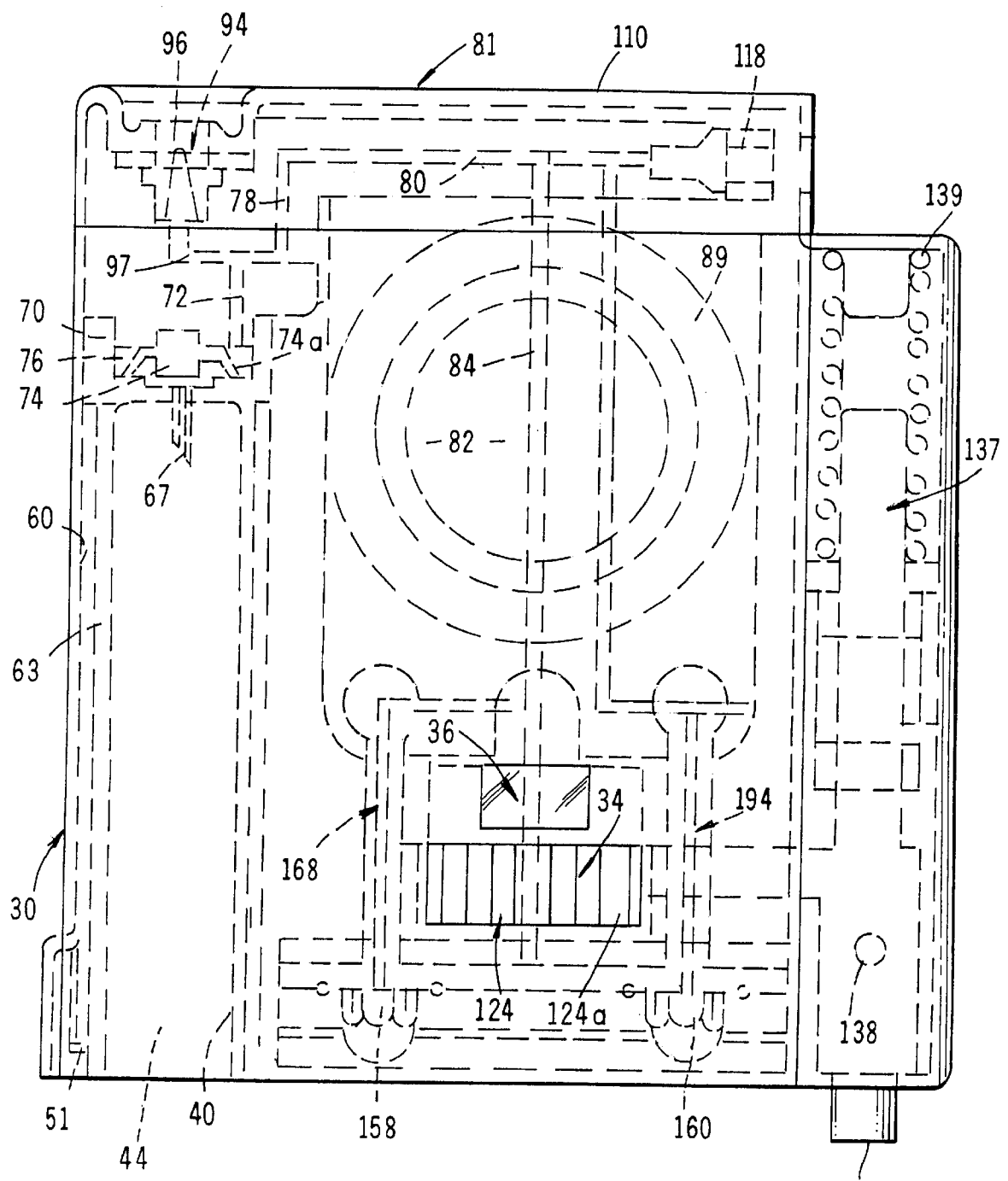
FIG. 3 is a top plan view of the apparatus shown in FIG. 1.
Figure 5:
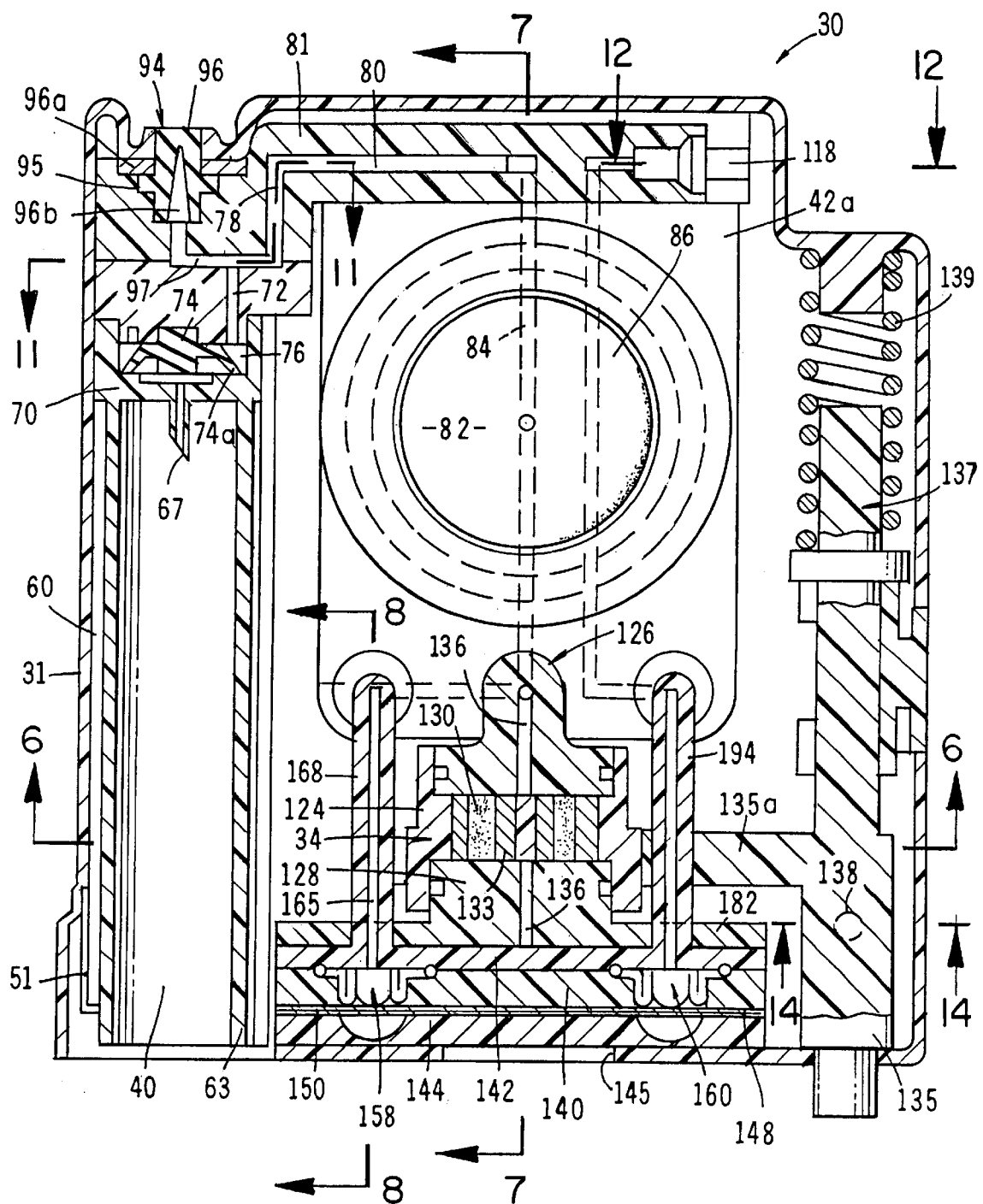
FIG. 5 is a cross-sectional view taken along lines 5—5 of FIG. 4.
Figure 10:
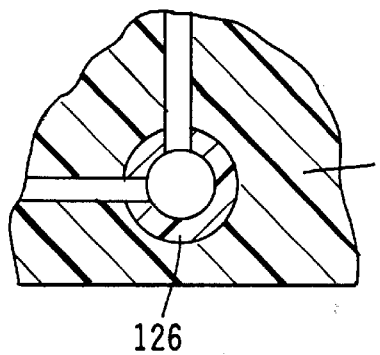
FIG. 10 is an enlarged, cross-sectional view taken along lines 10—10 of FIG. 7.
Figure 11:
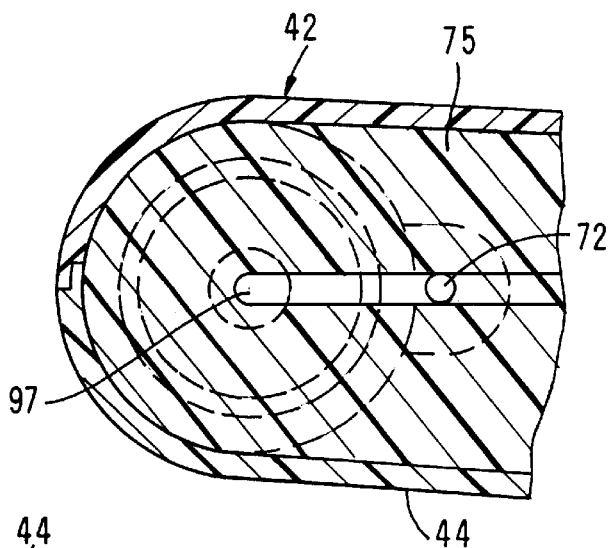
FIG. 11 is an enlarged, cross-sectional view taken along lines 11—11 of FIG. 5.
Figure 12:
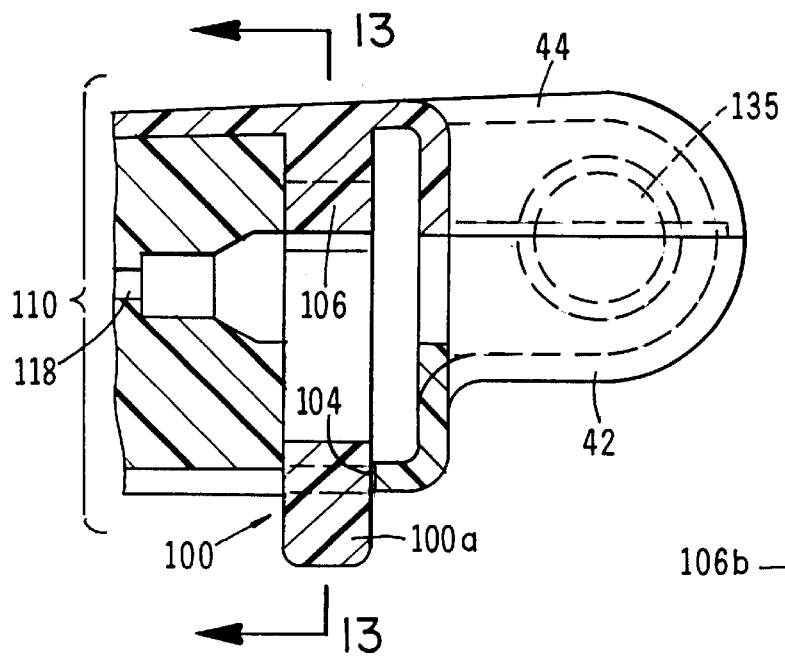
FIG. 12 is an enlarged cross-sectional view taken along lines 12—12 of FIG. 5.

As illustrated in FIGS. 3 and 5, the embodiment of this latest form of the invention also includes a uniquely designed fluid recovery means mounted within manifold 81. As indicated in FIGS. 5 and 17, manifold 81 is connected to ullage substrate 88a and is in communication with reservoir 82 so that fluid can be recovered as may be desired from reservoir 82. This novel recovery means here comprises a recovery septum assembly 94 which is mounted within a cavity 95 formed in manifold 81. Septum assembly 94 includes a septum retainer ring 96a (FIG. 17) and a pierceable elastomeric septum 96 of generally conventional design. Septum 96 includes an internal chamber 96b which is in communication with a fluid passageway 97 which, in turn, communicates with reservoir 82 via passageways 78, 80 and 84. Septum 96 is pierceable by the cannula of a conventional syringe so that, as desired, fluid can be readily recovered from reservoir 82 using a conventional syringe.

Figure 13:
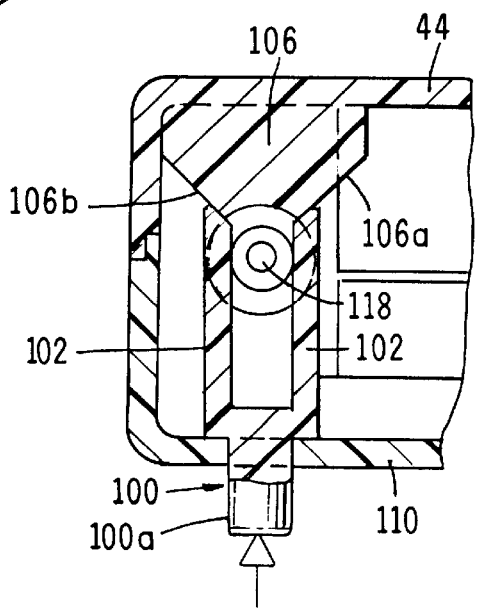
FIG. 13 is a cross-sectional view taken along lines 13—13 of FIG. 12.

Turning particularly to FIGS. 13 and 17, the novel delivery line interconnection and release means of the invention is there illustrated. This means functions to releasably interconnect the delivery assembly, which is of the character shown in FIGS. 1 and 17 to housing 30. This novel interconnection and release means here comprises a push button subassembly 100, which includes a head portion 100a and a pair of yieldably deformable legs 102 (FIG. 13). A part of head portion 100a extends through an aperture 104 formed in closure component 110 in the manner shown in FIG. 13 so that the deformable legs 102 engage the ramp sides 106a and 106b of a ramp unit 106 (FIG. 17). Ramp unit 106 is connected to the base portion of a closure component 110 which closes the back end of housing 30. Each of the legs 102 of the push button subassembly lockably engages a shoulder 112 provided on the delivery fitting 114 (FIG. 17) when the push button subassembly is in an upward, at-rest position. It is apparent that a downward force exerted on head portion 100a will cause legs 102 to move downwardly along rampsides 106a and 106b causing legs 102 to spread apart a sufficient distance to clear shoulder 112 so as to permit withdrawal of delivery fitting 114. When the delivery line is connected to the housing in the manner described, fluid can flow from reservoir 82 outwardly of the device via a novel flow rate control means, the character of which will next be described.

Figure 15:
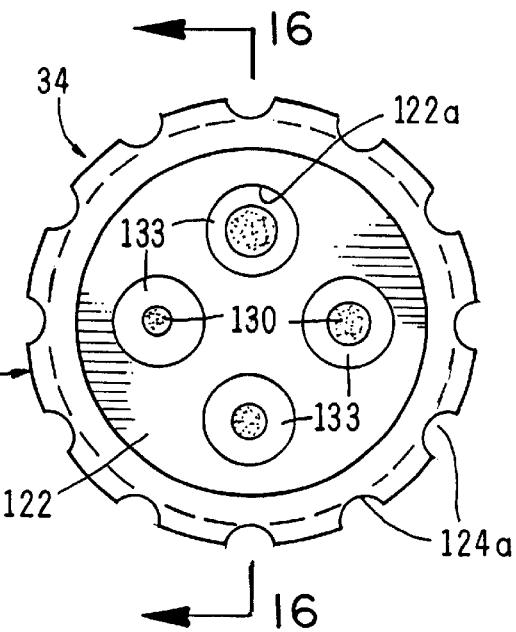
FIG. 15 is a front-elevational view of one form of the control member of the adjustable rate control means of the invention.
Figure 16:
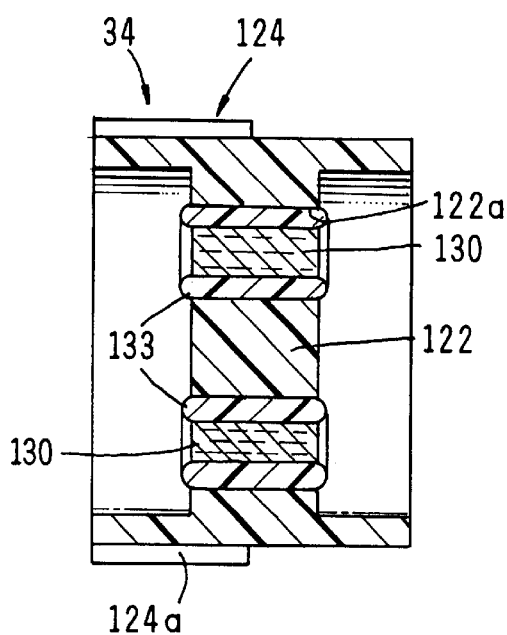
FIG. 16 is a cross-sectional view taken along lines 16—16 of FIG. 15.

The flow rate control means is a very important feature of the apparatus of the invention and functions to adjustably control the rate of fluid flow from the reservoir 82 of the apparatus to the device outlet passageway 118. This novel means here comprises the previously mentioned adjustable rate control mechanism 34 which is carried by housing 30. As best seen in FIGS. 6, 15, and 16, mechanism 34 includes a central body portion 122 which is disposed internally of a knurled control knob 124. Knob 124 is rotatably supported by members 126 and 128 which are mounted internally of housing 30 (FIG. 17). O-rings carried by members 126 and 128 sealably engage control knob 124 and prevent fluid leakage among the various cooperating components.

Figure 18A:
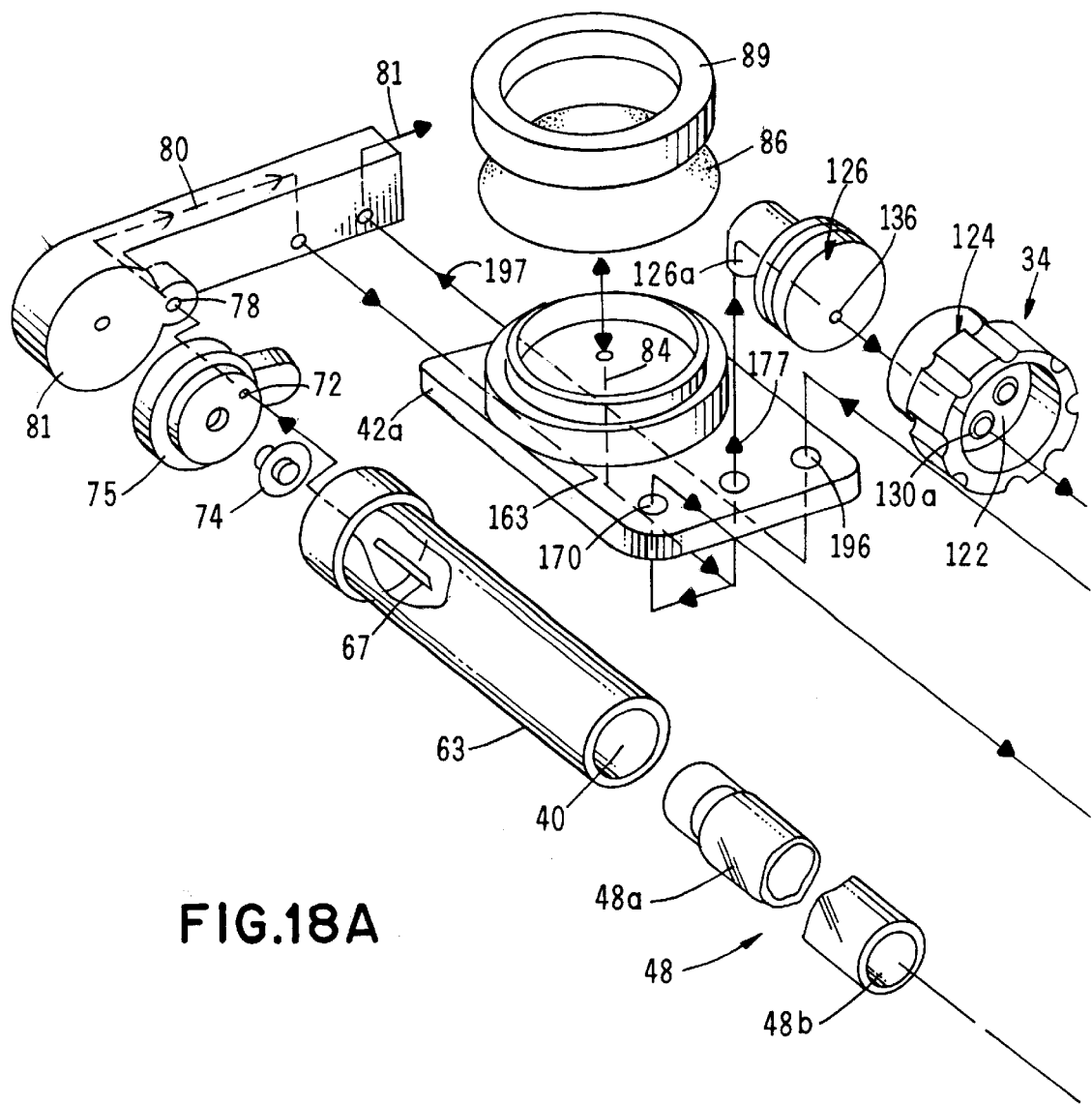
FIGS. 18A and 18B, when considered together, comprise a generally perspective, exploded view similar to FIGS. 17A and 17B and showing the fluid flow paths through the apparatus.
Figure 18B:
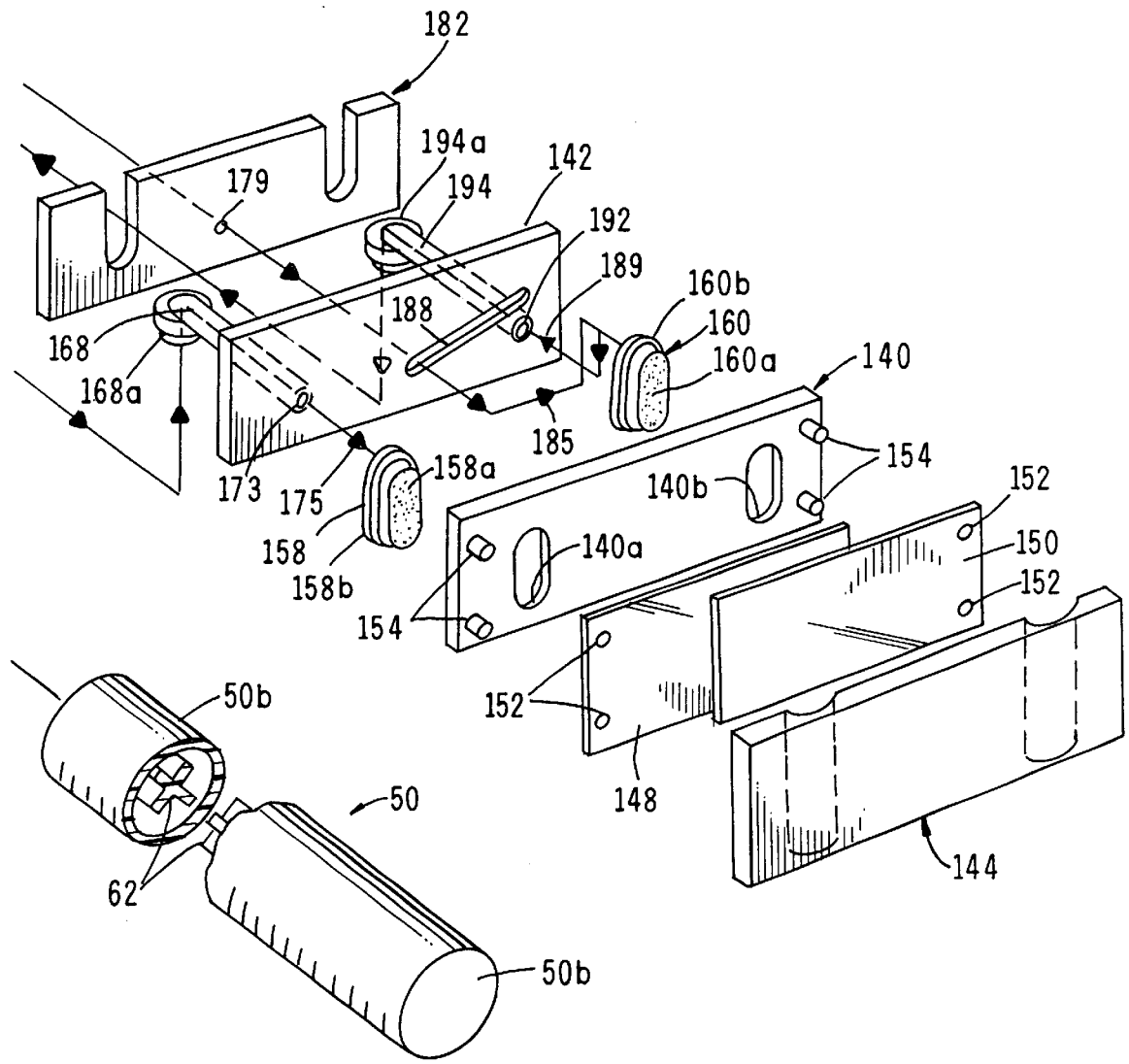

As best seen in FIGS. 15 and 16, central body portion 122 carries a plurality of circumferentially spaced apart flow restrictors. By rotating knob 124, each of the flow restrictors can be selectively moved into index with the flow passageways which carry the fluid from reservoir 82 to the outlet of the device. In the embodiment of the invention shown in the drawings, the flow restrictors are provided in the form of rate control frits 130 (see FIGS. 15 and 16), which are secured in place within apertures 122a formed in body 122 by a moldable elastomer 133 (see FIG. 16). With the construction shown, by rotating knob 124 relative to housing 30, each of the rate control frits 130 can be moved sequentially into alignment with a fluid passageway 136 which extends through members 126 and 128 (FIGS. 17 and 18). Because each of the frits 130 is of a different, preselected porosity, it is apparent that the rate of fluid flowing outwardly of the device through outlet passageway 118 can be precisely controlled by positioning a particular frit in the flow path.

Figure 14:
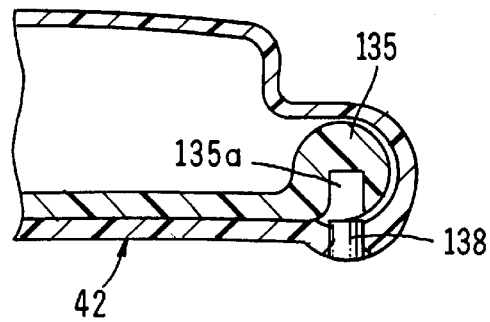
FIG. 14 is a cross-sectional view taken along lines 14—14 of FIG. 5.

An important feature of the invention is the rate control lock-out means which locks knob 124 against rotation. This lock-out means here comprises a locking member 135 which is mounted on an elongated push rod 137 that is carried by base 42 for movement between a first extended locking position and an inward position. Extending from locking member 135 is a locking tab 135a which is movable into and out of locking engagement with channels 124a provided on knob 124 by movement of rod 137 between its first and second positions. A rod biasing means, here provided as a coil spring 139 which is carried within the device housing functions to continuously bias push rod 137 toward its second extended knob engaging locked position. As shown in FIG. 17, rod 137 can be locked in the extended locked position by a lock means here provided as a generally cylindrical shaped rotatable member 141. Member 141 has a stem portion 141a which can be rotated into and out of locking engagement with a notch 137b formed in rod 137. The head portion 141b of member 141 has spaced apart spanner holes which receive spanner pins 141c provided on the physician key 141d which is of the character shown in FIG. 17. Disabling means for disabling the device is here provided in the form of a disabling button 138 (FIGS. 14 and 17) which is carried by base 42. Button 138 can be pushed into a cavity 135a in member 135 so as to prevent its movement and thereby disable the device.

Another unique feature of the apparatus of the invention is a novel flow indicator means which functions to distinguish among three conditions of operation of the device, namely normal fluid flow, blockage or occlusion, and reservoir empty.

Turning particularly to FIG. 17, this novel flow indicator means here comprises an indicator base or platform 140 and a boot clamping plate 142. Additionally, the indicator means comprises a support or lens plate 144. Platform 140, clamping plate 142 and support plate 144 are all enclosed within housing 30 to in the manner indicated in FIG. 17. When the components are positioned within housing 30, plate 144 is viewable through an aperture 145 provided in housing 30 (see also FIGS. 5 and 7).

Disposed between lens plate 144 and platform 140 are first and second indicia-carrying means shown here as a pair of closely adjacent, thin films 148 and 150. Films 148 and 150, are in intimate contact and are preferably constructed from a substantially transparent, flexible polymer material such as Mylar. It is to be understood that the indicia-carrying means need not be thin films, but rather can be any type of surface presenting member upon which indicia can be provided. The downstream surface of the inferior or first film 148 is printed with three integrated symbols (see FIGS. 4, 6, and 8 of incorporated by reference U.S. Pat. No. 5,721,382, which may comprise, by way of example, a blue circle, a green arrow, and a red cross, each consisting of diagonal strips of color printed in an alternating pattern (blue, green, red, blue, green, red, and so on). The second film 150 serves as a "mask" over film 148 and is printed with a pattern of diagonal alternating clear and opaque strips that occur in approximately a 1:2 ratio. The printed ratio of the "mask" allows only one colored symbol to appear at a time when viewed through viewing lens plate 144. The inferior and superior films are provided at their opposite ends with apertures 152 which receive retention pins 154 provided on platform 140 (FIG. 17) which permit attachment of the film to platform 140 in a manner such that the non-patterned portions of each film covers boot openings 140a and 140b provided proximate each end of platform 140 with the patterned portions of both the superior and inferior films being maintained in index. With this construction, each thin film is able to move in response to pressure exerted thereon by the actuating means of the invention, the character of which will presently be described, in opposing directions parallel to the film plane with its range of motion limited to one axis in the film plane. As the films move, the visible symbol pattern will, of course, change due to the transverse displacement of the patterns imprinted thereon.

As will be discussed in greater detail hereinafter and as is apparent from a study of FIGS. 17 and 18, the central portions of both the first and second elastomeric actuator elements or boots 158 and 160, which here comprise the actuator means of the invention, will be deflected outwardly in a direction toward plate 144 when the device is filled and primed, but not in a state of delivery or when there is a build up of fluid pressure during delivery that is caused by blockage of the delivery line downstream from boot 158. While boot 158 can be deflected by normal line pressure, boot 160 is deflected only by pressure buildup resulting from the downstream blockage (see FIG. 18). When both elastomeric boots 158 and 160 are deflected outwardly, both the superior and inferior films are displaced transversely to a second position revealing a second symbol, as for example, an X as viewed through the viewing aperture of the support plate (see also FIGS. 35 and 36 of U.S. Pat. No. 5,721,382 which is incorporated herein by reference).

Figure 32:
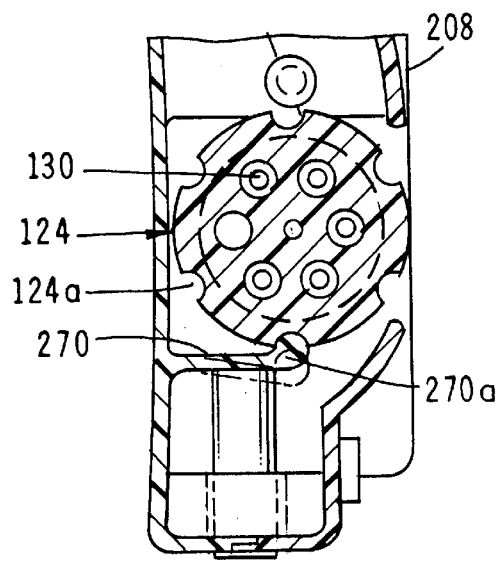
FIG. 32 is a cross-sectional view similar to FIG. 31 but showing the locking pin of the device moved into a locking position.

A third alignment of symbol patterns as shown in FIG. 32 of U.S. Pat. No. 5,721,382 is visible when the device is in an unfilled state or when the delivery line is open, the reservoir is empty and fluid delivery of the patient has been completed. In this case, there is no fluid pressure in the line on either the upstream or the downstream side of the flow control means and thus both the first and second boots are in a non-deflected position. In this condition, the inferior and superior films are not transversely displaced and thus exhibit a third combination of patterns resulting in a third symbol as, for example, a circle being visible through the viewing aperture of the support plate. Boots 158 and 160 can be precisely tailored to deflect under various pressures thereby permitting great apparatus versatility.

During the fluid dispensing step, when fluid is forced through reservoir outlet 163 by the stored energy means, the fluid will flow into a passageway 165 formed in a first base connector element 168 which has a connector head 168a that fits into a first socket 170 formed in base platform 42a. Next, the fluid will flow through an aperture 173 formed in plate 142 and finally into a chamber formed in the distendable, elastomeric first boot 158 of the flow indicator means of the invention. Boot 158 includes a yieldably distendable fluid flow blocking body portion 158a which is circumscribed by a marginal portion 158b. Marginal portion 158b is clamped between plate 142 and platform 140 so that the boot extends through opening 140a formed in platform 140. It is to be understood that, when the fluid flowing from reservoir 82 in the direction of the arrow 175 of FIG. 18 impinges upon boot 158, the central portion of the boot will be deflected outwardly into pressural engagement with indicator film 148.

Fluid flowing from reservoir 82 will also flow in the direction of arrow 177 (FIG. 18) into a stub passageway 126a formed in member 126 and then through aperture 136 formed in member 126. After flowing through aperture 136, the fluid will flow through the flow restrictor that is aligned with aperture 136. (This flow restrictor is identified in FIG. 18 by the numeral 130a. Next, the fluid will flow into through an aperture 136 formed in a knob support platform 182 which is connected to base platform 42a. The fluid will then be diverted in the direction of arrow 185 of FIG. 18 into a passageway 188 formed in plate 142.

Next, the fluid will flow from passageway 188 into a chamber 160a formed in elastomeric, distendable boot 160 which also forms a part of the indicator means of the invention. The periphery 160b of indicator boot 160, which is of identical construction to boot 158, is clamped within opening 140b formed in platform 140. After impinging on boot 160, the fluid will next flow back toward plate 142 in the direction of arrow 189, through an orifice 192 formed therein and into a second base connector element 194 which has a base connector head 194a that fits into a socket 196 formed in base platform 42a. From connector element 194, the fluid will flow in the direction of arrow 197 toward the outlet port 118 of the device (FIG. 18).

It is to be observed that fluid flowing from reservoir 82 into passageway 196, and then on toward boot 160 is under a lower pressure than fluid flowing toward boot 158. This is because the pressure of the fluid flowing toward boot 160 has been reduced as a result of the fluid flowing through the adjustable rate control means of the invention. As is more fully discussed in incorporated by reference U.S. Pat. No. 5,721,382, this result enables a determination of the various fluid flow operating conditions of the device namely normal fluid flow, fluid flow blockage or occlusion, and reservoir empty.

Figure 2:
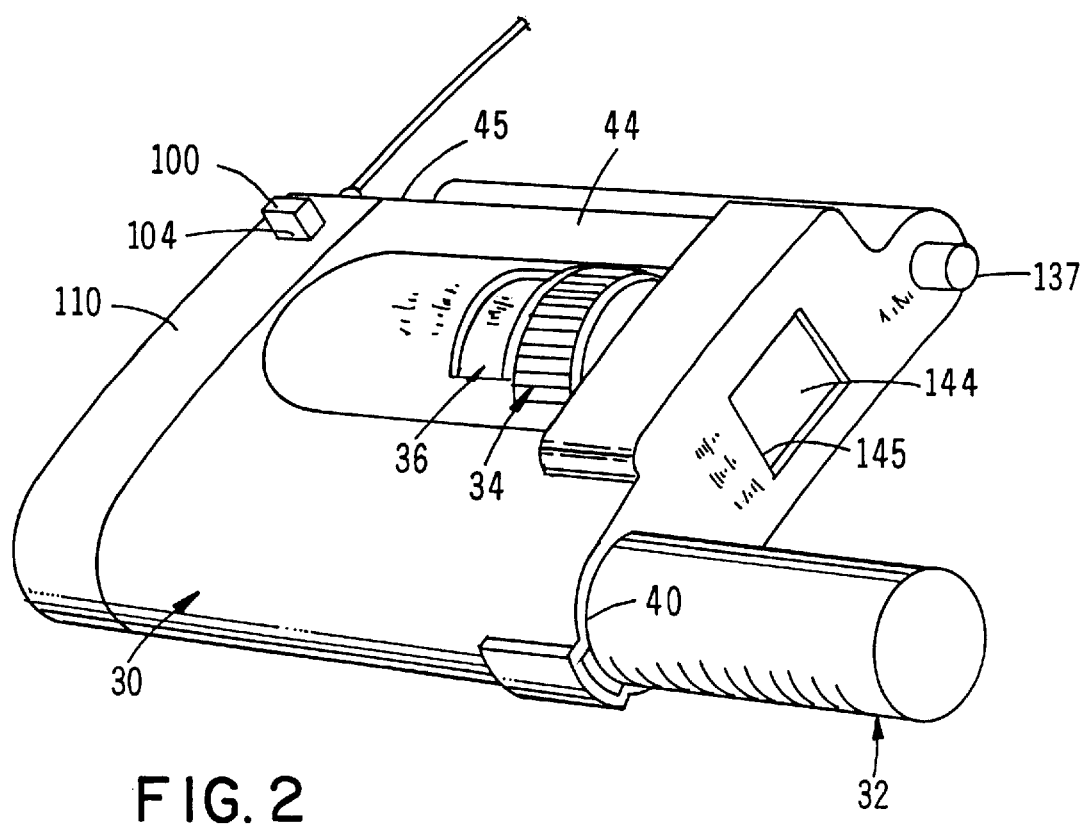
FIG. 2 is a generally perspective top view of the infusion device shown in FIG. 1.

In addition to boots 158 and 160 the flow indicator means also comprises the earlier identified lens 144, which along with platform 140 and support plate 142 are enclosed within housing 30. As best seen in FIG. 2, the viewing lens 144 is viewable through an opening 145 provided in the forward wall.

In using the apparatus of the invention and after the reservoir had been filled using the fill means, the flow rate control means is set to the desired rate of fluid flow. This is done by rotating locking member 141 using a spanner type physician's key. When tab 141a is rotated out of locking engagement with notch 137b, push rod 137 can be pushed forwardly moving the extremity 135b of tab 135a out of engagement with one of the finger engaging channels 124a formed in knob 124 so as to permit rotation of the knob. After the knob has been rotated by the care giver to bring the appropriate rate control frit 130 into index with the fluid flow passageway, the push rod can be released so that spring 139 will urge the locking tab once more into locking engagement with knob 124. By then rotating member 141 to its locked position and removing the spanner type physician's key from head portion 141b, no further adjustment can be made to the rate control means.

Turning now to FIGS. 20 through 34, an alternate form of the apparatus of the invention for controlled delivery of medicinal fluid flow to a patient is there shown and generally designated by the numeral 200. The apparatus is similar in many respects to that shown in FIGS. 1 through 19 and like numerals are used to identify like components. The apparatus here comprises five major components which include a hollow housing, a fill assembly, an adjustable flow rate mechanism and an indicator assembly for indicating fluid flow to the patient. Housing 202 of the apparatus is quite similar to that shown in FIGS. 1 through 19 and includes a base assembly 204, a stored energy means which cooperates with the base assembly to form a fluid reservoir and an indicator assembly which provides a visual indication of fluid flow through the device. The device housing also carries the important dosing means, the character of which will presently be discussed.

Figure 20:
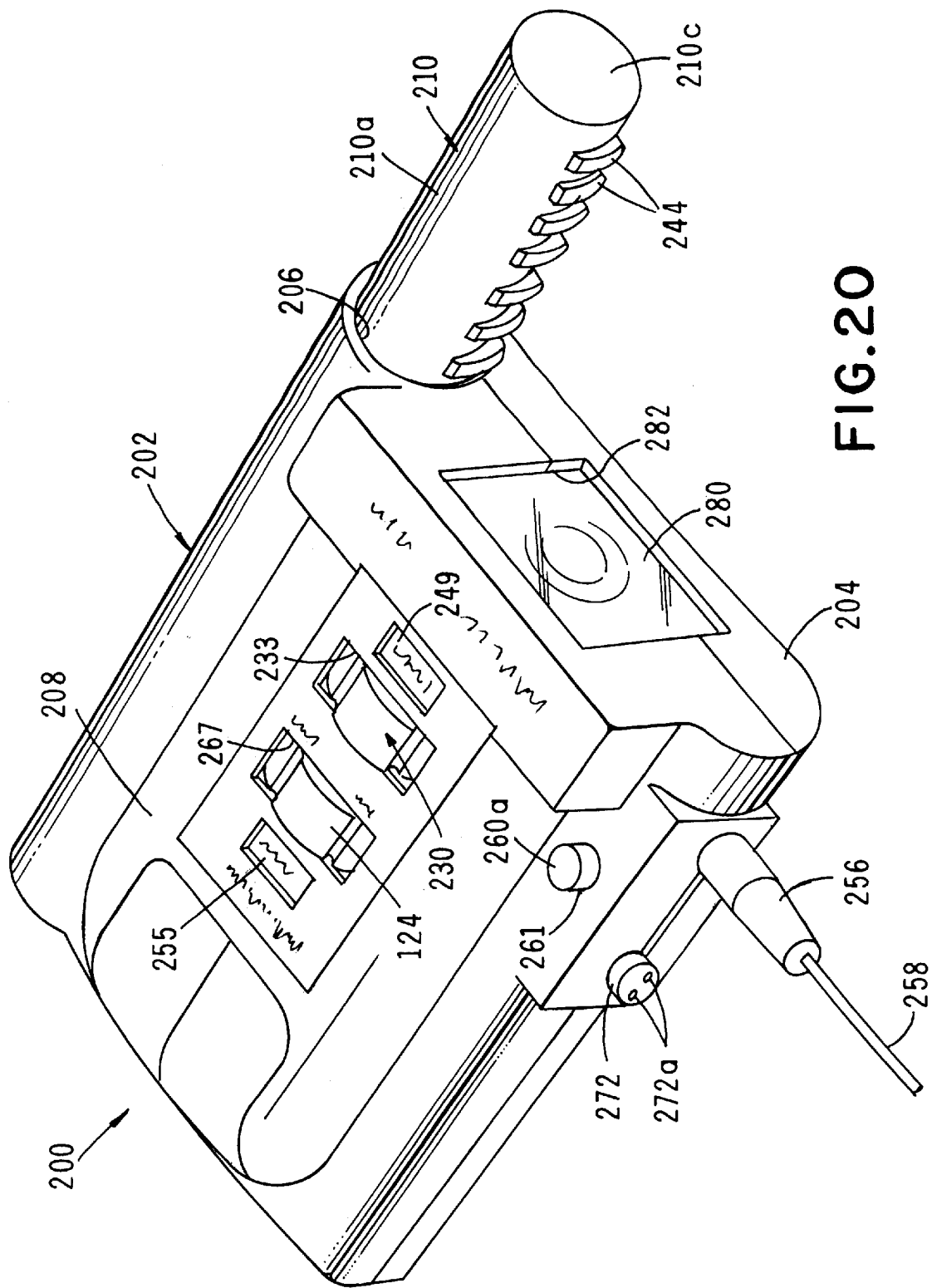
FIG. 20 is a generally perspective view of an alternate form of the infusion device of the present invention.
Figure 21A:
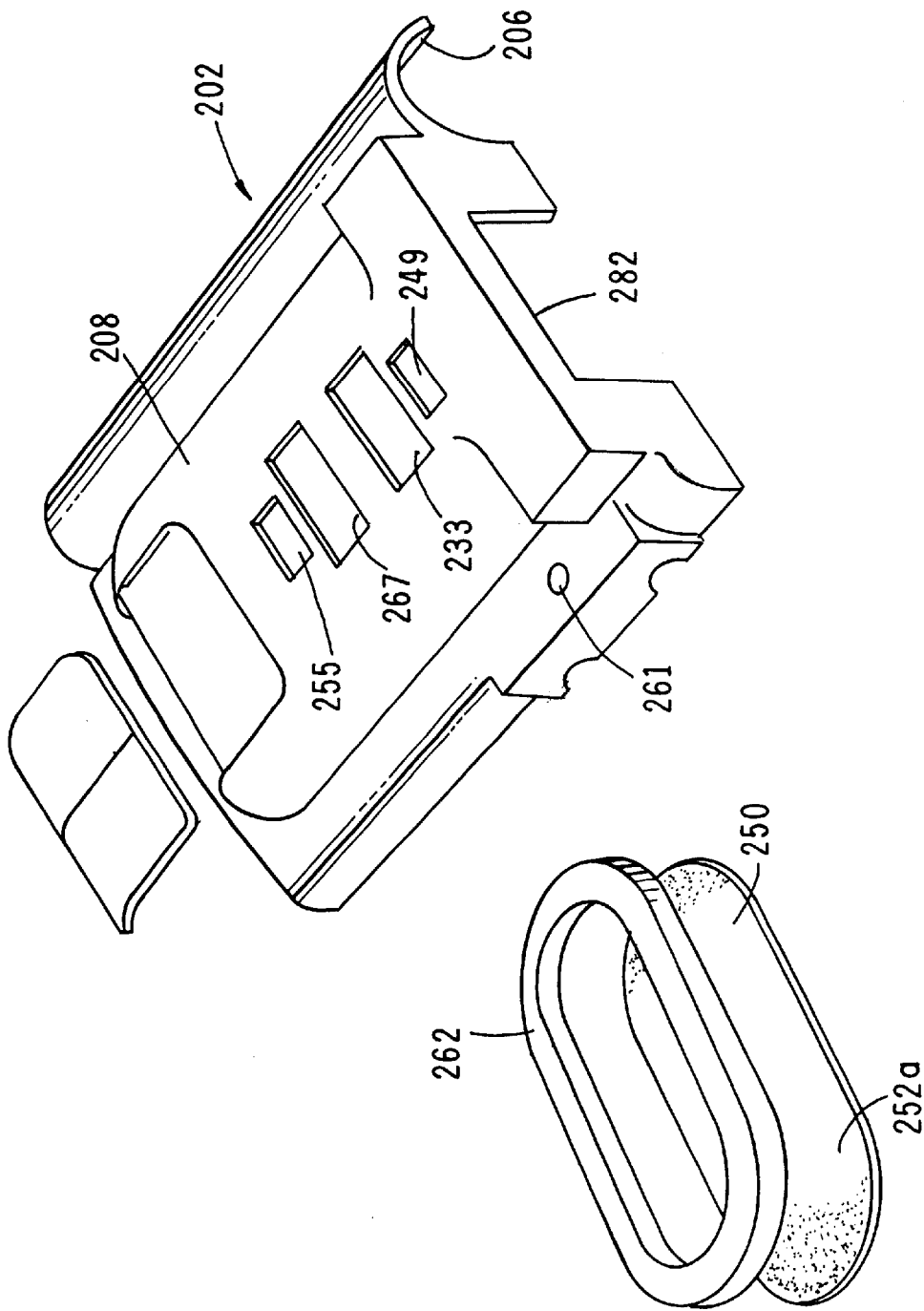

Considering first the hollow housing assembly 202, this assembly is here provided with a uniquely configured receiving chamber 206 which is formed between the base assembly 204 and an interconnected cover component 208 (FIGS. 20 and 21). As before, base assembly 204 and cover component 208 when interconnected, cooperate to define the hollow housing assembly 202. In a manner presently to be described, chamber 206 is adapted to controllably receive the fill assembly of the invention to permit controlled filling of the reservoir of the device and the controlled dispensing of the medicament to the patient.

Figure 22:
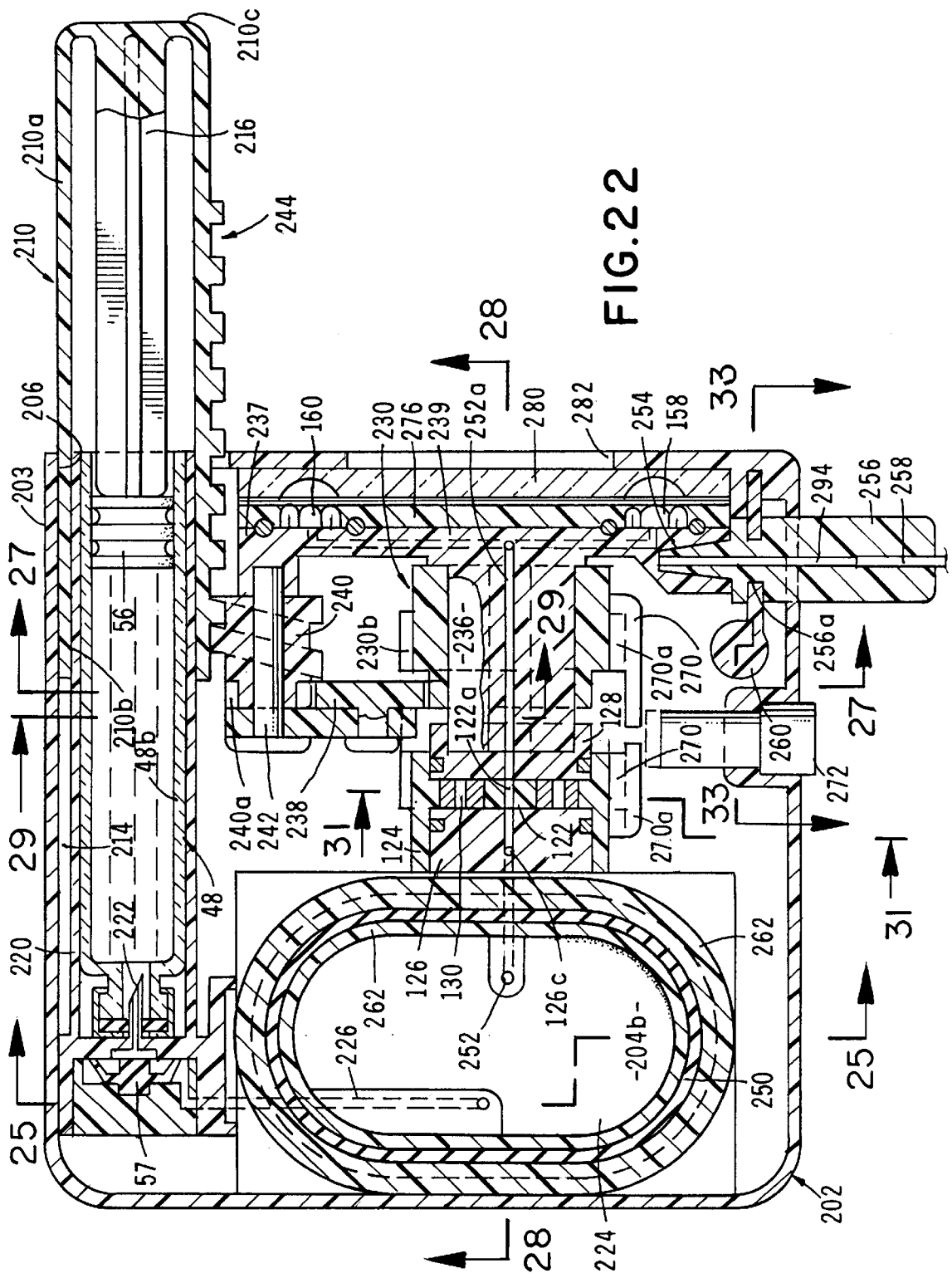
FIG. 22 is a cross-sectional view taken along the horizontal center line of the apparatus shown in FIG. 20 (see lines 22—22 of FIG. 28).
Figure 29:
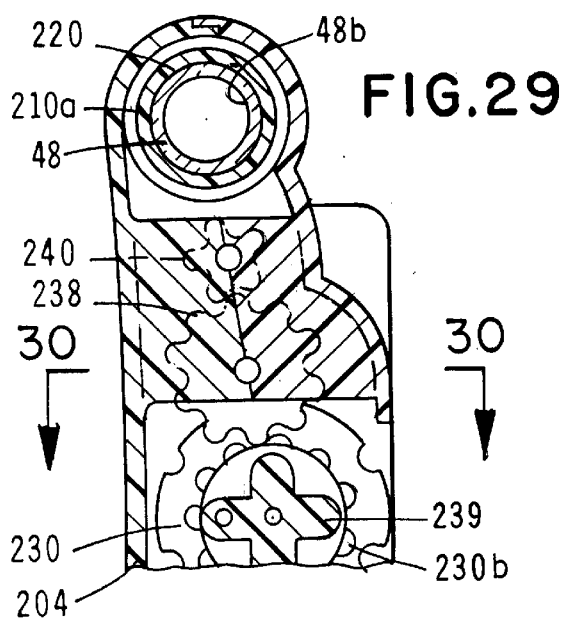
FIG. 29 is a cross-sectional view taken along lines 29—29 of FIG. 22.
Figure 30:
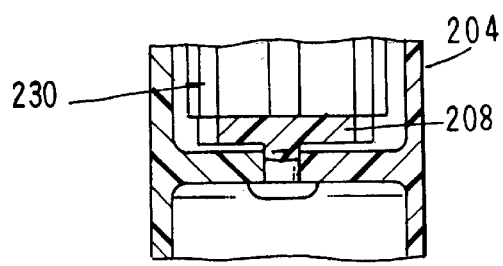
FIG. 30 is a cross-sectional view taken along lines 30—30 of FIG. 29.

Turning particularly to FIGS. 21 and 22 the fill assembly portion of the apparatus can be seen to comprise a container subassembly 48, which is of identical construction to that previously described, and an adapter subassembly 210, which is of a slightly different configuration. As before, a plunger 56 is telescopically movable within chamber 48b of container assembly 48 between first and second locations. As best seen in FIG. 22 adapter assembly 210 comprises a hollow housing 210a having a first open end 210b and a second closed end 210c. The adapter assembly 210 is telescopically receivable within an elongated, generally annular passageway 214 formed in device housing 202 in the manner best seen in FIG. 22 so that the adapter assembly can be moved from a first extended position shown in FIGS. 20 and 22 into a second fluid dispensing position. As was the case with adapter subassembly 50, adapter assembly 210 also includes pusher means shown here as an elongated pusher rod 216 which functions to move plunger 56 within the fluid chamber 48 of the container subassembly upon operation of the dose control means of the invention.

As best seen in FIG. 22, provided within device housing 202 is an elongated, generally cylindrically shaped wall 220 which is concentric with the outer device housing wall which defines receiving chamber 206. Wall 220 is radially spaced from the outer wall 203 of the housing so as to define the previously mentioned longitudinally extending annular space 214 (see also FIG. 25). With this construction, during the mating of the reservoir fill assembly with the base assembly, the outer wall of adapter assembly 210 is closely received within space 214 as the adapter subassembly is urged inwardly or forwardly of the device housing by means of the dose control means. When the adapter assembly is originally mated with the device housing in the manner shown in FIG. 22, the container assembly will be moved telescopically inwardly to move septum 52a of septum assembly 52 into piercing engagement with a hollow cannula 222 which extends inwardly into chamber 48b (see FIG. 21).

Once the fluid flow path between the hollow cannula 222 and the fluid reservoir 224 of the apparatus is thus created via a passageway 226 (FIG. 22), an inward movement of the adapter subassembly can be accomplished using the novel dose control means of the invention. As the operating mechanism of the dose control means controllably moves the adapter subassembly inwardly, pusher rod 216 will move plunger 56 forwardly of chamber 48b. As plunger 56 is moved forwardly, fluid contained within vial chamber 48b, will flow through hollow cannula 222, past check valve 57, into passageway 226 and finally into fluid reservoir 224 (FIG. 25). In certain instances, reservoir 224 may be prefilled with a saline solution or the like with which the fluid contained in vial 48 will be controllably intermixed as the adapter assembly is moved inwardly.

Considering now the previously mentioned dose control means of the invention, this important means here comprises a control knob assembly 230 which includes a collar portion 230a. Assembly 230 is rotatably mounted within device housing 202 so that a portion of the knob extends through an opening 233 formed in cover 208 (FIGS. 20 and 21). More particularly, control knob assembly 230 is rotatably carried by a generally cross-shaped knob support member 236 which is connected to a support platform 239. The details of construction of knob assembly 230 and the drive mechanism associated therewith for advancing adapter assembly 210 into housing 202 are illustrated in FIGS. 21, 22, and 27. As indicated in FIG. 27, control knob 230 is provided with gear teeth 230b which mate with teeth 238a formed on an idler gear 238 which is rotatably carried within device housing 202 in the manner shown in FIG. 30. Idler gear teeth 238a, in turn, mesh with teeth 240a formed on the drive gear 240 which is rotatably supported by a shaft 242 mounted within device housing 202. Drive gear 240 engages longitudinally spaced apart teeth 244 which are formed on adapter housing 210a (FIG. 21). With this construction, as knob 230 is rotated by rotational forces exerted thereon, adapter housing 210a will be caused to controllably move inwardly of annular space 214 causing pusher rod 216 to move plunger 56 inwardly of vial assembly 48. In this way precise incremental doses of the medicament contained within vial 48 can be controllably introduced into reservoir 224. Indicia viewable through a window 249 formed in cover 208 indicate the volume of the dose being dispensed (FIG. 20).

Figure 34B:
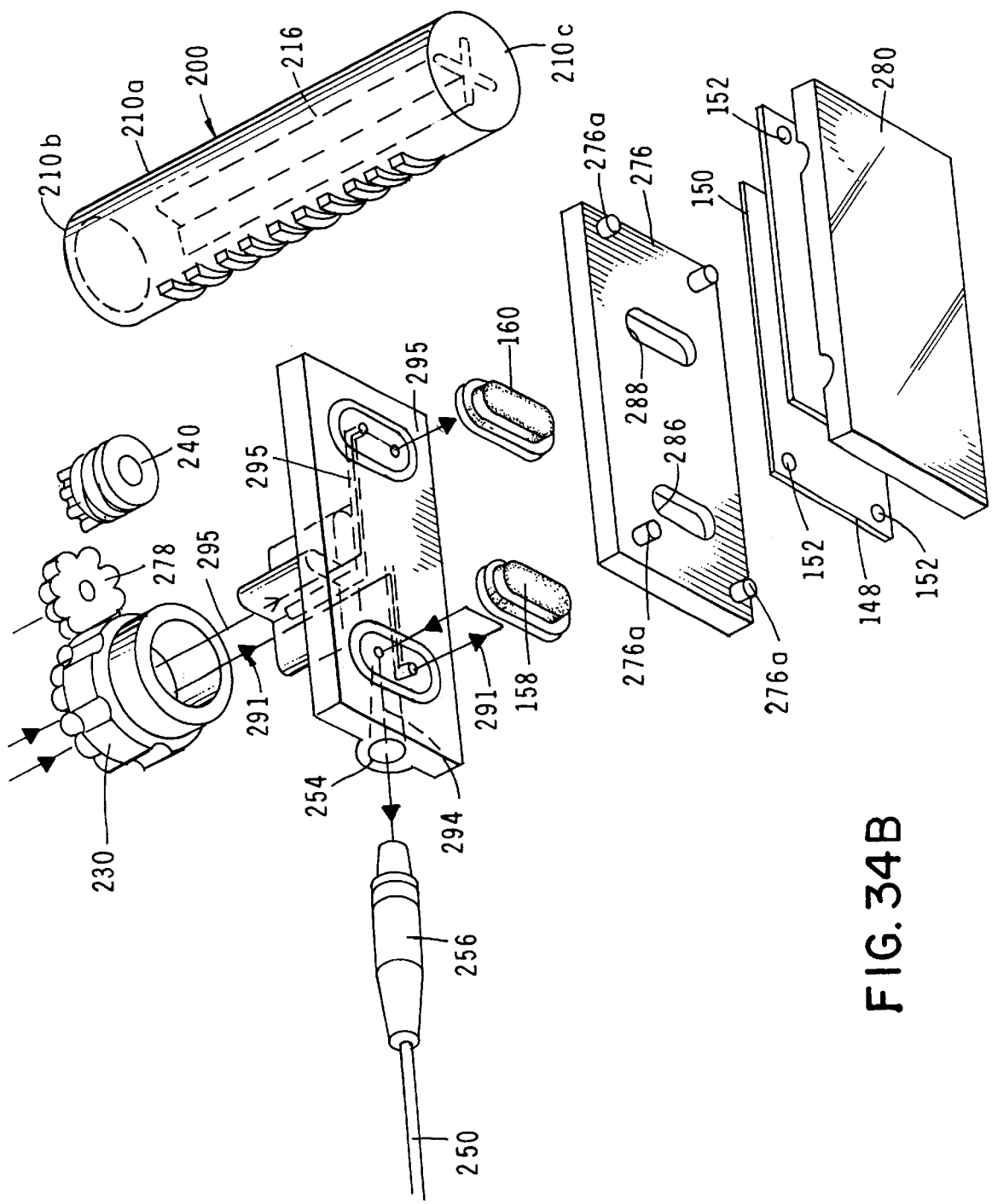

Once the reservoir has been filled and the adapter assembly has been appropriately mated with device housing 202, the apparatus will remain in this readied condition until the outlet passageway of the device is opened. Once the outlet passageway has been opened, the stored energy means or membrane 250 will tend to return to a less distended condition causing fluid to flow outwardly of the apparatus via a passageway 252 formed in base assembly 204, through the novel rate control means of the invention and finally outwardly of the device via an outlet portion 254 (FIG. 34). In a manner presently to be described, a connector 256 and delivery line 258 are connected to the outlet port 254.

As best seen in FIG. 28, base platform 204a, which includes an ullage protuberance 204, is specially configured to receive a membrane clamping ring 262 which functions to securely clamp membrane 250 about its periphery 250a. With this construction, distendable membrane 250 is securely clamped in position with cover 208 overlaying membrane 250 in the manner shown in FIGS. 25 and 28.

Figure 33:
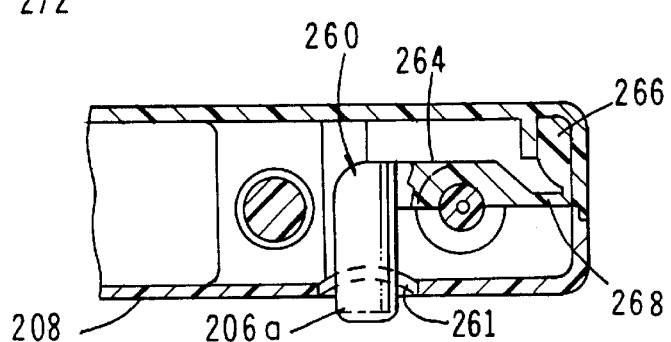
FIG. 33 is a cross-sectional view taken along lines 33—33 of FIG. 22.

Turning next to FIGS. 20, 21, and 33, the novel delivery line interconnection and release means of the invention is there illustrated. This means functions to releasably interconnect the delivery assembly, which here includes connector 256 and delivery line 258. This novel interconnection and release means here comprises a push button subassembly 260, which includes a head portion 260a which extends through an opening 261 formed in cover 208. Connected to head portion 260a is a leg 264 which terminates in a tab 266 which is securely connected to cover 208 (FIG. 33). Disposed between leg 264 and tab 266 is a yieldably deformable segment 268 which functions as a living hinge so that pushing upon head 260a will cause leg 264 to move out of locking engagement with a shoulder 256a formed on connector 256. When the push button subassembly is in an upward, at-rest position, leg 264 locks against shoulder 256a preventing removal of connector 256 from the device housing. However, it is apparent that a downward force exerted on head portion 260a will cause legs 264 to move away from the connector so as to permit it to be disconnected from housing 202. When the delivery line is connected to the housing in the manner described, fluid can flow from reservoir 224 outwardly of the device via the indicator means and via the novel flow rate control means, the character of which will next be described.

The flow rate control means is also a very important feature of this latest form of the invention and functions to adjustably control the rate of fluid flow from the reservoir 224 of the apparatus to the device outlet passageway 254. This novel rate control means is virtually identical in construction and operation to that described in connection with the first embodiment of the invention shown in FIGS. 1 through 19. As before, the rate control means comprises a mechanism 124 which includes a central body portion 122 which is disposed internally of a knurled control knob 124. Knob 124 is rotatably supported by members 126 and 128 which are quite similar to the previously described members 126 and 128 and are mounted internally of housing 202 (FIGS. 17 and 34). A portion of knob 124 extends through an opening 267 formed in cover 208 (FIG. 20).

Figure 31:
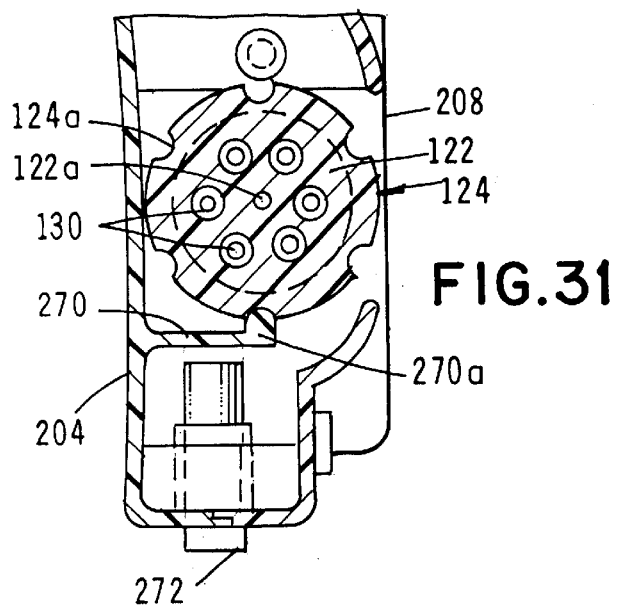
FIG. 31 is a cross-sectional view taken along lines 31—31 of FIG. 22.

As best seen in FIGS. 31 and 32, central body portion 122 carries a plurality of circumferentially spaced apart flow restrictors. By rotating knob 124, each of the flow restrictors can be selectively moved into index with the flow passageway 252 (FIG. 28) which carries the fluid from reservoir 224 to support member 126 of the device. In the manner previously described, by rotating knob 124 relative to housing 202, each of the rate control frits 130 can be moved sequentially into alignment with fluid passageway 252 and with a passageway 126a (FIGS. 28 and 34) which extends through member 126. Because each of the frits 130 is of a different, preselected porosity as indicated by indicia viewable through a window 255 formed in cover 208, it is apparent that the rate of fluid flowing outwardly of the device through outlet passageway 254 can be precisely controlled by positioning a particular frit in the flow path.

Another unique feature of the apparatus of this latest form of the invention which is shown in FIGS. 21, 31, and 32 is a novel control knob locking means which locks knobs 124 and 230 against rotation. This locking means here comprises yieldable knob engagement arms 270 which engage knobs 124 and 230 and prevent their rotation when a locking button 272 is pushed inwardly of housing 202 in the manner shown in FIG. 32. Arms 270 terminate in an end portion 270a which ratchet out of engagement with the grooves 124a formed in knob when the push button is in the retracted position shown in FIG. 31. However, when the push button is pushed in, it will engage arm 270 to prevent its separation from knob 124. Push button 272 is provided with spanner holes 272a (FIG. 26) which accept spaced apart pins provided on a physician's locking key 141d (FIG. 17) which can be used to lock the push button in the locked configuration shown in FIG. 32. With this arrangement once the flow rate is set it cannot be changed by anyone other than an authorized care giver having access to the locking key.

As in the earlier described embodiment, this latest embodiment also includes novel indicator means which functions to distinguish among three conditions of operation of the device, namely normal fluid flow, blockage or occlusion, and reservoir empty. Turning particularly to FIGS. 21 and 34, this novel flow indicator means is quite similar in construction and operation to the previously described flow indicator means and includes an indicator base or platform 276 and a boot clamping plate 278. Additionally, the indicator means here comprises a support or lens plate 280. Platform 276, clamping plate 278 and support plate 280 are all enclosed within housing 202 in the manner indicated in FIG. 21. When the components are positioned within housing 202, plate 280 is viewable through an aperture 282 provided in housing 202 (FIG. 20).

Disposed between lens plate 280 and platform 276 are first and second indicia-carrying means shown here as a pair of closely adjacent, thin films 148 and 150 which are of identical construction and operation to those embodied in the first form of the invention (see also FIGS. 4, 6, and 8 of incorporated by reference U.S. Pat. No. 5,721,382. The inferior and superior films are provided at their opposite ends with apertures 152 which receive retention pins 276a provided on platform 276 (FIG. 34) which permit attachment of the film to platform 276 in a manner such that the non-patterned portions of each film covers boot openings 286 and 288 provided proximate each end of platform 276 with the patterned portions of both the superior and inferior films being maintained in index. With this construction, each thin film is able to move in response to pressure exerted thereon by the actuating means of the invention which is of the character previously. As the films move, the visible symbol pattern will, of course, change due to the transverse displacement of the patterns imprinted thereon.

As before, boots 158 and 160, which here comprise the actuator means of this latest form of the invention, will be deflected outwardly in a direction toward plate 280 when the device is filled and primed, but not in a state of delivery or when there is a build up of fluid pressure during delivery that is caused by blockage of the delivery line downstream from boot 158. While boot 160 can be deflected by normal line pressure, boot 158 is deflected only by pressure buildup resulting from the downstream blockage. When both elastomeric boots 158 and 160 are deflected outwardly, both the superior and inferior films are displaced transversely to a second position revealing a second symbol, as for example, an X as viewed through the viewing aperture of the support plate (see also FIGS. 35 and 36 of U.S. Pat. No. 5,721,382 which is incorporated herein by reference).

A third alignment of symbol patterns as shown in FIG. 32 of U.S. Pat. No. 5,721,382 is visible when the device is in an unfilled state or when the delivery line is open, the reservoir is empty and fluid delivery of the patient has been completed. In this case, there is no fluid pressure in the line on either the upstream or the downstream side of the flow control means and thus both the first and second boots are in a non-deflected position. In this condition, the interior and superior films are not transversely displaced and thus exhibit a third combination of patterns resulting in a third symbol as, for example, a circle being visible through the viewing aperture of the support plate. As before, boots 158 and 160 can be precisely tailored to deflect under various pressures thereby permitting great apparatus versatility.

During the fluid dispensing step, when fluid is forced through the reservoir outlet by the stored energy means, the fluid will flow into passageway 252, and then will be split into two flow paths 252a and 252b. Flow path 252a extends through a first orifice 126c formed in member 126 and then through a central orifice 122a formed in control member 122. Flow path 252b extends through a second orifice 126a formed in member 126 and then through a selected frit 130 of the rate control means. From the selected frit 130, the fluid will flow at a reduced pressure into a chamber formed in the distendable elastomeric first boot 158 in the direction of the arrows 291. When the fluid flowing from reservoir 224 in the direction of the arrow 291 of FIG. 34 impinges upon boot 158, the central portion of the boot will be deflected outwardly into pressural engagement with indicator film 148. After impacting boot 158, the low pressure fluid will then flow back into outlet passageway 294 (FIG. 22) and outwardly of outlet 254 at the predetermined rate of flow.

Fluid flowing from reservoir 224 along path 252a will flow through orifice 126c formed in member 126 and then through a passageway formed in hub-like member 236. Next, fluid will flow in the direction of arrows 295 into elastomeric, distendable boot 160 which also forms a part of the indicator means of this latest form of the invention.

It is to be observed that fluid flowing from reservoir 224 along path 252a and through central orifice 122a of member 122 will flow toward boot 160 under a higher pressure than fluid flowing toward boot 158. This is because the pressure of the fluid flowing toward boot 158 has been reduced as a result of the fluid flowing through the adjustable rate control means of the invention. As is more fully discussed in incorporated by reference U.S. Pat. No. 5,721,382, this result enables a determination of the various fluid flow operating conditions of the device namely normal fluid flow, fluid flow blockage or occlusion, and reservoir empty.

Figure 36:
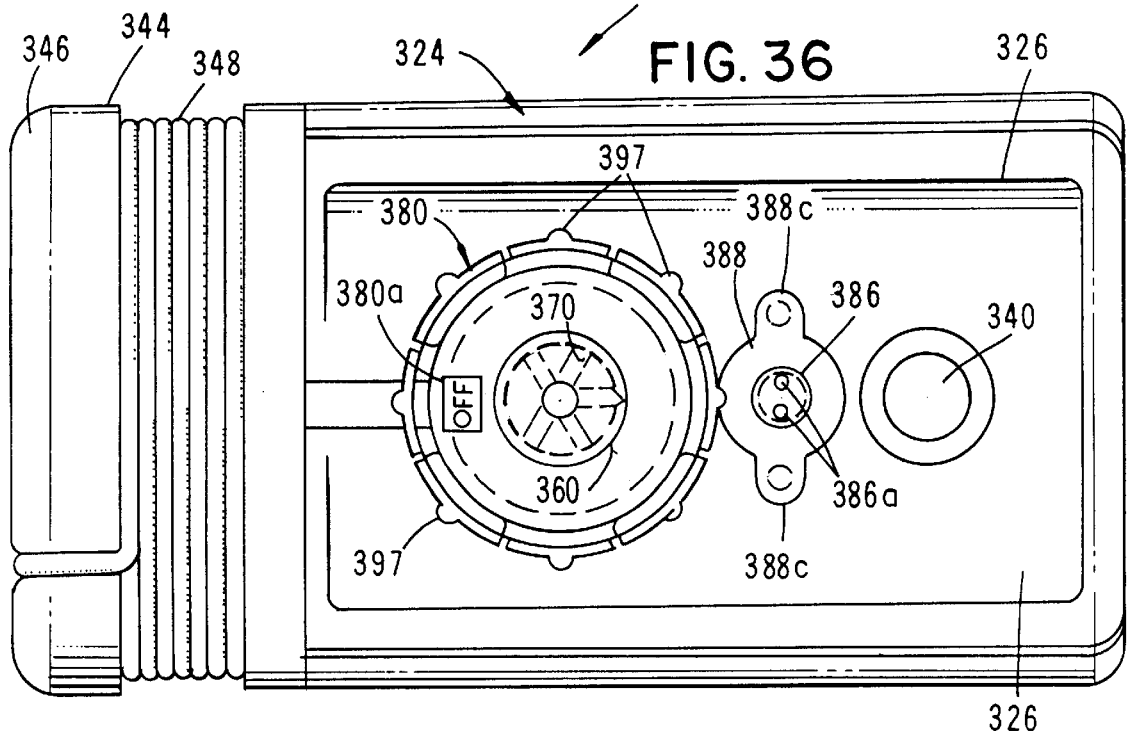
FIG. 36 is an enlarged bottom view of the device shown in FIG. 35.
Figure 37A:
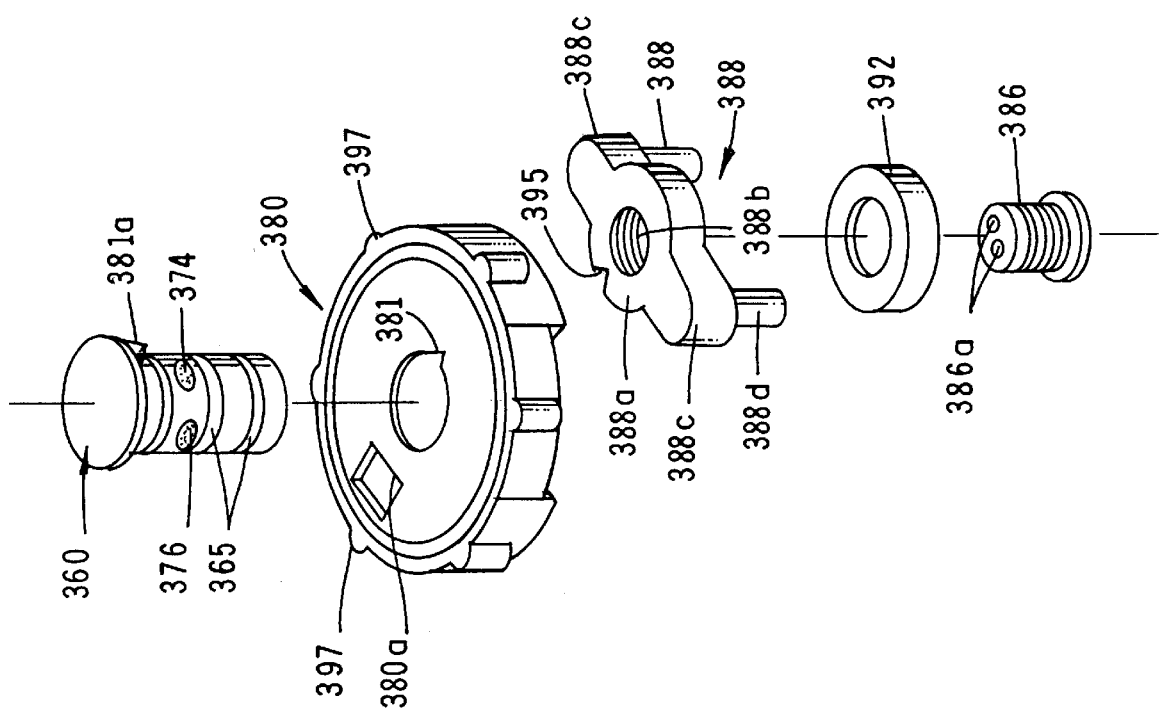
Figure 38:
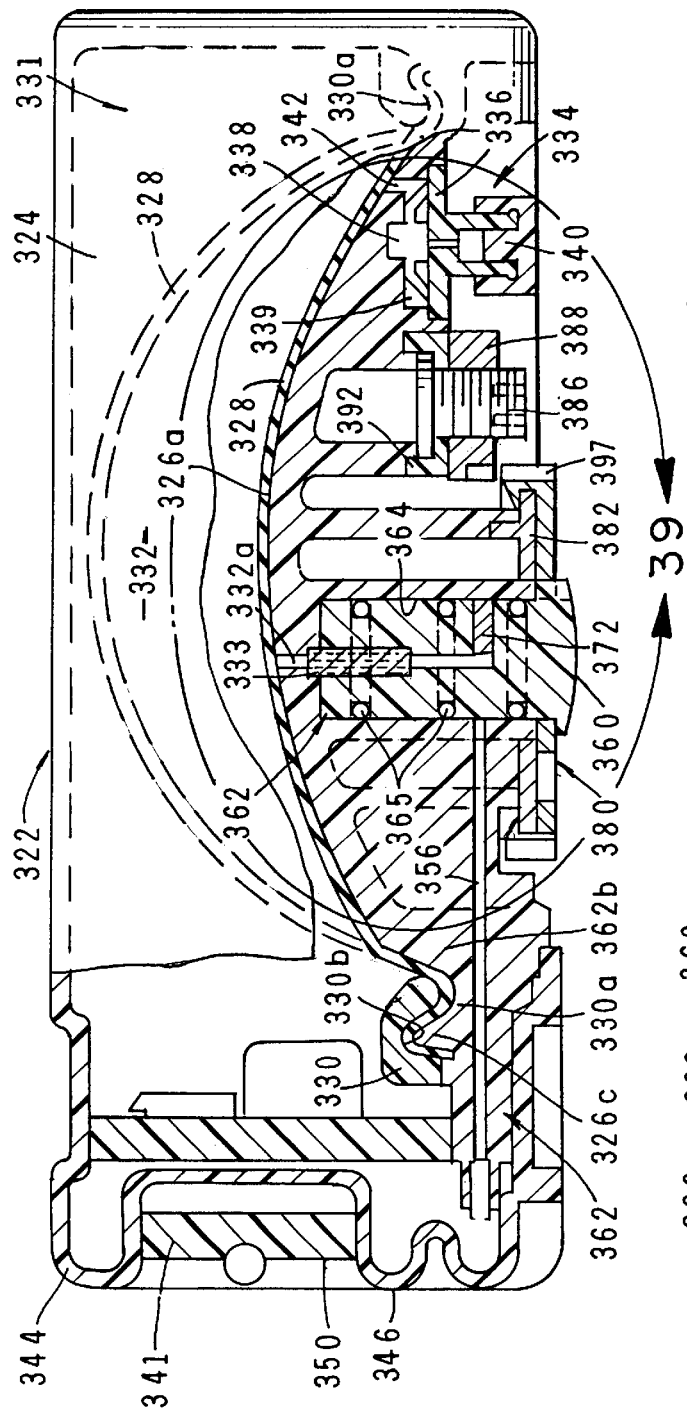
FIG. 38 is a side-elevational, cross-sectional view of the apparatus.
Figure 39:
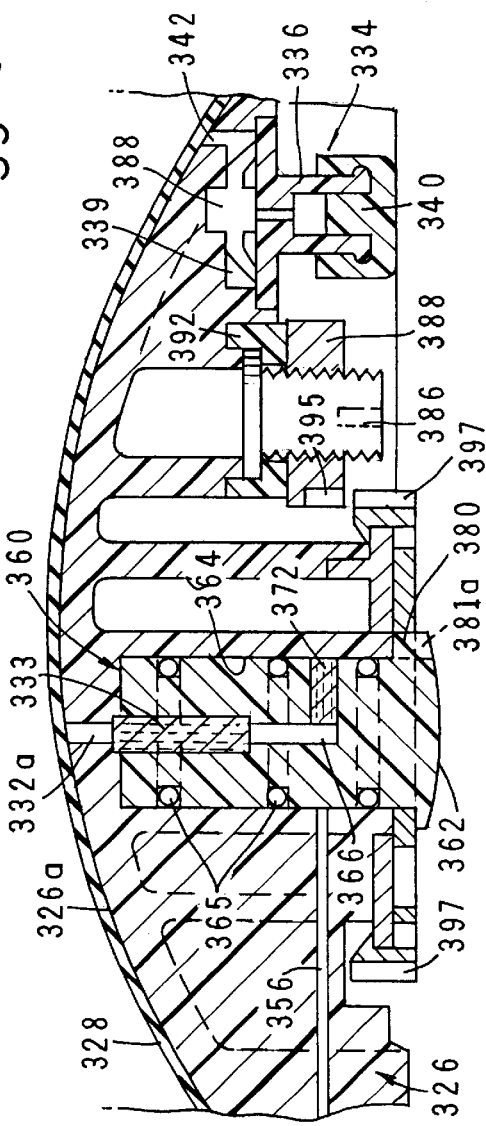
FIG. 39 is an enlarged, cross-sectional view of the area designated in FIG. 38 by the numeral 39.

Turning next to FIGS. 35 through 45, one form of the fluid dispenser assembly of the apparatus of the invention is there shown and generally designated by the numeral 322. The fluid dispenser component of the apparatus is somewhat similar in operation to that previously described herein, but is of a somewhat different configuration. As best seen in FIGS. 35 through 38, this latest embodiment includes a housing assembly 324 having a base 326 and a stored energy source, or distendable membrane 328 (FIG. 38) which is superimposed over base 326 and is clamped thereto by a clamping ring 330. A cover 331 is provided for enclosing the stored energy source and the capture ring. As indicated in FIGS. 38 and 39, the base 326 includes an ullage defining protuberance 326a and a membrane capture portion 326b. Membrane capture or clamping ring 330 has a bottom opening 330a which receives protuberance 326a of base 326 in the manner best seen in FIG. 38.

Referring particularly to FIGS. 37, 38, and 39, base 326 comprises, in addition to the distendable member, engaging protuberance, or ullage 326a, connector means, the character of which will presently be described, for connecting to the base one form of the novel fluid flow control means of the invention. Base 326 also includes an upstanding tongue 326c which extends about the perimeter of the base and is closely receivable within a groove 330b formed in the capture ring 330 (FIG. 38). When the base and the membrane capture ring are assembled in the manner shown in FIG. 38, the periphery of distendable membrane 328 will be securely clamped within groove 330b by tongue 326c. After the parts are thus assembled, base 326 is bonded to capture ring 330 by any suitable means such as sonic bonding which also functions to simultaneously trim membrane 328.

Also comprising a part of housing assembly 324 is filling means for filling the fluid reservoir 332 of the fluid dispenser assembly, which reservoir is defined by the upper surface of base 326 and the lower surface of distendable membrane 328. This filling means here comprises a fill assembly 334 which includes a fill port 336 that is connected to base 326 and valve means for controlling fluid flow toward reservoir 332. This valve means here comprises a conventional umbrella valve 338 that is disposed within a chamber 339 formed in base 326 (FIG. 39).

During the reservoir filling step, a closure cap 340 is first removed and a fill line having an appropriate luer connector is connected to fill port 336. This done, fluid under pressure will flow into inlet passageway 342 of the fluid dispenser via an umbrella valve 338 and thence into a reservoir 332. As the fluid under pressure flows into the reservoir, it will cause membrane 328 to distend outwardly from protuberance 326a in the manner shown by the phantom lines in FIG. 38. Check valve 338 will, of course, prevent fluid flow in a direction from reservoir 332 toward fill port 336.

Figure 35:
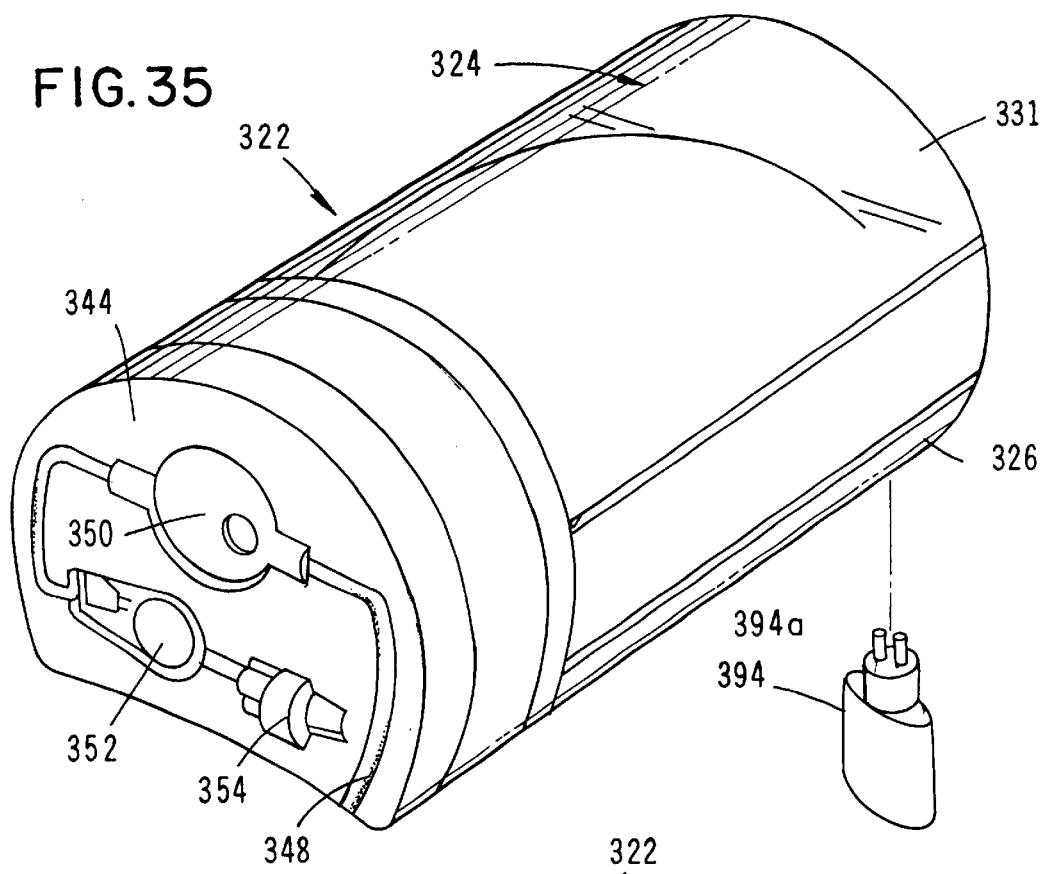
FIG. 35 is a generally perspective bottom view of still another form of the apparatus of the present invention which is of a somewhat different configuration.

As indicated in FIG. 35, infusion set storage means for storing the infusion set or infusion means of the apparatus is provided proximate the forward end of the housing of the dispenser. This storage means here comprises a part of the cover means of the invention which includes the previously identified cover 331. The cover means also includes a forward housing portion 344 (FIG. 35) which is interconnected with cover 331 and base 326. Housing portion 344 functions to close the forward or delivery end of the dispenser component. As best seen in FIG. 38, housing portion 344 includes a front face 346 that is provided with a plurality of socket-like cavities that house the component parts of the infusion set of the invention, namely an infusion line 348, a gas vent assembly 350, a line clamp 352 and an outlet luer connector 354. When forward housing portion 344 is mated with base assembly 326, infusion line 348 will communicate with outlet passageway 332a of reservoir 332 via an outlet passageway 356 formed in base 326 (FIG. 38). In a manner presently to be described, passageway 356, in turn, communicates with reservoir 332 via the novel fluid flow control means of the invention.

Figure 40:
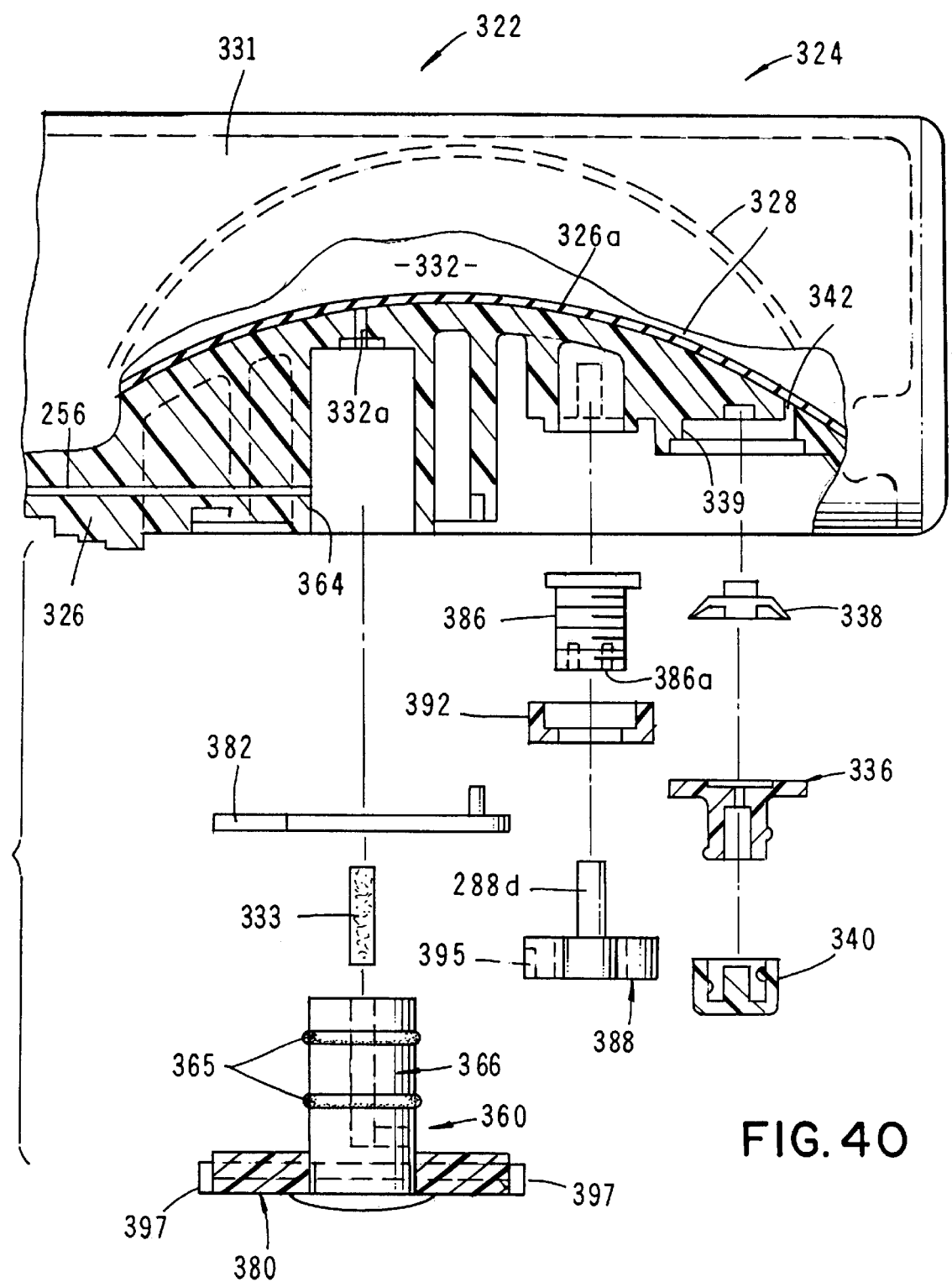
FIG. 40 is a cross-sectional exploded view of the portion of the device shown in FIG. 39.

The novel fluid flow control means of the form of the invention shown in FIGS. 35 through 45 comprises a novel flow control assembly 360 which includes a rate control shaft 362 that is rotatably mounted within a cylindrical bore 364 formed in base 326 (FIG. 40). As best seen in FIGS. 39 and 42, shaft 362 is provided with a plurality of circumferentially spaced, radial bores 366 within which are mounted first, second, third, fourth and fifth flow restrictors or porous frits 368, 370, 372, 374 and 376 respectively. Connected to shaft 362 proximate its outboard end is a rate control wheel 380. Wheel 380 includes an indexing notch 381 for appropriately indexing wheel 380 to shaft 362. Shaft 362 has a boss 381a which fits into indexing notch 381 on wheel 380. With the construction shown, by rotating control wheel 380 relative to base 326, each of the porous control frits can be moved sequentially into alignment with outlet passageway 356. Because each of the rate control frits is of a different, preselected porosity, it is apparent that the rate of fluid flowing outwardly of the device throughout passageway 356 can be precisely controlled by positioning a particular frit in the flow path between reservoir 332 and outlet passageway 356. In certain instances, it may be beneficial to prefilter the fluid flowing toward the rate control frits by means of a filter 333 (FIG. 38). O-rings 365 are provided in the manner shown in FIGS. 38 and 39 to prevent leakage past the cooperating components.

Located proximate rate control selector wheel 380 is a flow rate indicator disk 382. Disk 382 is provided with indicia 384 viewable through a viewing window 380a formed in wheel 380 which indicia indicate flow rate through the various porous rate control frits mounted within shaft 362.

With the construction described in the preceding paragraphs, once the fluid reservoir is appropriately filled, the desired rate of infusion to the patient can be set by the physician or other caretaker by rotating the control member 380 until the desired flow rate appears through window 380a. Once the flow rate is set, a threaded locking member or screw 386, which is rotatable relative to base 326 in the manner shown in FIGS. 38 and 39, is rotated to secure control member 380 against further rotation. Locking member 386, which comprises a part of the locking means of the invention is threadably connected to a control member engaging component 388. Component 388 includes a central body portion 388a having a threaded aperture 388b and a pair of outwardly extending, arm-like protuberances 388c. Connected to each protuberance 388c is a downwardly extending stub shaft 388d. Each stub shaft is slidably receivable within a bore 390a formed in a screw housing 390 provided on base 326 (FIG. 37). A screw retainer ring 392 secures screw 386 in position within screw housing 390. Screw 386 can be rotated using a physician's key 394 of the character shown in FIG. 35 having spaced apart spanner elements 394a that are receivable within spaced apart apertures 386a formed in the head of screw 386. Upon rotation of screw 386, component 388 will be moved downwardly relative to the lower surface of ring 392 so that a notch 395 formed thereon (FIG. 36) will engage one of the circumferentially spaced protuberances 397 formed about the periphery of control component 380. With the control component thus locked against rotation, the rate of infusion to the patient of the medicinal fluids contained within reservoir 332 cannot be changed unless and until the physician or caregiver rotates screw 386 in an opposite direction using the physician's key 394.

Referring next to FIGS. 46 through 53, an alternate form of the fluid dispenser assembly of the apparatus of the invention is there shown and generally designated by the numeral 402. The fluid dispenser component of the apparatus is somewhat similar to the fluid dispenser illustrated in FIGS. 35 through 45 and like numerals are used to identify like components. As before, the fluid dispenser comprises a housing assembly 404 having a base 406. A stored energy source, or distendable membrane 328 (FIG. 49) is superimposed over base 406 and, in the manner previously described, is clamped thereto by a clamping ring 330. A cover 408 of a slightly different design is provided for enclosing the stored energy source and the capture ring. Base 406 includes an ullage defining protuberance 406a and a membrane capture portion 406b. Base 406 also includes an upstanding tongue 406c which extends about the perimeter of the base and is closely receivable within a groove 330b formed in the capture ring 330. When the base and the membrane capture ring are assembled in the manner shown in FIG. 49, the periphery of distendable membrane 328 will be securely clamped within groove 330b by tongue 406c.

Also forming a part of housing assembly 404 is filling means for filling the fluid reservoir 332 of the fluid dispenser assembly, which reservoir is defined by the upper surface of base 406 and the lower surface of distendable membrane 328. This filling means is identical in construction and operation to the previously described fill assembly 334 which includes a fill port 336 which is connected to base 406 and valve means for controlling fluid flow toward reservoir 332.

During the reservoir filling step, closure cap 340 is first removed and a fill line having an appropriate luer connector is connected to fill port 336. This done, fluid under pressure can be urged to flow into inlet passageway 342 of the fluid dispenser via umbrella valve 338 and thence into a reservoir 332. As the fluid under pressure flows into the reservoir, it will cause membrane 328 to distend outwardly from protuberance 406a in the manner shown by the phantom lines in FIG. 49.

Figure 46:
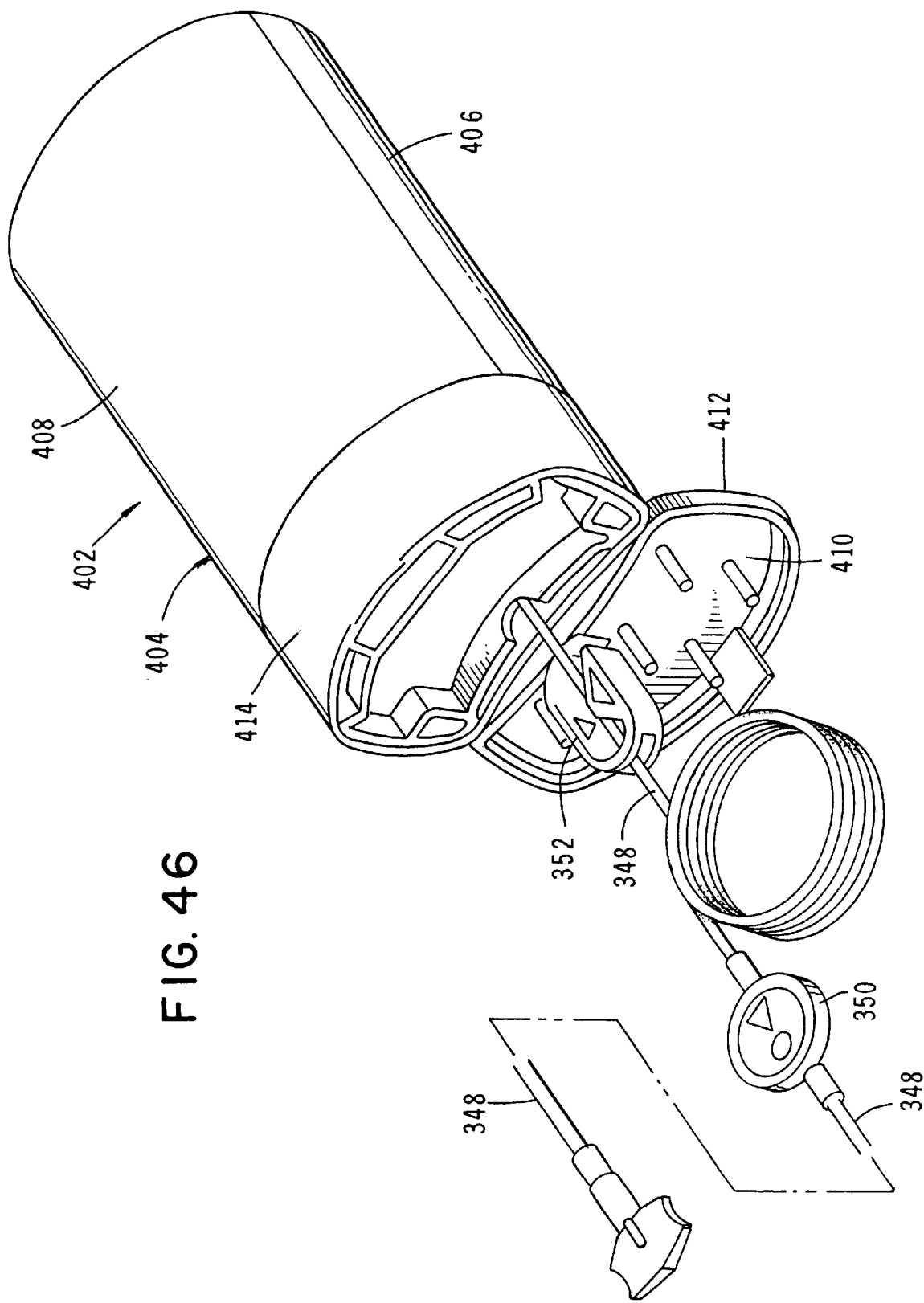
FIG. 46 is a generally perspective view of yet another form of the fluid dispenser of the invention.
Figure 49:
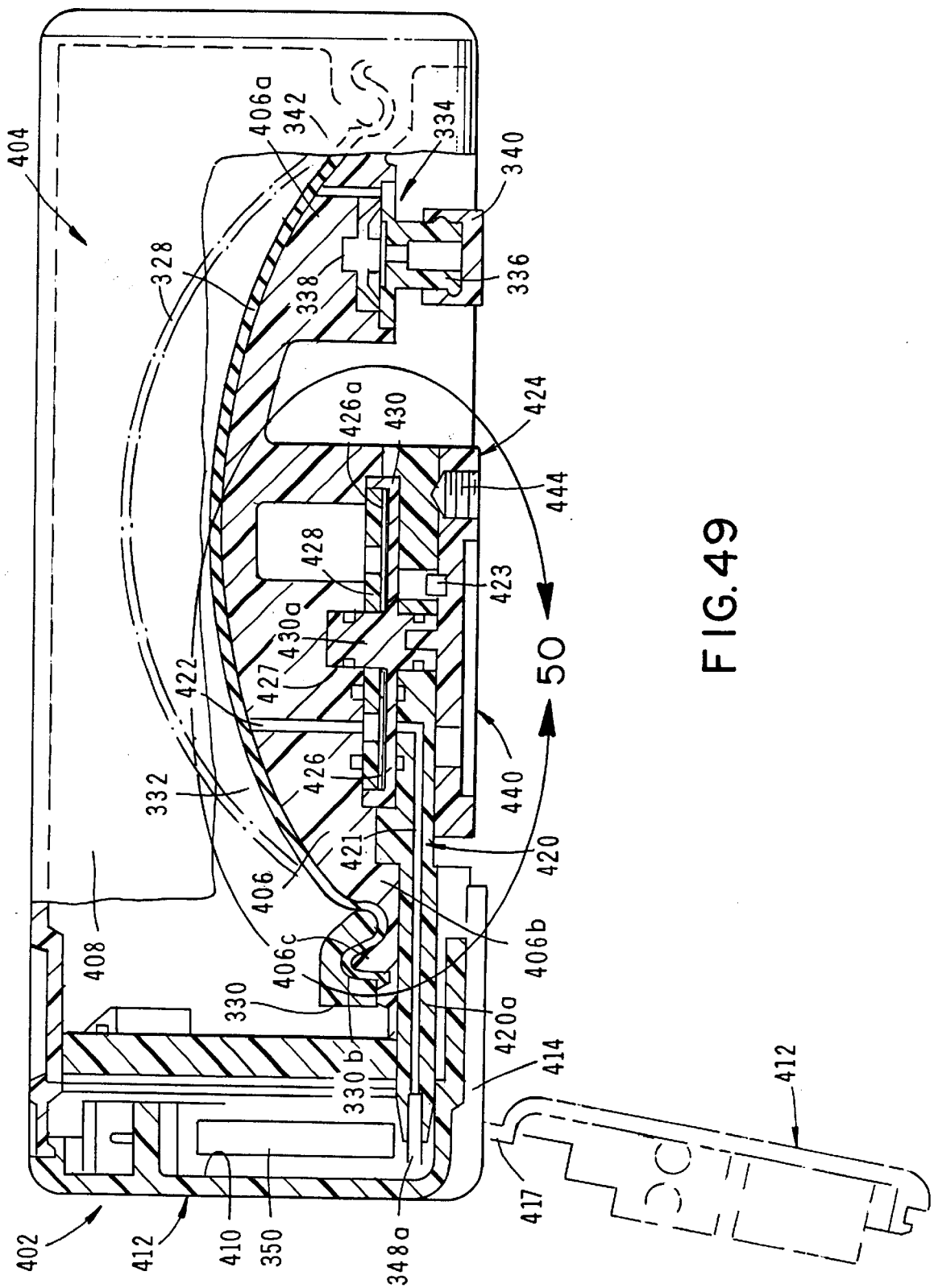
FIG. 49 is a side-elevational, cross-sectional view of the dispenser partly broken away to show internal construction.

In this latest embodiment of the invention, storage means for storing the infusion means of the apparatus is provided in the form of a storage compartment 410 formed in a closure door 412 that is hingeably connected to a forward housing portion 414 located proximate the forward end of the dispenser. In addition to forward housing portion 414, housing 404 includes the previously identified cover 408 and the base 406. Closure door 412 which functions to close the forward end of the dispenser component is movable about living hinges 417 (FIG. 47) from the open position shown in FIG. 46 to the closed position shown in FIGS. 47 and 49. In the manner indicated in FIGS. 46 and 49, compartment 410 houses the component parts of the infusion means of the invention, namely the infusion line 348, the gas vent assembly 350, the line clamp 352 and the outlet luer connector 354 (FIG. 46). The inboard end 348a of infusion line 348 is connected to the stem portion 420a of a delivery manifold 420 and communicates with reservoir 332 via an outlet passageway 422 formed in base 406 (FIG. 50) (see also FIGS. 52 and 53). As presently will be described, stem portion 420a includes a fluid passageway 421 that communicates with outlet passageway 422 via the novel fluid flow control means of this latest form of the invention.

Figure 47:
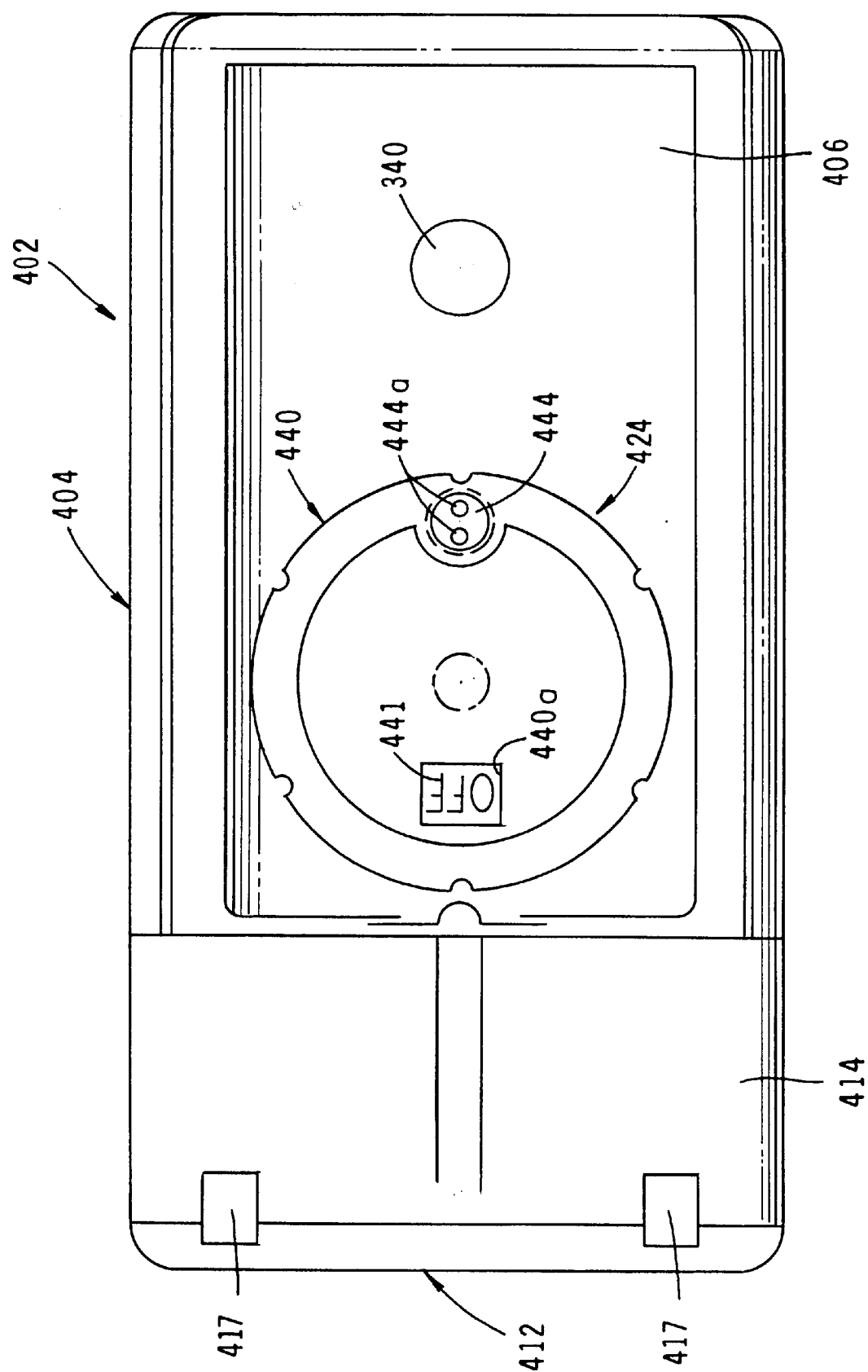
FIG. 47 is an enlarged bottom plan view of the device shown in FIG. 46.
Figure 48B:
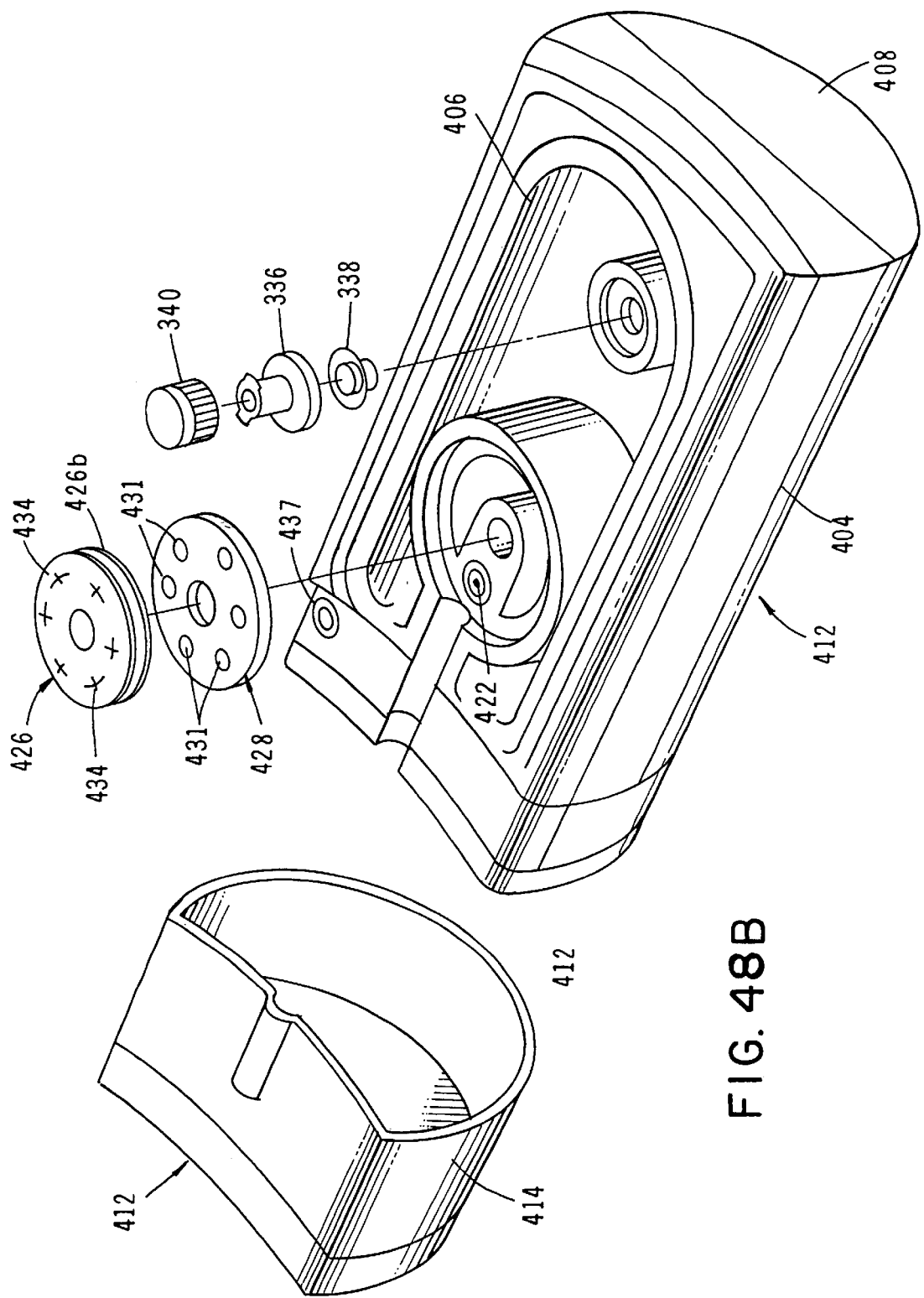

The novel fluid flow control means of the form of the invention shown in FIGS. 46 through 53 comprises a flow control assembly 424 which includes a rate control film 426 that is clamped between apertured clamping plates 428 and 430. As indicated in FIG. 50, plate 430 forms a part of a rate control housing 427 with the shaft portion 430a thereof being rotatably mounted within a cylindrical bore 429 formed in base 406 (FIG. 50). As best seen in FIG. 48, each of the plates 428 and 430 is provided with a plurality of circumferentially spaced flow apertures 431, which are indexably aligned. Apertures 431 are also aligned with laser drilled areas 434 formed in film 426. An alignment boss 436 (FIG. 51) is formed on film 426 to insure proper alignment of the film with plates 428 and 430. Connected to shaft 430a proximate its outboard end is a rate control wheel 440. Wheel 440 includes a viewing window 440a for viewing flow rate indicia 441 imprinted on delivery manifold 420 (FIG. 47). With the construction shown, by rotating control wheel 440 relative to manifold 420, which also causes rotation of the interconnected plates 428 and 430, each of the laser drilled areas 434 of film 426 can be moved sequentially into alignment with outlet passageway 422. Because each of the areas 434 is drilled with one or more microbores of a different, preselected size preferably ranging from 1 to 100 microns, the rate of fluid flowing outwardly of the device throughout passageway 422 and into delivery manifold 420 can be precisely controlled by positioning a selected area 434 in the flow path between reservoir 332 and delivery manifold 420. Using laser microbore drilling techniques of a character well known to those skilled in the art, each of the areas 434 can be tailored to precisely control the rate of fluid flow therethrough. A filter member 426a is disposed between plates 428 and rate control film 426 to prefilter fluid flowing toward areas 434 (FIG. 48). As best seen in FIG. 50, elastomeric O-rings 437 are strategically positioned between housing 427 and base 406 to prevent leakage between the assemblages.

With the construction described in the preceding paragraphs, once the fluid reservoir is appropriately filled, the desired rate of infusion to the patient can be set by the physician or other caretaker by rotating the control member 440 until the desired flow rate appears through window 440a. Rotation in the opposite direction is prevented by a blocking tab 423. Once the flow rate is set, a threaded locking number or screw 444, which is threadably connected to control member 440 in the manner shown in FIGS. 49 and 50 is rotated to secure the control member against further rotation. Locking member 444, which comprises a part of the locking means of this latest form of the invention, includes spaced-apart apertures 444a (FIG. 47) which receive spaced apart spanner elements 394a that are formed on physician's key 394 (FIG. 35). Upon rotation of screw 444, the tapered end 444b thereof will be moved inwardly relative to the lower surface of manifold 420 and into a tapered bore 445 formed in the manifold (FIG. 50) so as to block further rotation of control wheel 440. With the control wheel thus locked against rotation, the rate of infusion to the patient of the medicinal fluids contained within reservoir 332 cannot be changed unless and until the physician or caregiver rotates screw 444 in an opposite direction using the physician's key 394.

Turning next to FIGS. 54 through 60, yet another form of the fluid dispenser assembly of the apparatus of the invention is there illustrated and generally designated by the numeral 452. The fluid dispenser component of the apparatus is also somewhat similar to the fluid dispenser illustrated in FIGS. 35 through 45 and like numerals are used to identify like components. The fluid dispenser here comprises a housing assembly 454 having a base 456. A stored energy source, or distendable membrane 328 (FIG. 56) is superimposed over base 456 and, in the manner previously described, is clamped thereto by a clamping ring 330. A cover 331 of identical design to that shown in FIGS. 35 through 45 is provided for enclosing the stored energy source and the capture ring. Base 456 includes an ullage defining protuberance 456a and a membrane capture portion 456b. Base 456 also includes an upstanding tongue 456c which extends about the perimeter of the base and is closely receivable within a groove 330b formed in the capture ring 330. When the base and the membrane capture ring are assembled in the manner shown in FIG. 56, the periphery of distendable membrane 328 will be securely clamped within groove 330b by tongue 456c.

Also forming a part of housing assembly 454 is filling means for filling the fluid reservoir 332 of the fluid dispenser assembly, which reservoir is defined by the upper surface of base 456 and the lower surface of distendable membrane 328. This filling means is also identical in construction and operation to the previously described fill assembly 334 which includes a fill port 336 which is connected to base 456 and valve means for controlling fluid flow toward reservoir 332.

As before, during the reservoir filling step, a closure cap 340 is first removed and a fill line having an appropriate luer connector is connected to fill port 336. This done, fluid under pressure can be urged to flow into inlet passageway 342 of the fluid dispenser via umbrella valve 338 and thence into a reservoir 332. As the fluid under pressure flows into the reservoir, membrane 328 will distend outwardly from protuberance 456a in the manner shown by the phantom lines in FIG. 56.

In this latest embodiment of the invention, the infusion means of the apparatus, which is identical to that previously described, is conveniently stored within the face of forward housing portion 344. One end of infusion line 348 is connected to base 456 and communicates with reservoir 332 via a base passageway 460 and outlet passageway 462. In a manner presently to be described, the novel fluid flow control means of this latest form of the invention is disposed between the inlet end of base passageway 460 and the outlet end of outlet passageway 462 (see FIG. 56).

Figure 54:
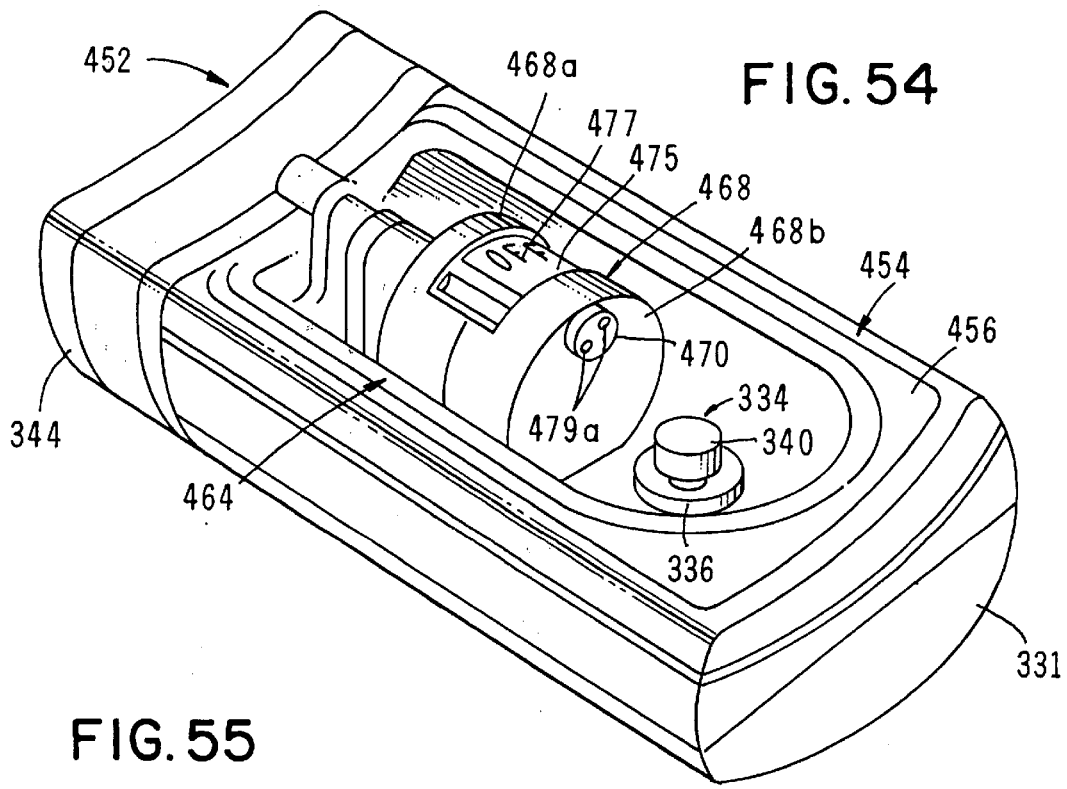
FIG. 54 is a generally perspective view of still another form of the fluid dispenser of the invention.
Figure 60:
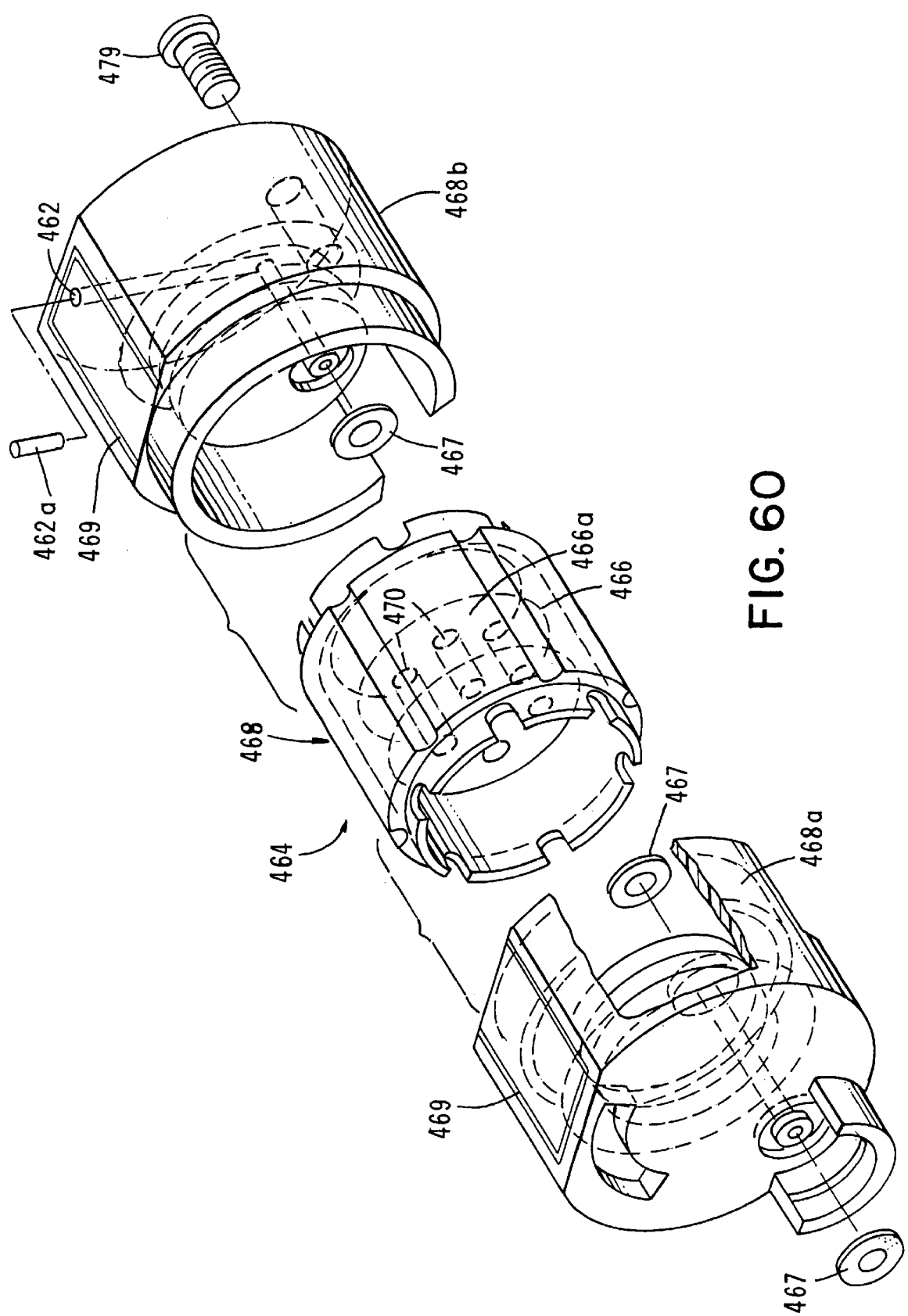
FIG. 60 is an enlarged, generally perspective, exploded view of the flow control assembly of this latest form of the invention.

The novel fluid flow control means of the form of the invention shown in FIGS. 54 and 60 comprises a flow control assembly 464 which adjustably controls the rate of fluid flow from the reservoir of the apparatus to base passageway 460. Flow control assembly 464 is mounted within base 456 and, as best seen in FIGS. 58, 59 and 60, includes a control knob 466 that is rotatably mounted within flow control assembly 464. O-rings 467 carried by a control knob housing 468 sealably engage control knob 466 and prevent leakage among the various cooperating components. As best seen in FIG. 60, control knob housing 468 is formed by two cooperating parts 468a and 468b within which the control knob rotates. Control knob housing 468 can be affixed to base 456 by any suitable means such as adhesive bonding or sonic welding. When sonic welding is used, the housing is provided with sonic bond energy directors 469 of a character well understood in the art (FIG. 60).

As indicated in FIGS. 57, 58, and 59, control knob 466 includes a central wall 466a which uniquely carries a plurality of circumferentially spaced apart flow restrictors each of which can be selectively moved into index with base passageway 460 by rotating knob 466 relative to knob housing 468. In the embodiment of the invention shown in FIGS. 56 through 60, the flow restrictors are provided in the form of porous rate control frits 470 (see FIGS. 57 and 58), which are secured in place within apertures 472 formed in wall 466a by a moldable elastomer 473 under compression fit. With the construction shown in the drawings, by rotating knob 466 relative to housing 468, each of the rate control frits 470 can be moved sequentially into alignment with base passageway 460. Because each of the frits 470 is of a different, preselected porosity, it is apparent that the rate of fluid flowing outwardly of the device through base or delivery passageway 460 can be precisely controlled by positioning a particular frit in the flow path. Fluid flowing toward the rate control means if prefiltered by filter means 462a.

Figure 55:
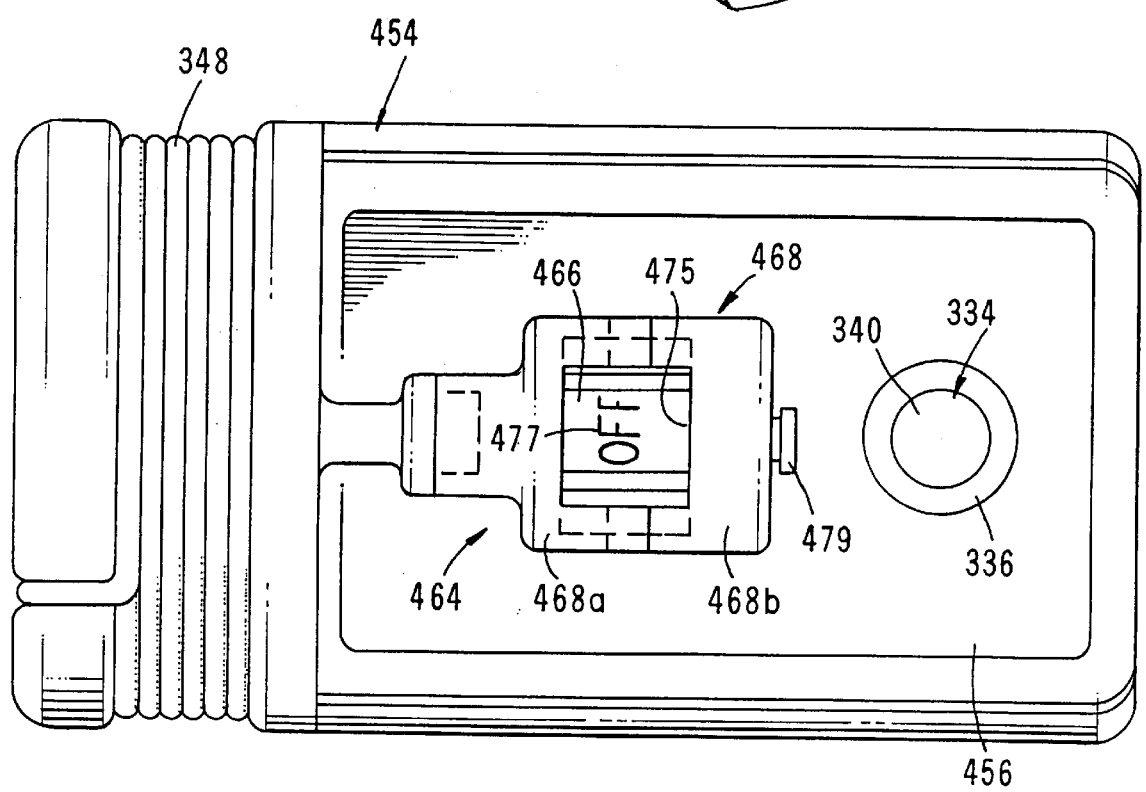
FIG. 55 is an enlarged bottom plan view of the device shown in FIG. 54.

As shown in FIGS. 54 and 55, control knob housing 468 includes a viewing window 475 for viewing flow rate indicia 477 imprinted on control knob 466. With the construction shown by rotating control knob 466 relative to housing 468, each of the flow rate indicia imprinted on knob 466 will come into view as the corresponding rate control frit aligns with delivery passageway 460.

Figure 56:
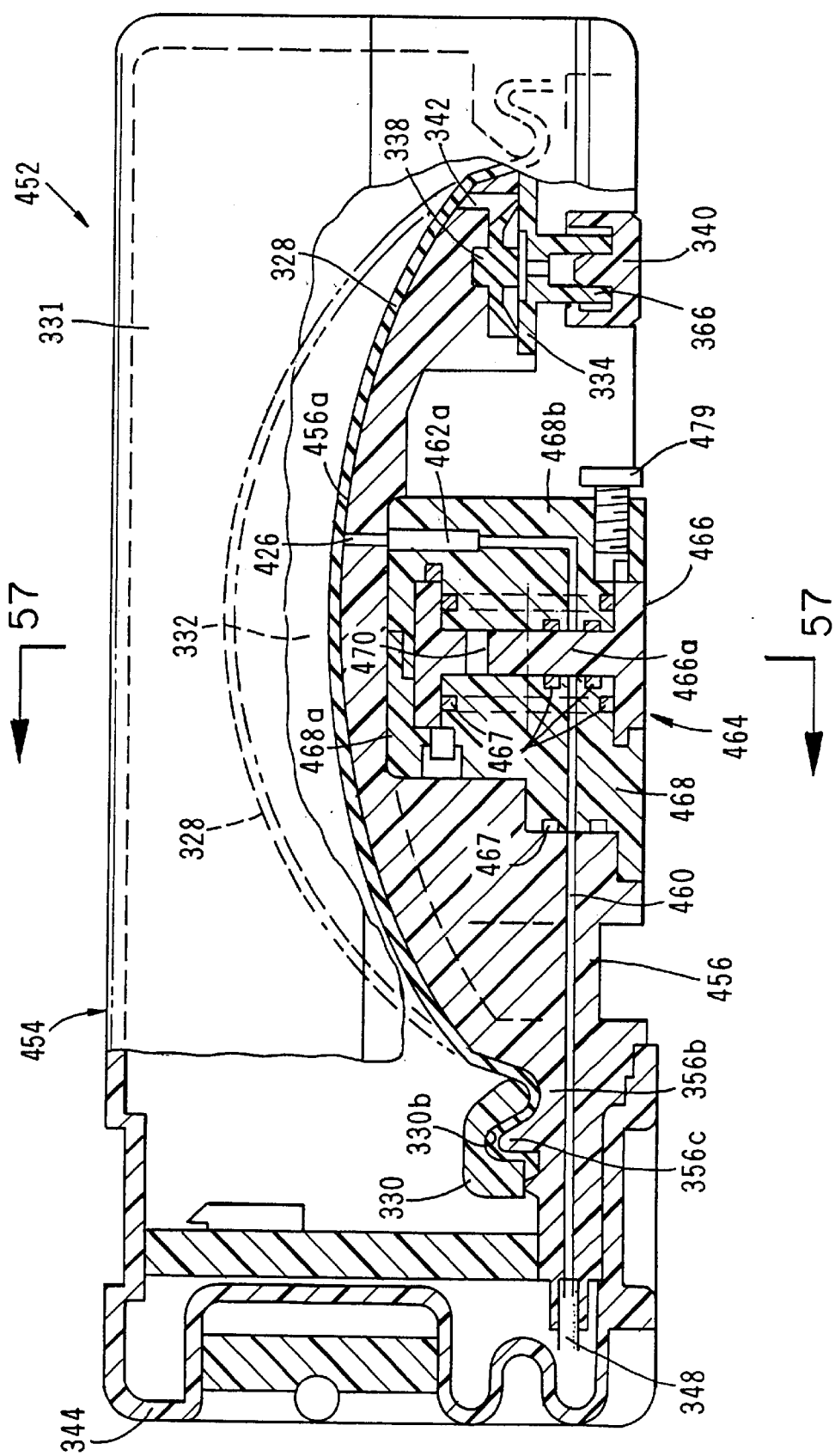
FIG. 56 is a side-elevational, cross-sectional view of the dispenser.

With the construction described in the preceding paragraph, once the fluid reservoir is appropriately filled, the desired rate of infusion to the patient can be set by the physician or other care taker by rotating the control knob 466 until the desired flow rate appears through window 475. Locking member 479, which is threadably connected to control knob housing 468 in the manner indicated in FIGS. 56 and 60 is rotated to secure the control member against further rotation. Locking member 479, which comprises a part of the locking means of this latest form of the invention, includes spaced-apart apertures 479a (FIG. 54) which receive spaced-apart spanner elements 394a that are formed on physician's key 394 (FIG. 35). Upon rotation of screw 479, the inboard end thereof will be moved inwardly relative to housing 468 and into locking engagement with knob 466 so as to block its further rotation. With the control knob thus locked against rotation, the rate of infusion to the patient of the medicinal fluids contained within reservoir 332 cannot be changed unless and until the physician or caregiver rotates screw 479 in an opposite direction using the physician's key 394.

In each of the previously described embodiments of the invention, the various materials suitable for use in constructing the base and cover components include metals, rubber or plastics that are compatible with the liquids they contact and are preferably non-allergenic type material. Examples of such materials are: stainless steel, aluminum, latex rubber, butyl rubber, nitrile rubber, polyisoprene, styrenebutadine copolymer, silicones, polyolefins such as polypropylene and polyethylene, polyesters, polyurethane, polyamides and polycarbonates. Suitable materials for use in constructing the stored energy means of the invention are described in incorporated by reference U.S. Pat. No. 5, 205, 820.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. A device in infusing medicinal fluid into a patient at a controlled rate comprising:
    (a) a housing having outlet passageway;
    (b) a stored energy means disposed within said housing for forming a fluid reservoir having an inlet and an outlet in communication with said outlet passageway of said housing, said stored energy means comprising at least one generally planar distendable member, said member being distendable as a result of pressure imparted by fluids to establish internal stresses, said stresses tending to move said member toward a less distended configuration;
    (c) fluid flow control means carried by said housing for controlling the rate of fluid flow from said reservoir toward said outlet passageway of said housing, said fluid flow control means comprising a rate control film rotatably connected to said housing intermediate said reservoir outlet and said outlet passageway, said rate control film having first and second spaced apart porous areas, said film being rotatable from a first position wherein said first porous area is aligned with said outlet of said reservoir and said outlet passageway and a second position wherein said second porous area is aligned with said outlet of said reservoir and said outlet passageway.

2. The devices defined in claim 1 in which said first and second porous areas each comprise laser drilled areas.

3. The devices defined in claim 1 further comprises a control wheel carried by said housing for rotating said rate control film.

4. The device as defined in claim 3 further including means for locking said control wheel against rotation.

5. The device defined in claim 4 in which said locking means comprises a threaded member threadably connected to a base for rotation between a first position wherein said control wheel is locked against rotation and a second position wherein said control wheel is rotatable.

6. A device for use in infusing medicinal fluid into a patient at a controlled rate comprising:
   (a) a housing having a bottom portion and an outlet passageway;
   (b) a stored energy means disposed within said housing for forming a fluid reservoir having an inlet and an outlet in communication with said outlet passageway of said housing, said stored energy means comprising a least one generally planar distendable member, said member being distendable as a result of pressure imparted by fluids to establish internal stresses, said stresses tending to move said member toward a less distended configuration;
   (c) fluid flow control means carried by said housing for controlling the rate of fluid flow from said reservoir toward said outlet passageway of said housing, said fluid flow control means comprising a control knob rotatably connected to said housing intermediate said reservoir outlet and said outlet passageway, said control knob having first and second spaced apart porous rate control frits, said control knob being rotatable from a first position wherein said first porous rate control frit is aligned with said outlet of said reservoir and said outlet passageway and a second position wherein said second porous rate control frit is aligned with said outlet of said reservoir and said outlet passageway.

7. The devices defined in claim 6 in which flow rate control indicia are imprinted on said control knob.

8. The device as defined in claim 6 further including filling means for filling said reservoir, said filling means comprising a fill port connected to said housing and means disposed within said housing for controlling fluid flow between said fill port and said reservoir.

9. The device as defined in claim 6 further including locking means for locking said control knob against rotation.

10. The devices defined in claim 6 further including locking means for locking said control knob against rotation, said locking means comprising a locking member having spaced-apart spanner receiving apertures.

11. The device as defined in claim 6 in which said control knob is accessible from said bottom portion of said housing.

12. A device for use in infusing medicinal fluid into a patient at a controlled rate comprising:
   (a) a fluid dispenser including:
      (i) a housing having a base, having an upper portion and a lower portion;
      (ii) a stored energy means for forming, in conjunction with said upper portion of said base, a fluid reservoir having an inlet and an outlet, said stored energy means comprising at least one distendable member superimposed over said upper portion of said base, said member being distendable as a result of pressure imparted by the fluids to be infused to establish internal stresses, said stresses tending to move said member toward a less distended configuration
      (iii) an outlet passageway formed in said base for communication with said outlet of said fluid reservoir
   (b) fluid flow control means carried by said base for controlling the rate of fluid flow from said reservoir toward said outlet passageway, said fluid flow control means comprising a control knob rotatably connected to said base intermediate said reservoir outlet and said outlet passageway, said control knob being accessible from said lower portion of said base and having first and second spaced apart rate control fits, said control knob being rotatable from a first position wherein said first rate control frit is aligned with said outlet of said reservoir and said outlet passageway and a second position wherein said second rate control fit is aligned with said outlet of said reservoir and said outlet passageway;
   (c) infusion means in communication with said outlet passageway for infusing fluid from said reservoir into the patient and
   (d) filling means connected to said housing for filling said reservoir.

13. The device as defined in claim 12, further including means for locking said control knob against rotation.

14. The device as defined in claim 12, in which said filling means comprises a fill port connected to said lower portion of said housing.

15. The apparatus as defined in claim 14 in which said filling means further comprises a valve means disposed within said housing for controlling fluid flow between said fill port and said reservoir.

* * * * *